United States Patent [19]

Hiyama et al.

[11] Patent Number: 5,124,789
[45] Date of Patent: Jun. 23, 1992

[54] MEDICAL IMAGE FILING APPARATUS AND FILING METHOD FOR REGISTERING IMAGES FROM A PLURALITY OF IMAGE OUTPUT DEVICES IN A SINGLE EXAMINATION

[75] Inventors: Keiichi Hiyama, Akishima; Yutake Konomura, Tachikawa; Akihiko Yajima, Kunitachi, all of Japan

[73] Assignee: Olympus Optical Co., Ltd., Tokyo, Japan

[21] Appl. No.: 646,896

[22] Filed: Jan. 28, 1991

Related U.S. Application Data

[62] Division of Ser. No. 407,508, Sep. 6, 1989, Pat. No. 5,029,016.

[30] Foreign Application Priority Data

Sep. 7, 1988 [JP] Japan ............................... 63-224995
Sep. 4, 1989 [JP] Japan ................................. 1-230229

[51] Int. Cl.$^5$ .............................................. H04N 7/18
[52] U.S. Cl. ........................................ 358/98; 358/403; 358/110; 128/6

[58] Field of Search ................. 358/98, 403, 471, 110, 358/112, 111; 128/4, 6

[56] References Cited

U.S. PATENT DOCUMENTS

| | | | |
|---|---|---|---|
| 4,506,342 | 3/1985 | Yamamoto | 358/403 |
| 4,513,390 | 4/1985 | Walter et al. | 358/403 |
| 4,768,099 | 8/1988 | Mukai | 358/403 |
| 4,979,497 | 12/1990 | Matsura et al. | 358/98 |

*Primary Examiner*—John K. Peng
*Attorney, Agent, or Firm*—Armstrong & Kubovcik

[57] ABSTRACT

A system comprises a plurality of image signal generating apparatuses which each generate an image signal using an electronic endoscope, an ultrasonic scope or the like and which are connected to a common large capacity filing apparatus through an interface so that image data can be recorded together with image information with respect to the data in the unit of any number of images for a single examination and the image data recorded can be searched for in the unit of a single examination.

20 Claims, 61 Drawing Sheets

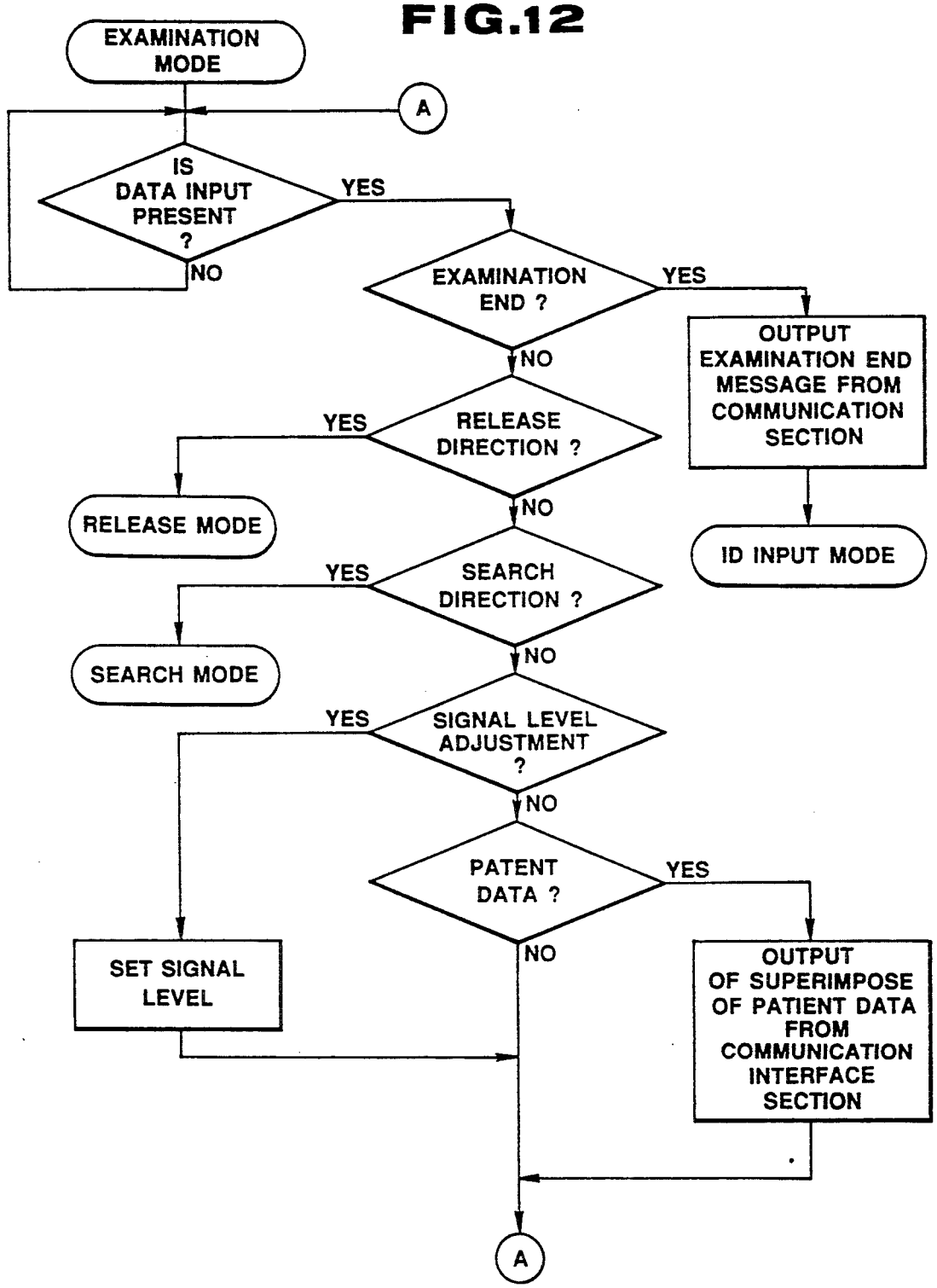

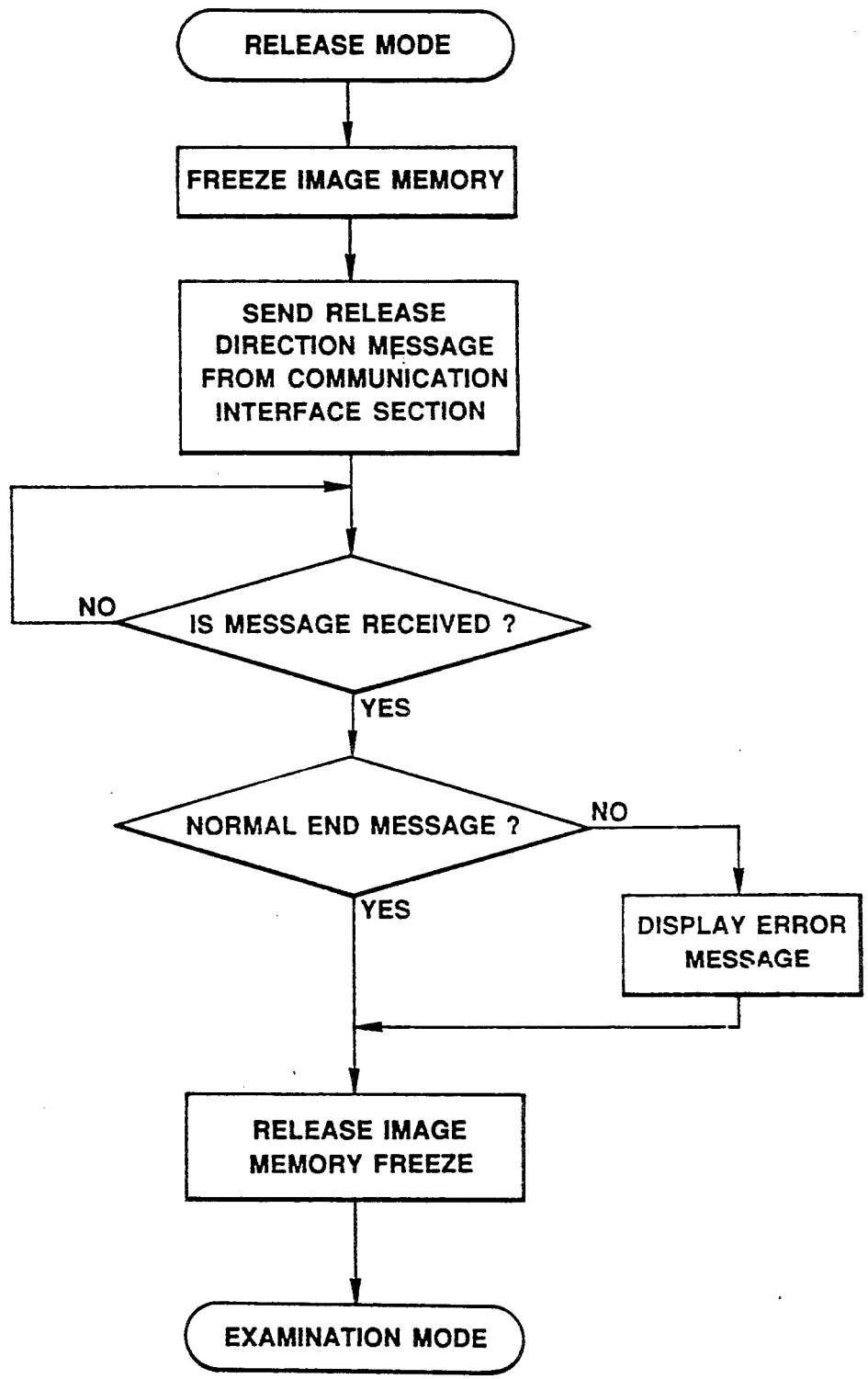

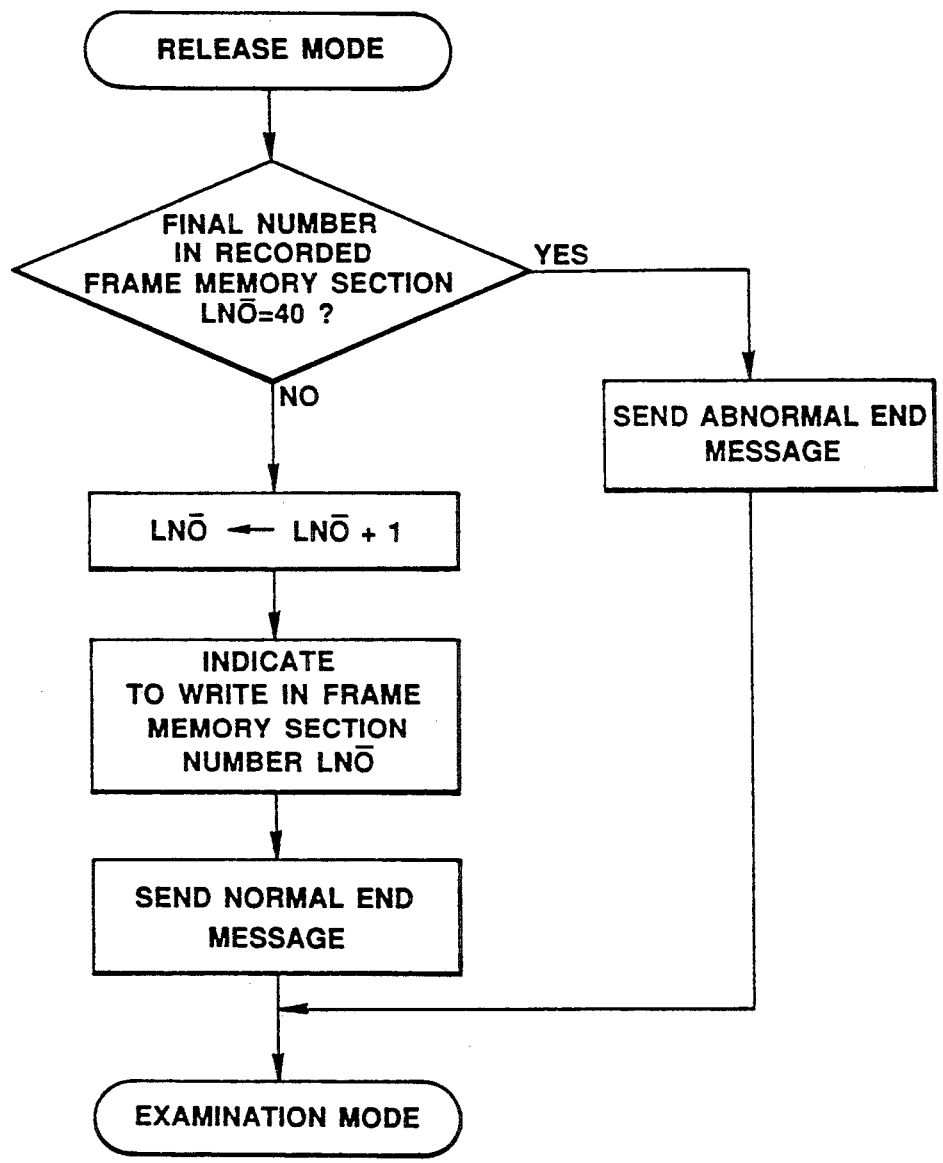

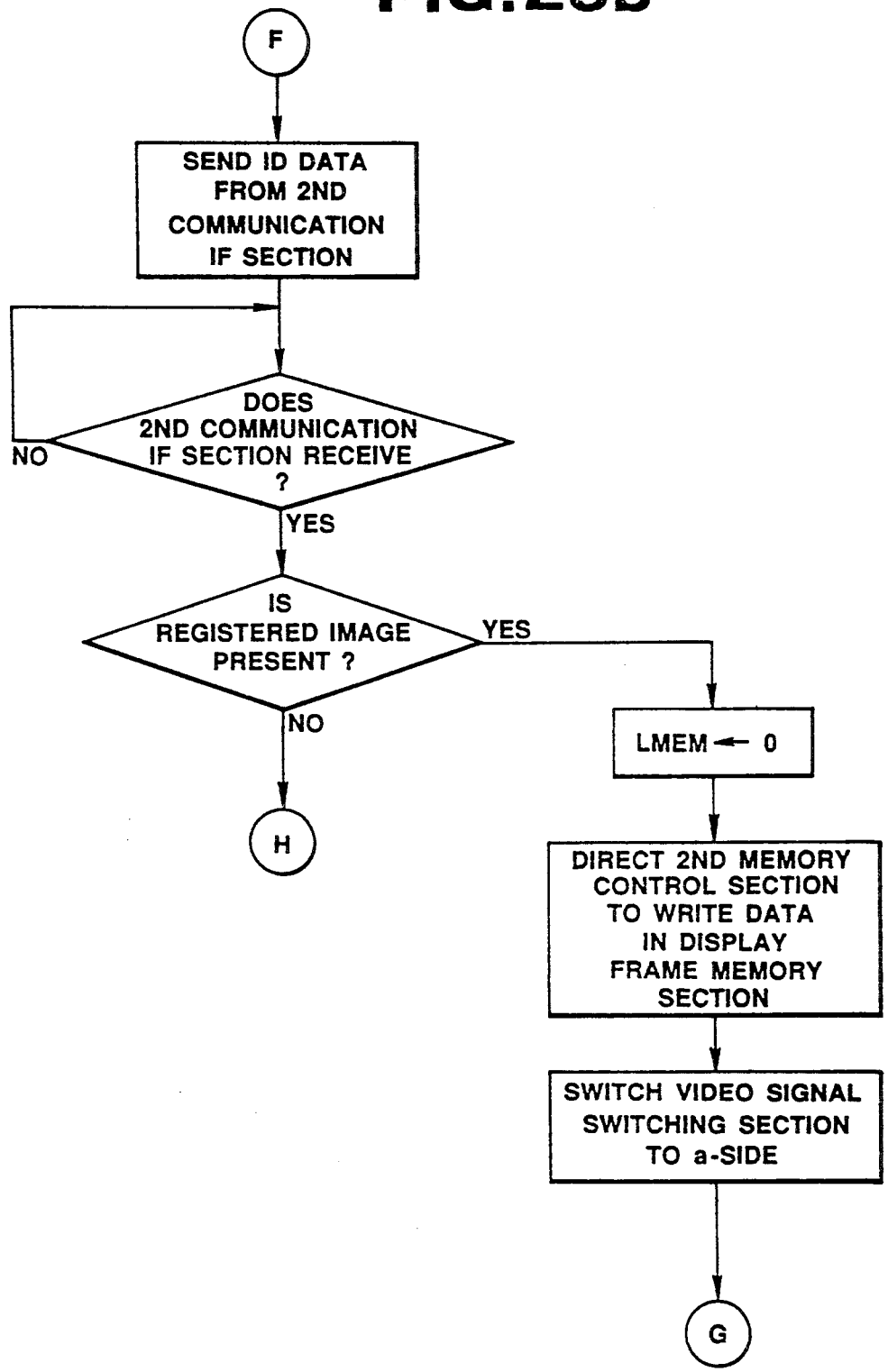

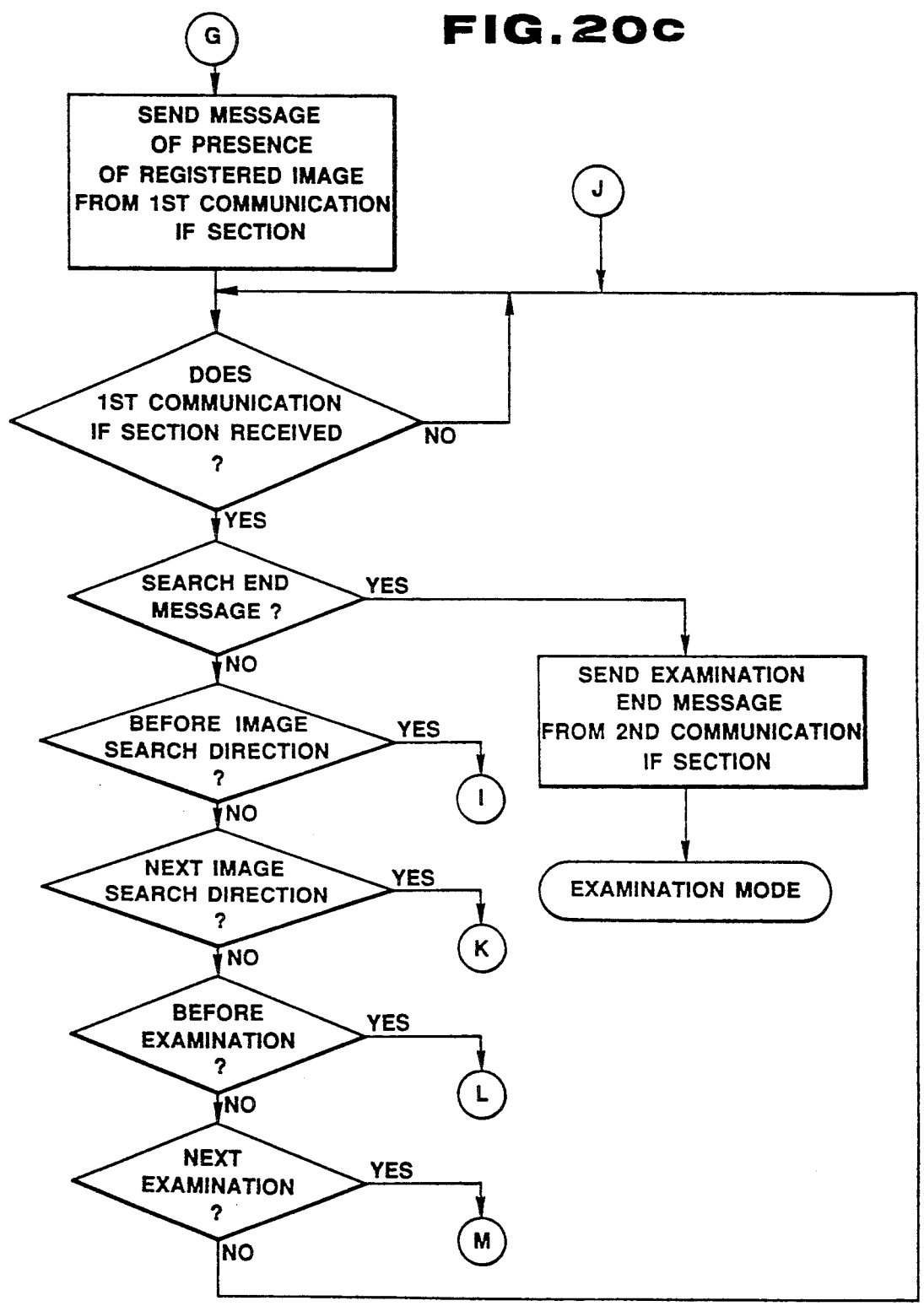

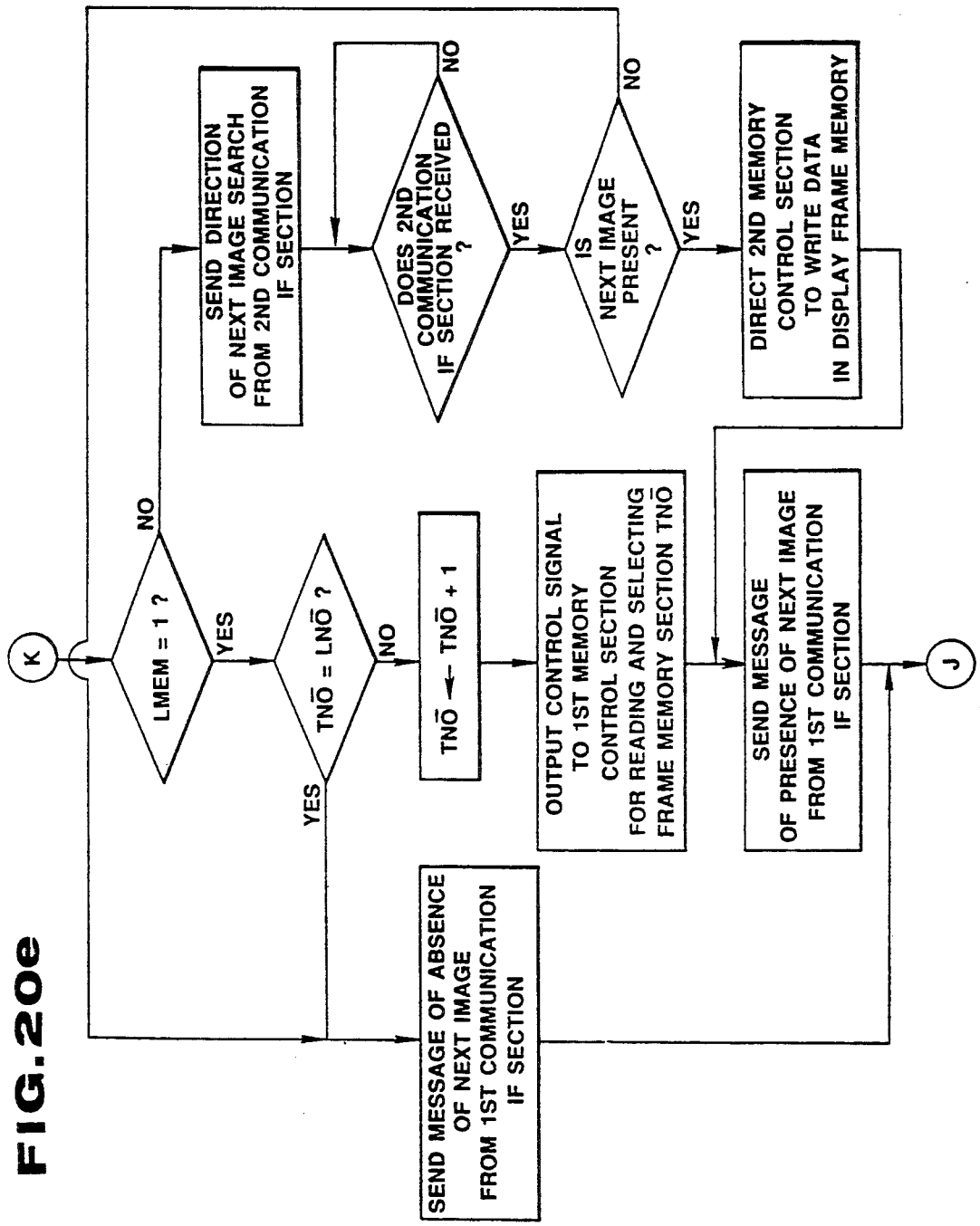

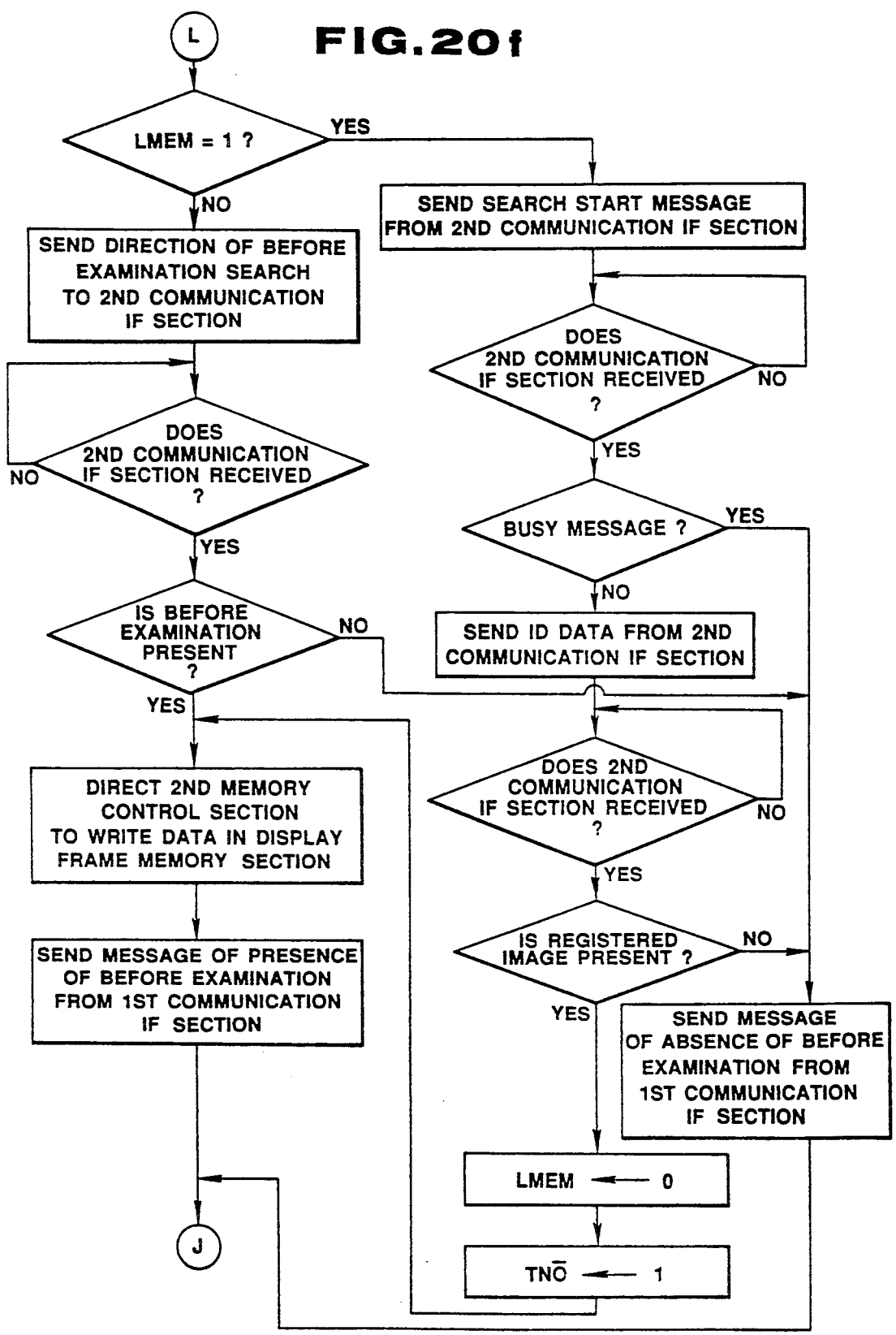

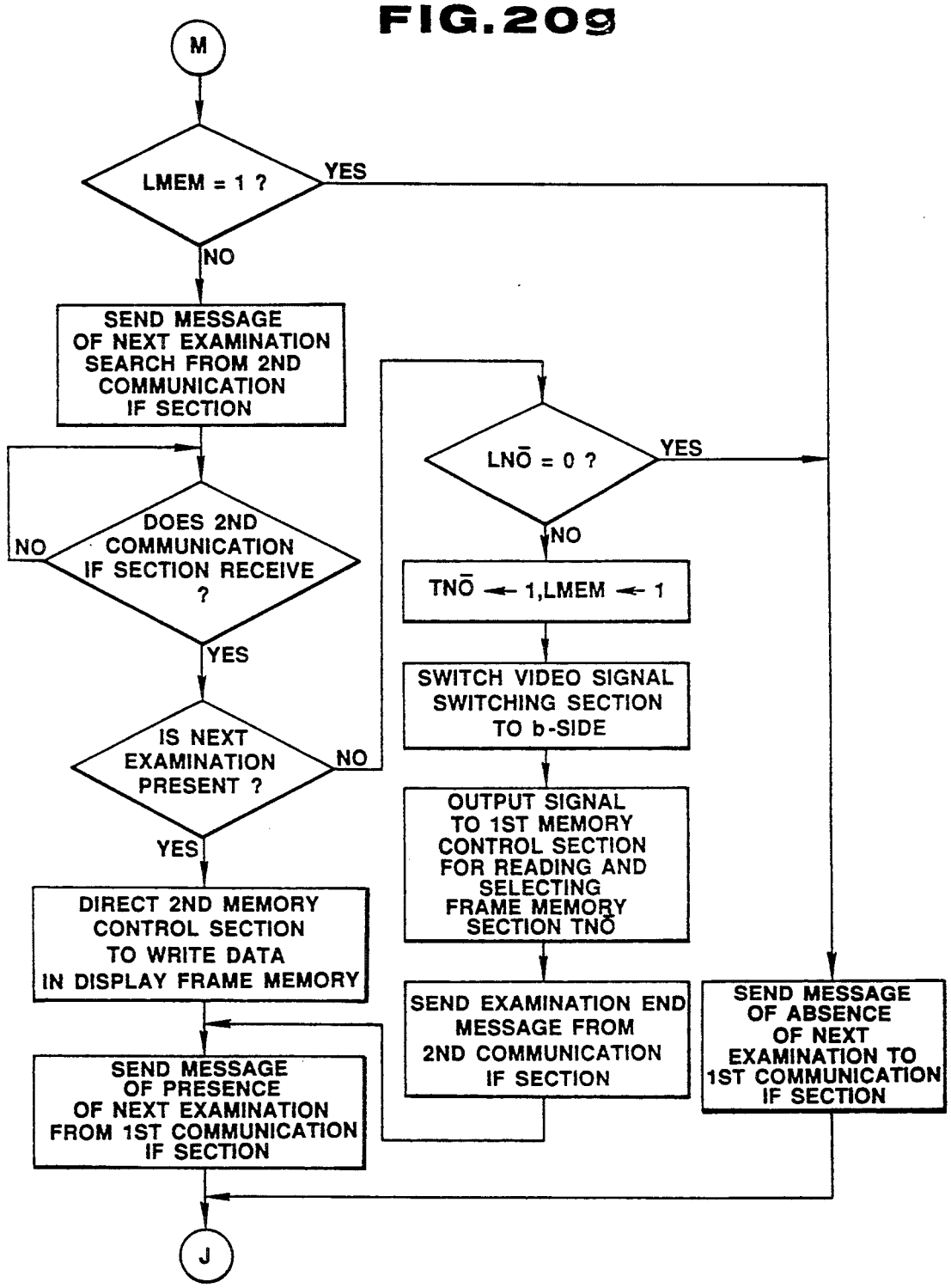

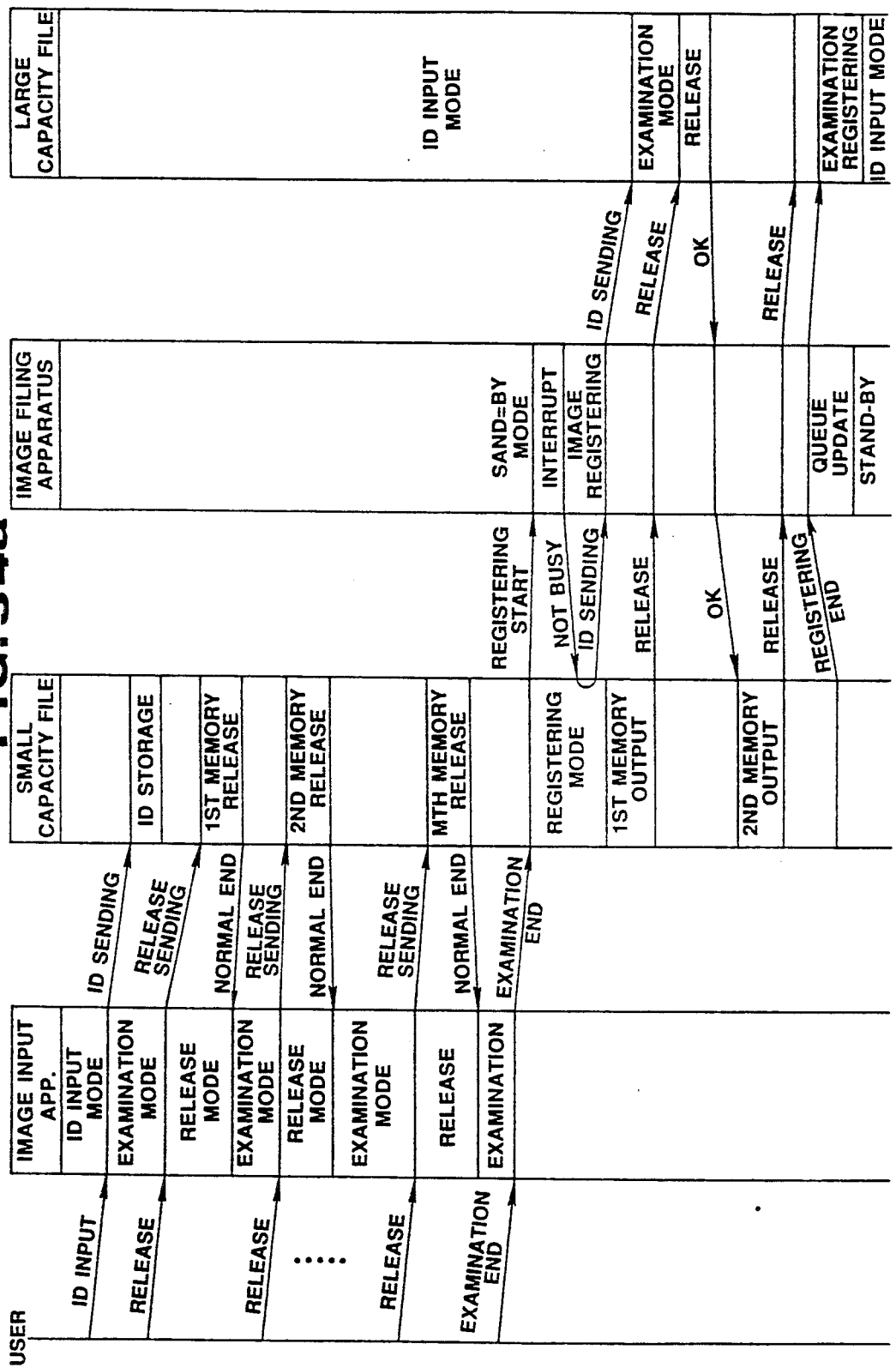

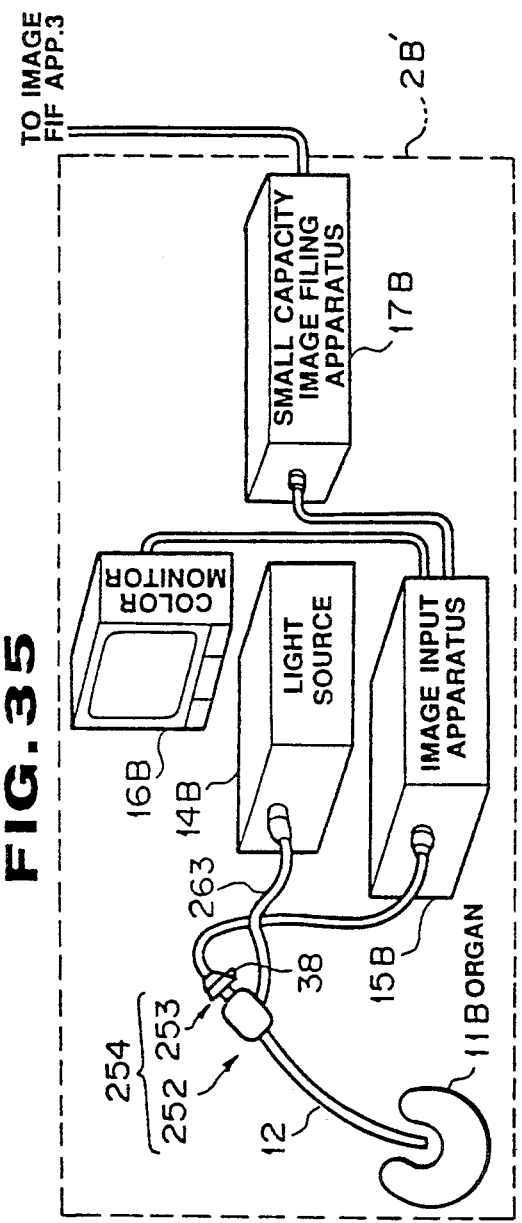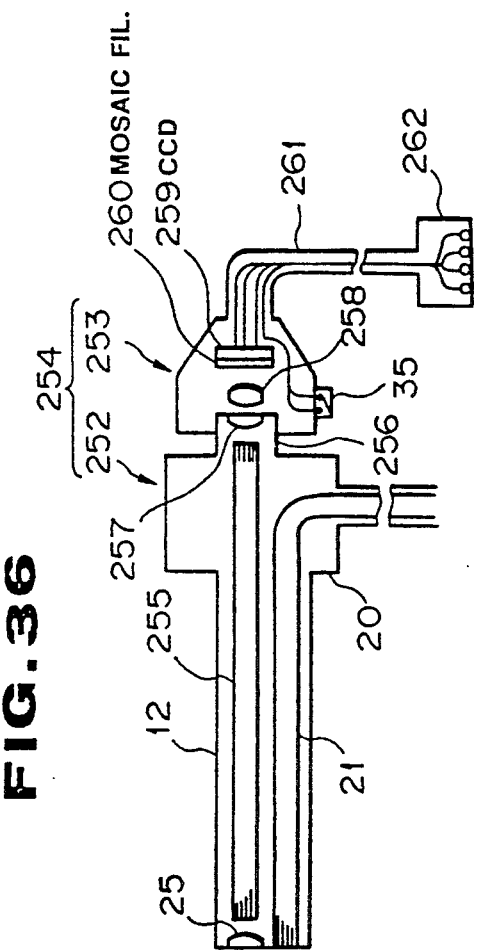

MEDICAL IMAGE FILING APPARATUS AND FILING METHOD FOR REGISTERING IMAGES FROM A PLURALITY OF IMAGE OUTPUT DEVICES IN A SINGLE EXAMINATION

This is a division of application Ser. No. 407,508 filed Sept. 6, 1989, U.S. Pat. No. 4,029,016.

BACKGROUND OF THE INVENTION

Field of the Invention and Description of Related Art

The present invention relates to a medical filing apparatus and a filing method which are capable of registering images from a plurality of image signal generators in a single examination.

In recent years, endoscopes which allow observation of objects such as the organs in the coelom by inserting the insertion portions thereof into the coelom or the like have been widely used. Electronic endoscopes (or electronic scopes) in which a solid state image sensor such as a CCD or the like is incorporated into the end portion of the insertion portion or external TV camera-equipped scopes in which the ocular portion of an optical endoscope is equipped with a TV camera containing a solid state image sensor have also been used.

The above-described electronic scopes or external TV camera-equipped scopes (represented by the electronic scope) have a disadvantage in that images can be easily recorded and regenerated and thus easily reexamined in detail after diagnoses.

In the electronic scopes, image filing apparatuses are used for storing scope images picked up by the electronic scopes.

As shown in FIG. 1, an image filing apparatus 701 of prior art comprises an image input device 703, which is connected to an electronic scope 702, and an image filing apparatus 704, which are directly connected to each other.

The electronic scope 702 has a long thin insertion portion 705 which can be inserted into an organ 706 or the like. The image signal imaged by the electronic scope 702 is input to the image input device 703 for signal processing. There the signal is converted into an image signal such as an RGB video signal or the like, and is then input to a color monitor for color display, as well as being input to the image filing apparatus 704, for example, in which an image frozen by a release operation is recorded in the image filing apparatus 704. To the electronic scope 702 is supplied illumination light from a light source 709.

FIG. 2 shows the configuration of the above-mentioned image input device 703.

The image signal imaged by the electronic scope 702 is input to an image processing section 711 which outputs a drive signal for driving CCD 712 in the electronic scope 702. The image signal read from the CCD 712 by the application of the drive signal thereto is converted into an RGB video signal and is then output to an image memory 713. The image processing section 711 also serves to control the level of the image signal, i.e., the balance between R and B signals for a G signal. The patient data and the error massage sent from a control section 714 are superimposed on the RGB video signal and displayed.

The above-described image memory 713 outputs an image without any change in which the RGB video signal input from the image processing section 711 written in correspondence with the control signal sent from the control section 714, and the writing is temporarily stopped for outputting the signal of a static image to an image signal switching device 715 and to the external image filing apparatus 704. The image signal switching device 715 functions to switch the signal sent from the image memory 713 and the RGB video signal sent from the external image filing apparatus 704 by using the control signal from the control section 714 and output one of these signals to the color monitor 707.

To the above-described control section 714 are input signals form a data input section 716 and a communication interface section 717 so that the control section 714 controls each of the sections in the image input device 703 on the basis of the signals.

In the above-mentioned data input section 716 are input data such as names of patients, the dates of birth of patients and the like, which are superimposed on the RGB signal, and controls such as image release, image retrieval and the like when the user operates the keyboard.

In addition, the communication interface section 717 is, for example, an interface section which employs serial transfer of the RS-232C specification for data input from and output to the external image filing apparatus 704 on the basis of the control from the control section 714.

FIG. 3 shows the configuration of the bulk image filing apparatus 704.

The RGB signal output from the image memory 713 of the image input device 703 is input to a color monitor 722 through a video signal switcher 721, as well as being input to a still picture recording optical disk recorder 723.

The video signal switcher 721 is also connected to the still picture recording disc device 723 (referred to as "still picture recorder" or "optical disk recorder" hereinafter) so as to switch the RGB signals from the image input device 703 and the still picture recorder 723 and to output one of the signals to the color monitor 722.

The image filing apparatus 704 also contains CPU 725 for various controls using a working or program memory 726. The CPU 725 is connected through bus lines to a first communication interface section 727, an interface 728 connected to the switch 721, a second communication interface section 729 connected to the still picture recorder 723 and a hard disk controller 732 connected to a database hard disk 731.

FIG. 4 shows a typical example of the use of the apparatus 701.

The image input device 703 and the image filing apparatus 704 are in ID input mode in the initial state, and the image input device 703 is put into examination mode when the user operates the data input section 716 for inputting the ID of a patient. The ID input is transmitted to the communication interface 727 in the image filing apparatus 704 through the communication interface section 717 in the image input device 703 and a communication line. When the ID signal sent is input to the CPU 725 in which it is distinguished that the signal is an ID input, the image filing apparatus 704 is transferred to examination mode.

Then, when the user performs a release operation, the image input device is brought into release mode, in which all writing in the image memory 713 is inhibited and the image memory 713 assumes a still picture state. At the same time, a release signal is transmitted to the image filing apparatus 704 over the communication line so as to set the release mode, in which a still picture is recorded in the still picture recorder 723 after the release operation. If the recording is carried out normally, the image filing apparatus 704 sends an OK signal of release to the image input device 703 over the communication line and is again put into the examination mode.

When the user then performs a search operation, the image input device 703 is put into (image) search mode, as well as sending a search start signal to the image filing apparatus 704 which is put into search mode when a search is possible. When the apparatus 704 is put into search mode, an OK signal for searching is returned to the image input device 703, and the image signal switch 715 is switched so that the image from the image filing apparatus can be displayed. For example, when an input operation for searching for the next image is performed, a search signal for the next image is sent. When the next image is searched for, an OK signal for searching is returned to the image input device 703, and the image is displayed on the color monitor 707.

In this way, when the search for desired images is completed, the input for examination end causes the image input device 703 to return to the ID input mode, and the signal for examination end to be sent to the image filing apparatus 704 over the communication line. The image filing apparatus 704 registers release examination information for the ID in the database of the hard disk 731 through the hard disk controller 732 and returns to the ID input mode in the initial state.

In the above-mentioned prior art, since one image filing apparatus 704 is used for each image input device 703, for example, scope images imaged by different electronic scopes must be recorded in different image filing apparatuses. When it is desired to examine the changes over time in symptoms and treatment, therefore. there is a disadvantage in that it is necessary to use a plurality of image filing apparatuses in order to conduct an examination.

There is thus a demand for an image filing apparatus (or system) which is capable of collectively controlling scope images respectively generated by a plurality of image input devices by using a single filing apparatus when the image input devices are simultaneously operated.

The time required for recording analogue video signals in an image recorder using an optical disk or the like is essentially about 0.5 second. When the frequency of release during endoscopy is considered, it is therefore sufficient to provide a switch for selecting one of a plurality of input signals if the signals from a plurality of input sources are recorded in a single recorder.

This configuration, however, has the following problems:

Although it is convenient to handle the images in the unit of a single examination during observation (regeneration) at a meeting for diagnosing a disease by doctors or during explanation of the conditions of a disease to the patient after the examination, the images for a single examination are not continuously recorded on a track in the above-described apparatus which employs a switch because the apparatus allows a plurality of examination images to be recorded at random on the optical disk. In addition, since the final number of records is not known while recording the images in the course of the examination, the control of the search becomes complicated. There is also a problem in that a management program for the database and the operation thereof become complicated.

On the other hand, in the prior art disclosed in Japanese Patent Laid-Open No. 138892/1988, a common image recorder is connected to a plurality of image input devices so that no latency time occurs during recording. Each of the image input devices therefore has a frame memory so that an image is temporarily stored in the frame memory while the another image is being recorded.

Although this prior art is capable of coping with a plurality of image input devices, the problems of the configuration using a switch are not resolved thereby. In other words, this prior art is not capable of controlling in the unit of a single examination because the images from a plurality of image input devices are recorded at random on a single image recorder.

In addition, Japanese Patent Laid-Open No. 69047/1984 discloses a system for recording and searching endoscopic images in which a plurality of endoscopic systems are connected to a toll center over communication lines but does not describe the control in detail.

OBJECT AND SUMMARY OF THE INVENTION

It is an object of the present invention to provide an image filing apparatus and a filing method which are capable of recording and controlling images from a plurality of image input devices (image signal generators) for a single examination in the unit of a desired number of sheets.

It is another object of the present invention to provide an image filing apparatus and filing method which are capable of easily searching for any desired image recorded of a patient.

The present invention provides an image filing apparatus in which image signals from a plurality of image signal generators for respectively generating an endoscopic image, an ultrasonic image and the like are temporarily stored in respective memory means by release directions. The release directions are capable of storing a plurality of sheets of image data in respective image filing means. In the apparatus, image data for a single examination is stored in the memory means, for which directive signals of image registering are output, and recorded together with information data with respect to the image data in large capacity memory means of a large capacity common image filing apparatus to which respective image filing apparatus are connected when directions for image registering are output.

The present invention also provides a filing method comprising a storing process in which, of image data corresponding to the images which are respectively output from a plurality of image signal generators, image data for which a release operation is performed is stored in first memory means in connection with the index information of the images thereof; a registering process in which all the images in the same index for which registering directions are output are registered together with the index information in a common image filing apparatus provide with large capacity second memory means when registering directions are output for registering the images stored in the first memory means; and a search process for searching for and outputting the image information registered in the common image filing apparatus by inputting image information for searching in the common image filing apparatus.

BRIEF DESCRIPTION OF THE DRAWINGS

FIGS. 1 to 4 relate to prior art in which FIG. 1 is a drawing of the overall configuration of an image filing apparatus of prior art, FIG. 2 is a block diagram of the configuration of an image input apparatus, FIG. 3 is a block diagram of an image filing apparatus, and FIG. 4 is an explanatory view of the operation of each section in prior art in a typical state of use; FIGS. 5 to 34 relate to a first embodiment of the present invention in which FIG. 5 is a drawing of the overall configuration of the first embodiment, FIG. 6 is a block diagram of the configuration of an image input apparatus, FIG. 7 is a block diagram of the configuration of a small capacity image filing apparatus, FIG. 8 is a block diagram of the configuration of an image file interface apparatus, FIG. 9 is a block diagram of the configuration of a large capacity image filing apparatus, FIG. 10 is a state transition drawing of a control section of the image input apparatus, FIG. 11 is a flowchart which shows the process in the ID mode shown in the state transition drawing in FIG. 10, FIG. 12 is a flowchart which shows the process in the examination mode shown in the state transition drawing in FIG. 10, FIG. 13 is a flowchart which shows the process in the release mode shown in the state transition drawing in FIGS. 10, FIG. 14a, 14b, 14c are flowcharts which show the process in the search mode shown in the state transition drawing in FIG. 10, FIG. 15 is a state transition drawing which shows each operation mode of a small capacity image filing apparatus, FIG. 16 is a flowchart which shows the process in the ID mode shown in the state transition drawing in FIG. 15, FIG. 17 is an explanatory view which shows the recorded data contents such as ID data and so on, which are provided in the RAM of a small capacity image filing apparatus, FIGS. 18 and 19 are flowcharts which respectively show the processes in the examination mode and the release mode shown in the state transition drawing in FIG. 15, FIGS. 20a 20b, ... 20g are flowcharts which show the process in the search mode shown in the state transition drawing in FIG. 15, FIG. 21 is a flowchart which shows the process in the image registering mode shown in the state transition drawing in FIG. 15, FIG. 22 is a state transition drawing which shows transition between respective operation modes in an image file interface section, FIG. 23 is an explanatory view which shows a queue table in which job contents for processing are stored, FIG. 24 is a flowchart which shows the process in an initialization mode and a STAND-BY mode, FIGS. 26 and 27 are flowcharts which respectively show the processes in an image registering mode and a queue update mode, FIG. 28 is a flowchart which shows the process in an interrupt processing mode, FIG. 29 is a state transition drawing which shows transition states between respective operation modes of a large capacity image filing apparatus, FIGS. 30 to 32 are flowcharts which respectively show the processes in an ID input mode, an examination mode and a release mode.

FIGS. 35 and 36 relate to a second embodiment of the present invention in which FIG. 35 is a perspective view of an image input/filing apparatus in a modification of the first embodiment of the present invention and FIG. 36 is a drawing of the configuration a scope with an external television camera;

FIGS. 37 and 38 relate to the second embodiment of the present invention in which FIG. 37 is a block diagram of the configuration of a small capacity image filing apparatus in the second embodiment and FIG. 38 is block diagram of the configuration of an image file interface apparatus;

FIGS. 40 and 41 relate to a third embodiment of the present invention in which FIG. 40 is a block diagram of the configuration of an image file interface apparatus in the third embodiment and FIG. 41 is a block diagram of the configuration of a large capacity image filling apparatus;

FIG. 41 and 43 relate to the third embodiment of the present invention in which FIG. 42 is a block diagram of the configuration of a small capacity image filing apparatus and FIG. 43 is a schematic block diagram of the configuration of an image interface apparatus and a large capacity image filing apparatus;

FIGS. 45 to 47 relate to a fifth embodiment of the present invention in which FIG. 45 is a perspective view of an image filing apparatus in the fifth embodiment, FIG. 46 is a block diagram of the configuration of an image input apparatus in the fifth embodiment and FIG. 47 is a block diagram of the configuration of an image file interface section;

FIGS. 48 to 50 relate to a sixth embodiment of the present invention in which FIG. 48 is a perspective view of the overall configuration of the sixth embodiment, FIG. 49 is a block diagram of the configuration of a multi-image display interface and FIG. 50 is a drawing of the state in which multiple images are displayed on a color monitor;

FIGS. 51 and 52 related to a seventh embodiment of the present invention in which FIG. 51 is a drawing of the overall configuration of the seventh embodiment and FIG. 52 is a block diagram of the configuration of an ultrasonic scope and so on;

DETAILED DESCRIPTION OF PREFERRED EMBODIMENTS

Figure 5:
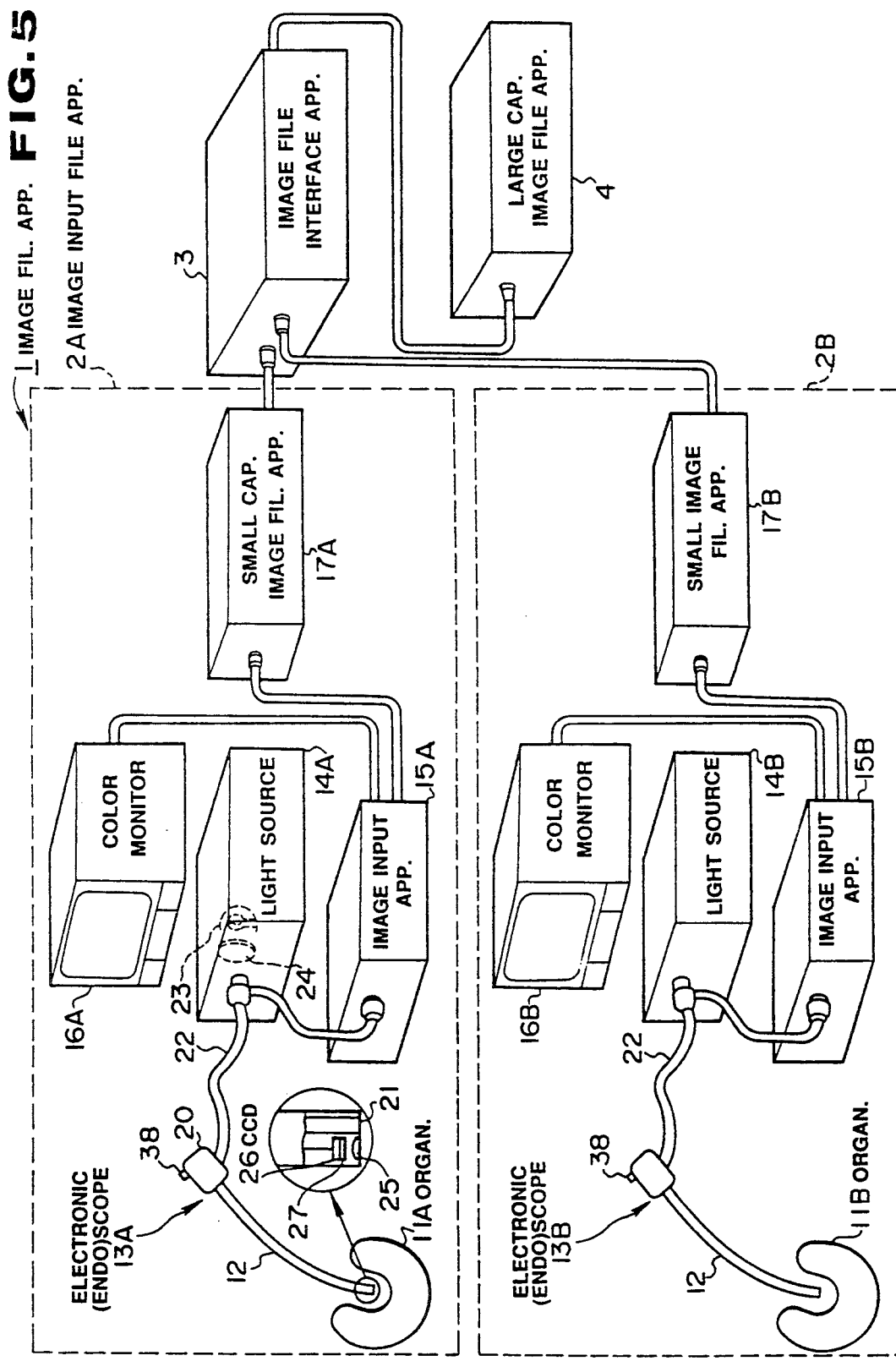

As shown in FIG. 5, an image filing apparatus 1 of a first embodiment comprises an image file interface apparatus 3 to which a plurality of image input/filing apparatuses 2A, 2B ... (represented by 2I hereinafter wherein I=A, B, ... ) are connected for successively transmitting examination images for a single examination; and a large capacity image filing apparatus 4 which is connected to the image file interface apparatus (referred to as "an image FIG apparatus" hereinafter) 3 and which serves to record, search for, regenerate and output image data sent and data information thereof.

Each image input/filing apparatus 2I comprises an electronic scope 13I having an insertion portion 12 which is inserted into an organ 11I or the like, a light source 14I for supplying illumination light to the electronic scope 13I, an image input apparatus 15I for processing signals obtained from imaging by the electronic scope 13I and for generating given video signals, a color monitor 16I for displaying the given video signals output from the image input apparatus 15I and a small capacity image filing apparatus 17I provided with a plurality of frame memory means for temporarily storing the video signals.

Figure 6:
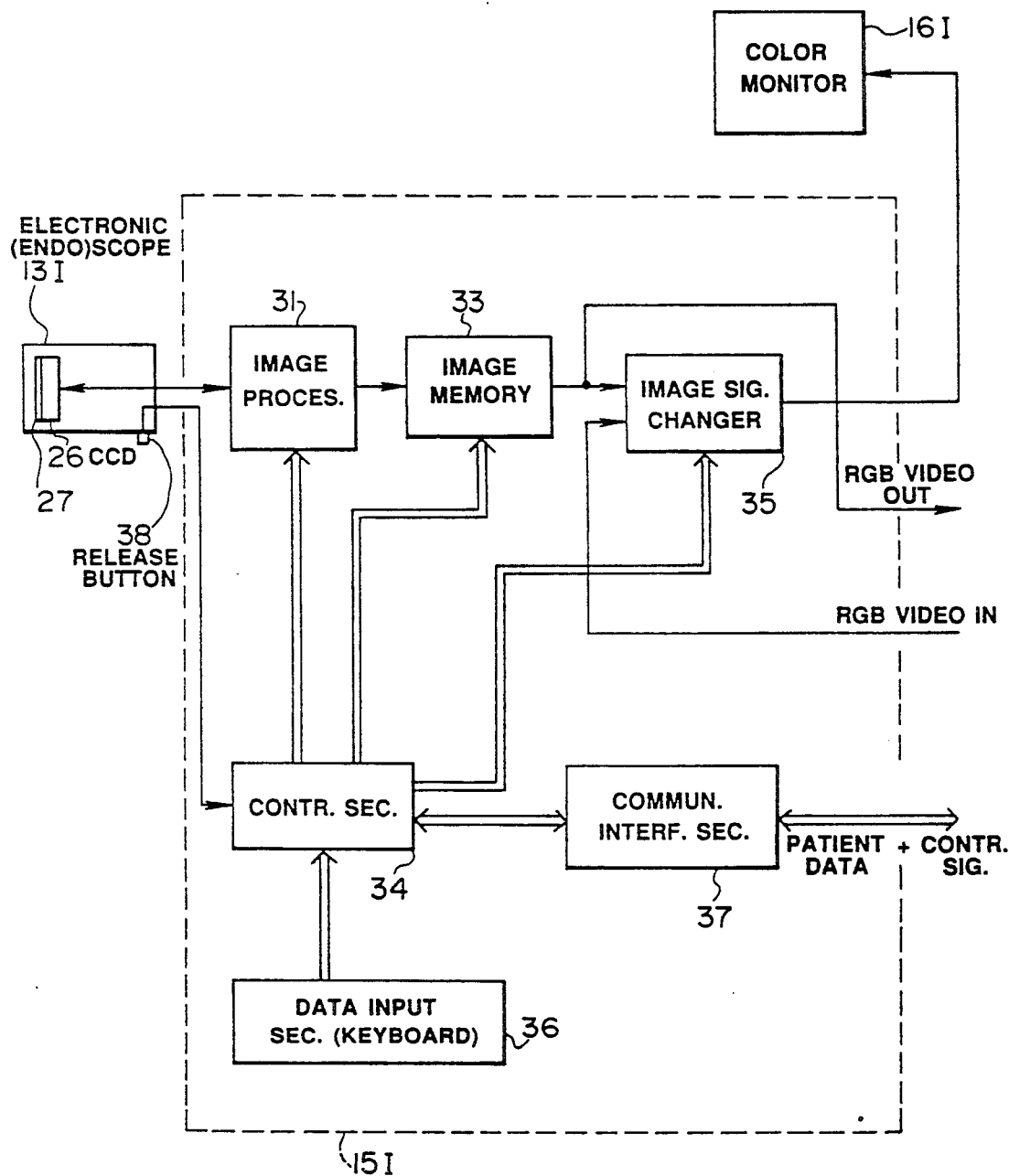

In each electronic scope 13I, a light guide 21 for transmitting illumination light is passed through the long thin insertion portion 12 having an incident end side passed through a universal code 22 extended from an operational portion 20 so that it can be connected to the light source 14I. Thus, illumination light is supplied to each electronic scope 13I from a lamp 23 through a capacitor lens 24 in the light source 14I. The interior of the organ 11I is illuminated with light which is emitted from an emission end through the light guide 21. An image of the interior of the organ 11I is formed on CCD 26 disposed at the focal surface of an objective lens 25 which is provided at an end of the insertion portion 12. A mosaic color filter 27 is provided on the image surface of the CCD 26 for the purpose of separating colors in in pixel. As shown in FIG. 6, signal charge, which was subjected to photoelectric conversion and accumulated by the drive signal output from the drive circuit (not shown) in an image processing section 31 of each image input apparatus 15I, is read as a video signal and input to a signal processing circuit (not shown) in the image processing section 31. In the case of a normal video signal, it is converted into an RGB video signal and then output to an image memory 33. The image processing section 31 has the function of controlling the level of an image signal, i.e., the balance (white balance) between the G signal and the R and B signals. The image processing section 31 also has the function of displaying information such as patient data, an error message and so on, which are all transmitted from a control section 34 and superimposed on the RGB video signals.

The above-described image memory 33 has the function of outputting an image without any change formed by writing the RGB video signals input from the image processing section 31 in correspondence with the control signal output from the control section 34 and for outputting the signal of a still picture to an image signal switch 35 and each external small capacity image filing apparatus 17I when writing is temporarily inhibited. The image signal switch 35 is switched by the control signal output from the control section 34 so as to output to each color monitor 16I signals transmitted from the image memory 33 or the RGB video signals transmitted from each external small capacity image filing apparatus 17I. To the control section 34 are input signals from a data input section 36 comprising a keyboard or the like and a communication interface section 37 so that each section of each image input apparatus 15I is controlled in accordance with the predetermined program described below.

The above-described data input section 36 is used for input data such as patient names, the dates of birth of patients and so on which are superimposed on the RGB signals output, by the user operating the keyboard and for inputting controls of image recording (release), image search and so on.

The communication interface section 37 is, for example, an interface section for serial transfer on the RS-232C standard and has the function of inputting and outputting data from and to the external small capacity image filing apparatus 17I by the control from the control section 34.

Each electronic scope 13I has a release button 38 provided, for example, in the operational portion so that a release signal is input to the control section 34 of the image input apparatus 15I when the release button 38 is pushed. The control section 34 is therefore capable of outputting a signal for controlling the image memory 33 to a frozen image when the release signal is input thereto, as well as sending a release signal to the external small capacity image filing apparatus 17I through the communication interface section 37. A release operation can be performed by using each image input apparatus 15I.

Figure 7:
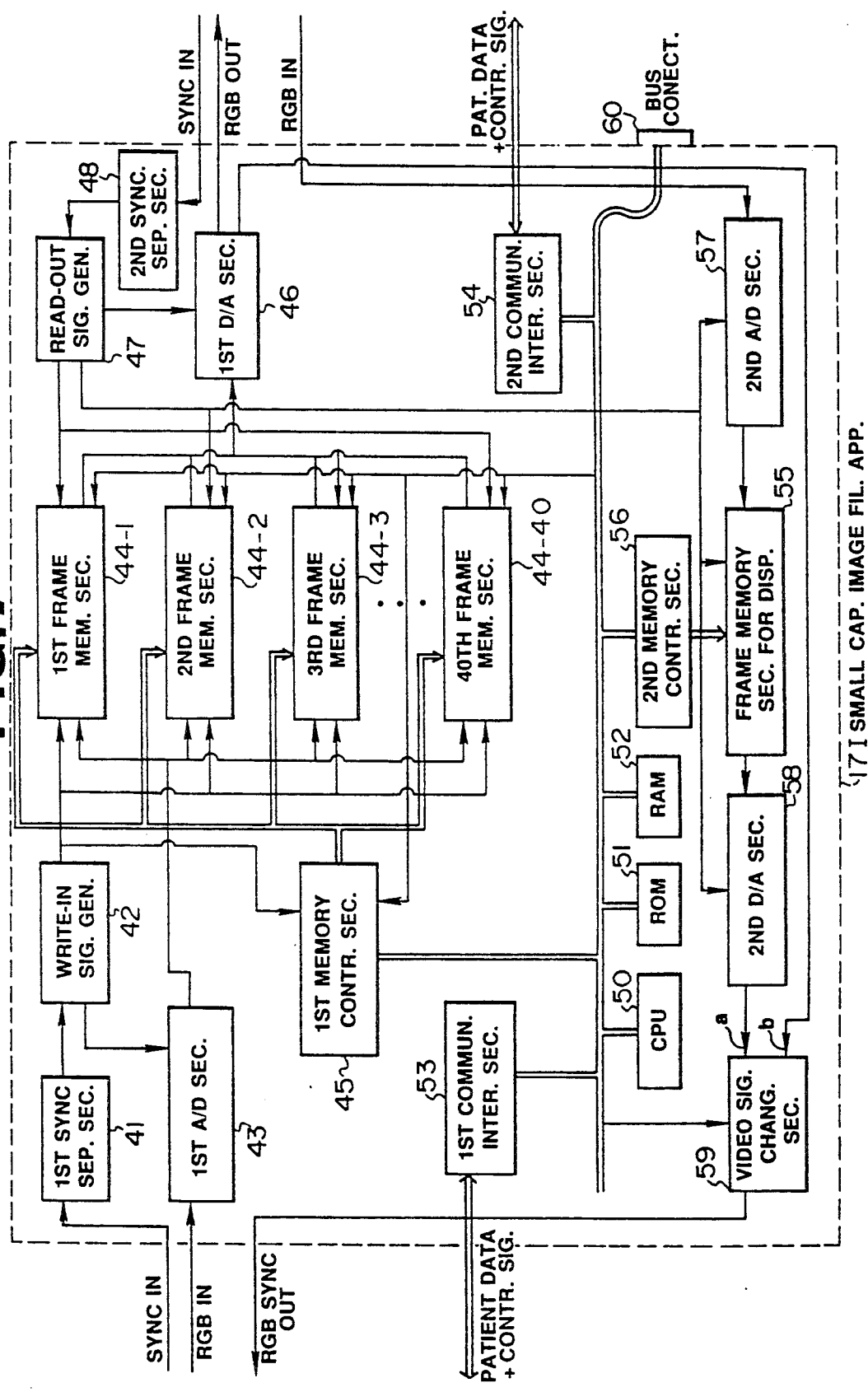

FIG. 7 shows the configuration of each small capacity image filing apparatus 17I.

Synchronous(SYNC) signals which form the RGB signals output from each image input apparatus 15I are input to a first synchronizing separation section 41 in which the composite SYNC signals are separated into vertical and horizontal synchronous signals which are then output to a write signal generating section 42.

The RGB signals are also input to a first A/D conversion section (referred to as A/D section) 43 so as to be converted into digital signals which are then input to first, second, third, . . . 40th frame memories 44-1, 44-2, 44-3, . . . 44-40.

The above-described write signal generating section 42 generates standard clocks for sampling of A/D conversion from the vertical and horizontal synchronous signals which are separated and for writing the signals in each of the frame memory sections 44-i (i=1, 2, . . . 40) and a timing signal for indicating the times of start and end of writing in each of the frame memory sections 44-i. The timing signal is output to a first memory control section 45 for selecting one of the frame memory sections 44-i and controlling write and read. The first A/D section 43 converts the RGB input analogue signals into, for example, by 8 bits, on the basis of the standard clock from the write signal generating section 42. In other words, the first A/D section comprises 3 A/D converters, the output thereof can be input to each of the frame memory sections 44-i. The image data written in each of the frame memory sections 44-i is converted into analogue signals by a first D/A conversion section (referred to as "D/A section" hereinafter) 46 and is output to the side of the image FIF apparatus 3 from the RGB output side thereof. The first D/A section 46 performs D/A conversion of the digital image data in accordance with a standard clock. The first D/A section 46 also comprises three D/A converter for D/A conversion of R, G, and B signals.

The image data is read from each of the frame memory sections 44-i by using the clock output from a read signal generating section 47. The read clock is generated on the basis of the vertical and horizontal synchronous signals produced by separating the composite synchronous signal from the common image FIF apparatus 3 in a second synchronizing separation section 48.

The writing in each of the frame memory sections 44-i is effected by using the clock generated from the write signal generating section 42, and the reading is effected by using the read clock which is generated by the synchronous signals from the common image FIF apparatus 3 separately from the write clock. In this way, each of the frame memory sections 44-i has a dual port structure for separately writing and reading data.

Each of the frame memory sections 44-i also has a memory capacity sufficient to store the digital image data for one frame of RGB signal data so that, when write is selected by the first memory control section 45, the write of the digital image data input from the first A/D section 43 is started in accordance with the timing signal input from the write signal generating section 42. The write is successively effected on the basis of the standard clock input from the write signal generating section 42. When the read is selected by the first memory control section 45, the read is successively repeated on the basis of the standard clock and the timing signal input from the read signal generating section 47.

Each of the small capacity image filing apparatuses 17I has 40 frame memory sections 44-i which have the same configuration and are provided in a line so that image record for a single examination can be covered.

Each of the small capacity image filing apparatuses 17I also contains CPU 50 for controlling each of the sections of each small capacity image filing apparatus 17I by using a working RAM 52 in accordance with the program of a program ROM 51.

The CPU 50 is connected to first and second communication interface sections 53, 54 through a bus line, as well as being connected to a second memory control section 56 for controlling a display frame memory section 56.

The above-described first communication interface section 53 is connected to a communication interface section 37 of the image input apparatus 15I through a communication line for serial input and output, for example, on the RS-232C standard. The second communication interface section 54 is provided for serial input and output, for example, on the RS-232C standard, and connected to the image FIF apparatus 3. Therefore, patient data and control signals can be transmitted by each of the communication interface sections 53, 54 so that data and control signals can be transmitted on the basis of the control by the CPU 50.

The first memory control section 45 is connected to the CPU 50 through a bus line so as to select one of the frame memory sections 44-1 to 44-40 and send control signals of write and read thereto on the basis of the control signals from the CPU 50.

The second memory control section also sends control signals of write in and read from the display frame memory section 55 by using the control signals from the CPU 50.

In the display frame memory section 55 is written the RGB signals from the image FIF apparatus 3 which are converted into digital signals by the second A/D section 57. The digital image data written in the frame memory section 55 is converted into analogue RGB signals by the second D/A section 58 and is input to a video signal switching section 59.

The second A/D section 57, the frame memory section 55 and the second D/A section 58 respectively perform the A/D conversion, the write and read and the D/A conversion by using the standard clock from the read signal generating section 47.

To the video signal switching section 59 is also input the RGB signals output from the first D/A section 46, the signal either of the first or second D/A section 46 or 58 being output from the switching section 59. The output signal from the video signal switching section 59 is input to each image input apparatus 15I from the RGB video output terminal thereof. In this case, when the image signal switch 35 of each image input apparatus 15I is switched to the external input side, the RGB video signals on the external input side are displayed on the color monitor 16I.

The bus line of the CPU 50 is connected to a bus connector 60.

Figure 8:
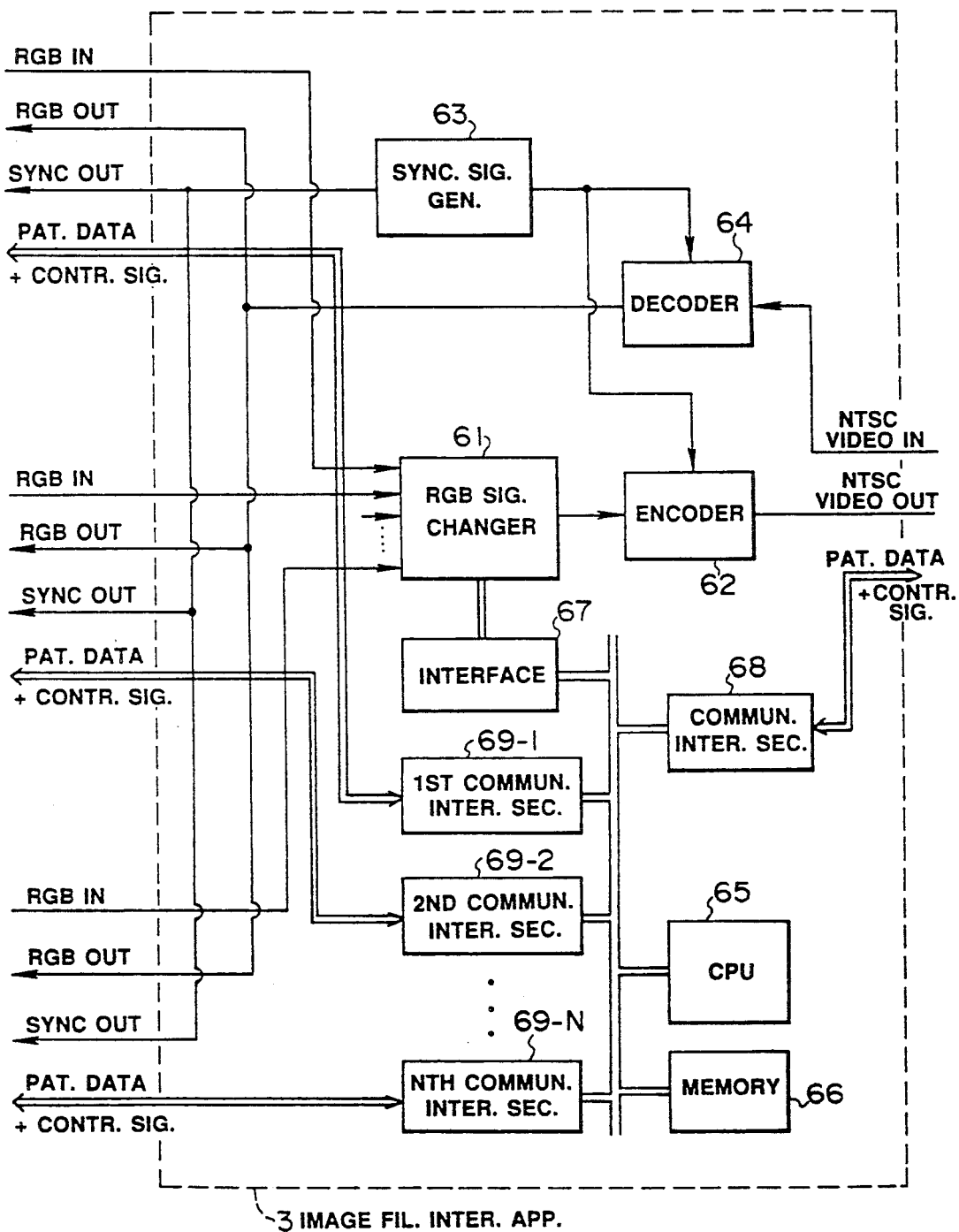

FIG. 8 shows the configuration of the image FIF apparatus 3 to which the small capacity image filing apparatuses 17I are connected.

The RGB video signals output from each small capacity image filing apparatus 17I are input to an RGB signal switch 61, and one RGB video signal selected is input to an encoder 62 in the next stage. The synchronous signal from a synchronous signal generator 63 is mixed with the video signal input to form an NTSC composite video signal which is then output to an external large capacity image filing apparatus 4. Sine each of the RGB video signals input to the RGB signal switch 61 has the read clock for the frame memory sections 44-i which is formed on the basis of the synchronous signal output from the synchronous signal generator 63, each video signal synchronizes with the synchronous signal from the synchronous signal generator 63.

The NTSC composite video signals output from the large capacity image filing apparatus 4 are input to a decoder 64, converted into RGB video signals by using the synchronous signal from the synchronous signal generator 63 and then output to each small capacity image filing apparatus 17I.

The image FIF apparatus 3 contains CPU 65 and a program and working memory 66 so as to control the switching of the RGB signal switch 61 through an interface 67. The image FIF apparatus 3 also controls the sending and reception of patient data and control signals to and from the large capacity image filing apparatus 4 through a communication interface section 68. In addition, the image FIF apparatus has first, second, . . . Nth communication interface sections (serial port) 69-1, 69-2, . . . 69-N, which are respectively connected to the small capacity image filing apparatuses 17I through communication lines so as to control the sending and reception of the patient data and the control signals to and from the respective small capacity image filing apparatuses 17I. The image FIF apparatus 3 forms interface means which is interposed between each of the image input apparatuses 15I and the large capacity image filing apparatus 4 through a plurality of small capacity image filing apparatuses 17I so as to enable the image input apparatuses 15I to use the large capacity image filing apparatus 4 in common.

Figure 9:
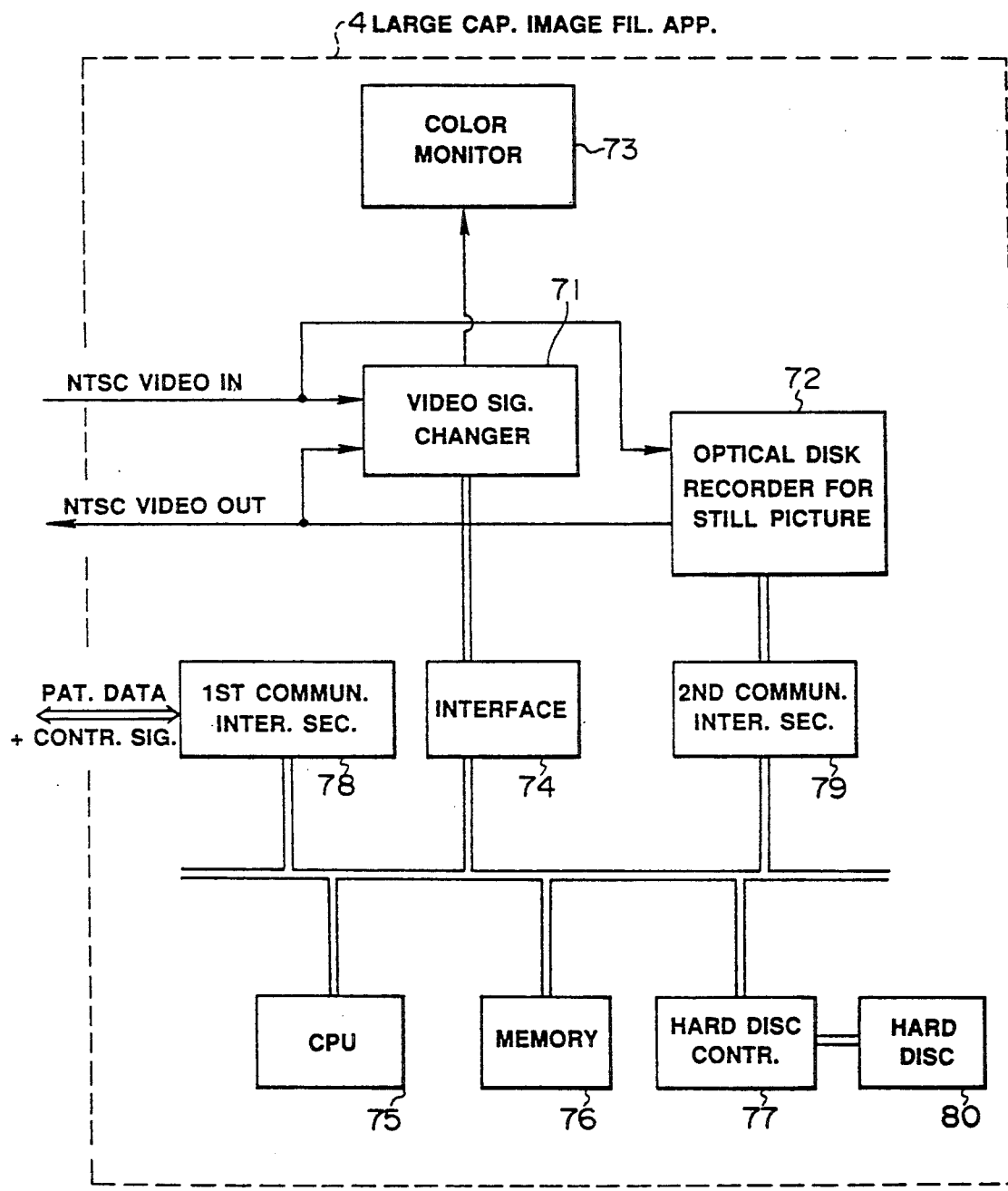

FIG. 9 shows the configuration of the large capacity image filing apparatus 4 connected to the image FIF apparatus 3.

The NTSC video signals output from the image FIF apparatus 3 are input to a video signal switch 71, as well as being input to a still picture recording optical disk recorder (referred to as "optical disk recorder" hereinafter) 72 in which image data is recorded. The optical disk recorder 72 serves to read the image data recorded and output as NTSC video signals during search. The NTSC video signals output from the optical disk recorder 72 are thus output to the video signal switch 71, as well as being output to the image FIF apparatus 3. The video signal switch 71 selects one of the two video signals input thereto and outputs it to a color monitor 73 on which the video signal switched is color-displayed.

The video signal switch 71 is operated under the control from CPU 75 through an interface 74. The CPU 75 is connected to a memory 76 and a hard disk controller 77 through a bus line, as well as being connected to a first communication interface section 78, which is connected to the image FIF apparatus 3, and to a second communication interface section 79, which is connected to the optical disk recorder 72, through a communication line. The CPU 75 therefore performs the control of patient data and control signals send and received through the first communication interface section 78, the control of recording in and regeneration from the optical disk recorder 72, and the control of recording and searching in a database by the control of a hard disk 80 through the hard disk controller 77. The patient data such as ID of patients and the information of image data recorded on the optical recorder 72 are registered in a database of the hard disk 80.

The first and second communication interface sections 78, 79 serve to send and receive serial data, for example, on the RS-232C standard.

The operation in the above-described configuration will described below.

Figure 10:
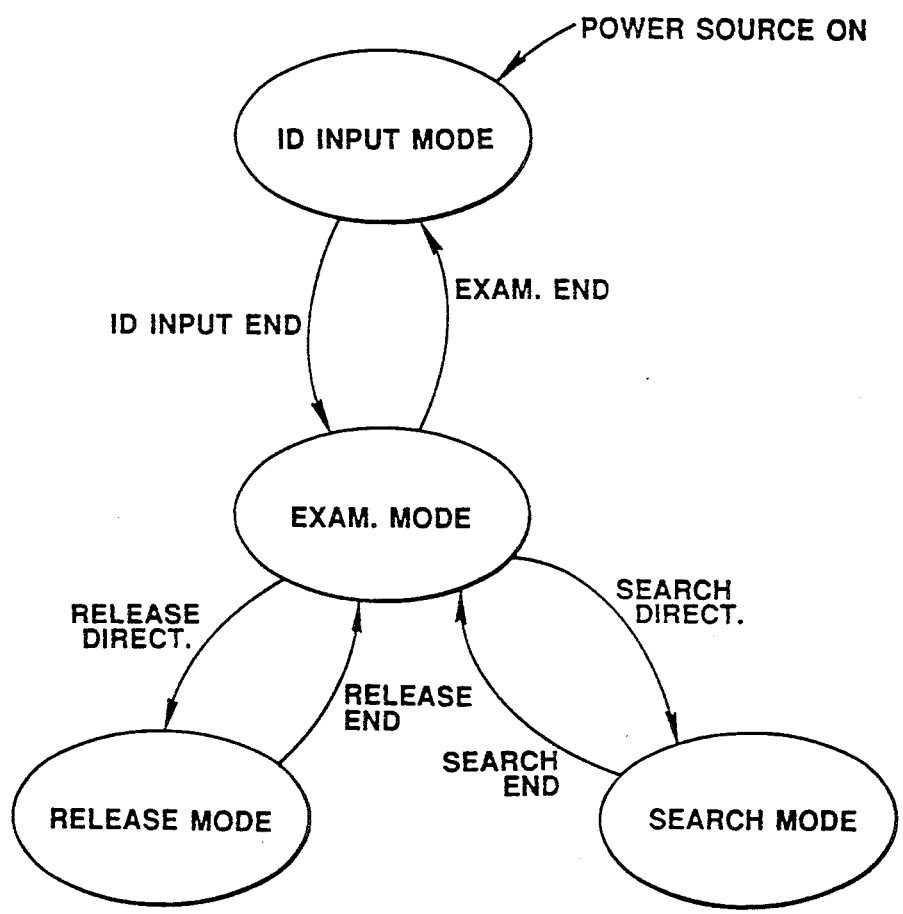

FIG. 10 is a state transition drawing which shows the control state of the control section 34 in each image input apparatus 15I.

After the power source has been turned on, the control state of the control section 34 is brought into an ID input mode. When the ID of a patient is input, the ID mode is moved to an examination mode. This examination mode is a mode for displaying the image obtained by imaging by each electronic scope 13I on the color monitor 16I thereof. The examination mode is moved to a release mode when a release operation is performed. This release mode is a mode for imaging in a state wherein the image is frozen.

When a search direction is given in the above-described examination mode, the examination mode is moved to search mode. The search mode is mode for searching for an image which has been previously recorded.

When either of the release mode or the search mode is completed, the mode is again moved to the examination mode. The examination mode is returned to the ID mode when a direction of examination end is given.

The processes in these modes will be described below in turn.

FIG. 12 is a flowchart which shows the operation in the ID mode. Initialization is carried out when a power source is turned on. In the initialization, the adjustable value of the signal level of the image processing section 31 shown in FIG. 6 is set to an initial value, and the image signal switch 35 is switched to the internal signal side so that the signal output from the image memory 33 is selected. At the same time, the image of a diseased part or the like, which is illuminated by the illumination light from each light source 14I, is formed on the CCD 26 of each electronic scope 13I and then converted into electrical signals by photoelectric conversion. The the electrical signals are read by applying a drive signal and converted into video signals by processing in the signal processing system of the image processing section 31. The video signals are then output to the small capacity image filing apparatus 17I from the RGB video output terminal, as well as being output to the color monitor 16I through the image signal switch 35.

Figure 11:
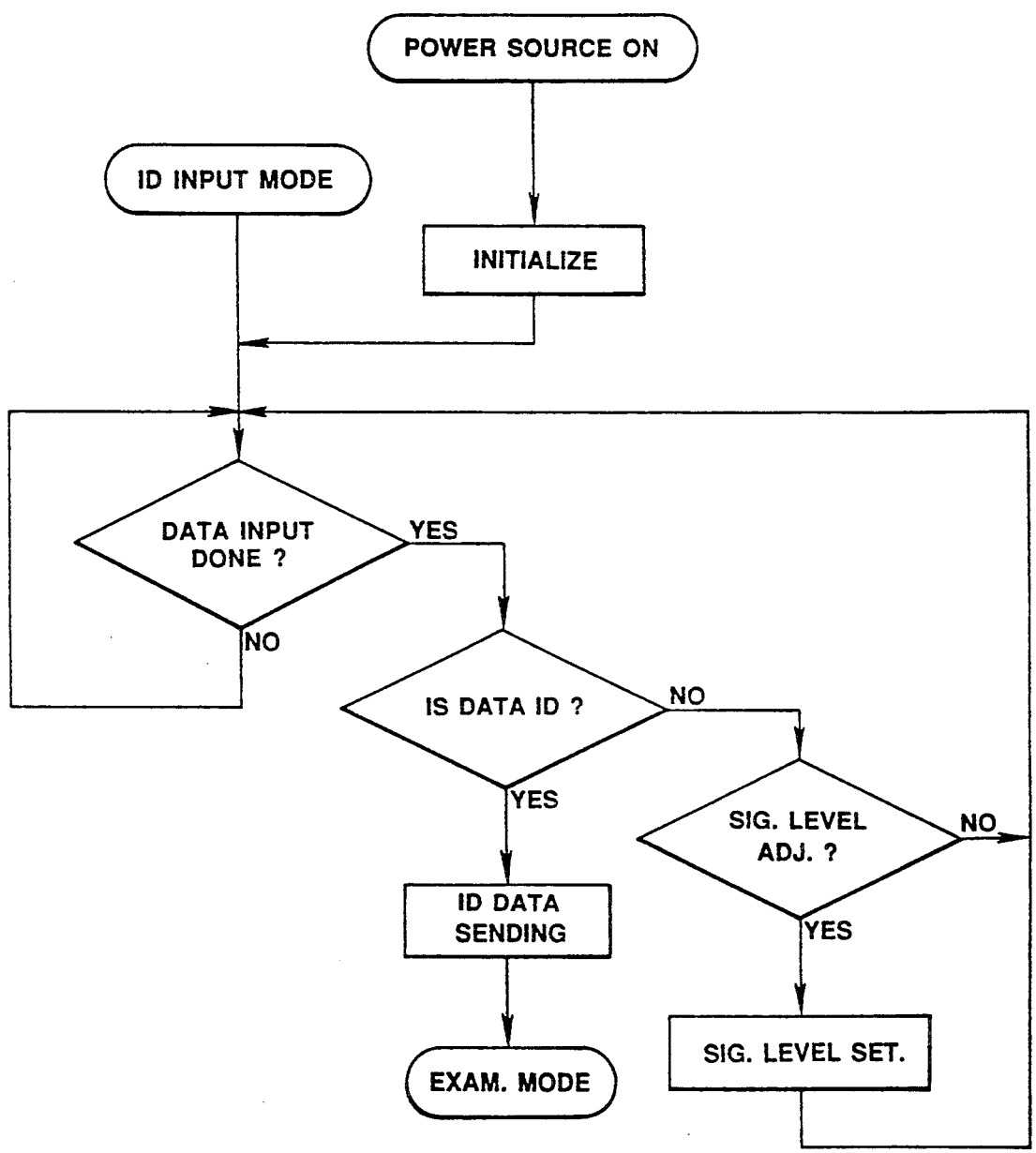

In FIG. 11, after the initialization, a check is made as to whether oar not data is input. If no data is input, the check is repeated, and the state of each of the sections remains unchanged. If it is decided that data is input from the data input section 36, the contents of the data are checked. When the data is ID data, the ID data is transmitted to the small capacity image filing apparatus 17I through the communication interface section 37, followed by transition to the examination mode shown in FIG. 10 or 12. When the input data is not ID data, a check is made as to whether or not the input data is directive data for adjustment of the signal level. If the data is directive data for adjustment of the signal level, a control signal is output to the image processing section 31 so that the signal level is adjusted to an indicated value, while if the input data is not directive data, the process is returned to the operation of checking whether or not data is input.

FIG. 12 is a flowchart which shows the operation in the examination mode. In the examination mode, a check is made whether or not data is input, the check being repeated until data is input. When data is input, therefore, the check and the operations described below are performed in turn.

If the content of the input data is a direction of examination end, a message of examination end is transmitted through the communication interface section 37, and the mode is moved to the ID input mode.

If the content of the input data is not a direction of examination end but a direction of release, the examination mode is moved to the release mode shown in FIG. 10 or 13. If the content is not a release direction but a search direction, the mode is moved to the search mode shown in FIG. 14. If the content is a direction of adjustment of the signal level, a control signal is output to the image Processing section 31 so that the signal level is adjusted to an indicated value, and then the process is returned to the check on the presence of data input.

When the input data is patient data, the data is output to the image processing section 31, superimposed and displayed on the color monitor 16I and transmitted through the communication interface section 37, and the process is returned to the check on the presence of data input.

When the input data comes under none of the above-mentioned cases, the process is returned to the check on data input without any other processing.

FIG. 13 is a flowchart which shows the operation in the release mode.

In the release mode, a control signal for freezing an image is first output to the image memory 33, and then a prompting message for release is transmitted to the external small capacity image filing apparatus 17I through the communication interface section 37. A check is then made as to whether or not the communication interface section 37 receives a message from the outside thereof, the check being repeated until it receives the message. When the interface section 37 receives the message, a check is made as to whether or not the message is a message of normal end of the release. If the message received is not such a message, an error message is sent to the image processing section 31 and displayed in a superimposition state. In the case of normal end, a control signal for release of freezing is output to the image memory. The release mode is then returned to the examination mode. The small capacity image filing apparatus 17I performs the operation of storing the frozen image in the frame memory section 44-i when the lease prompting message is transmitted.

Figure 14A:
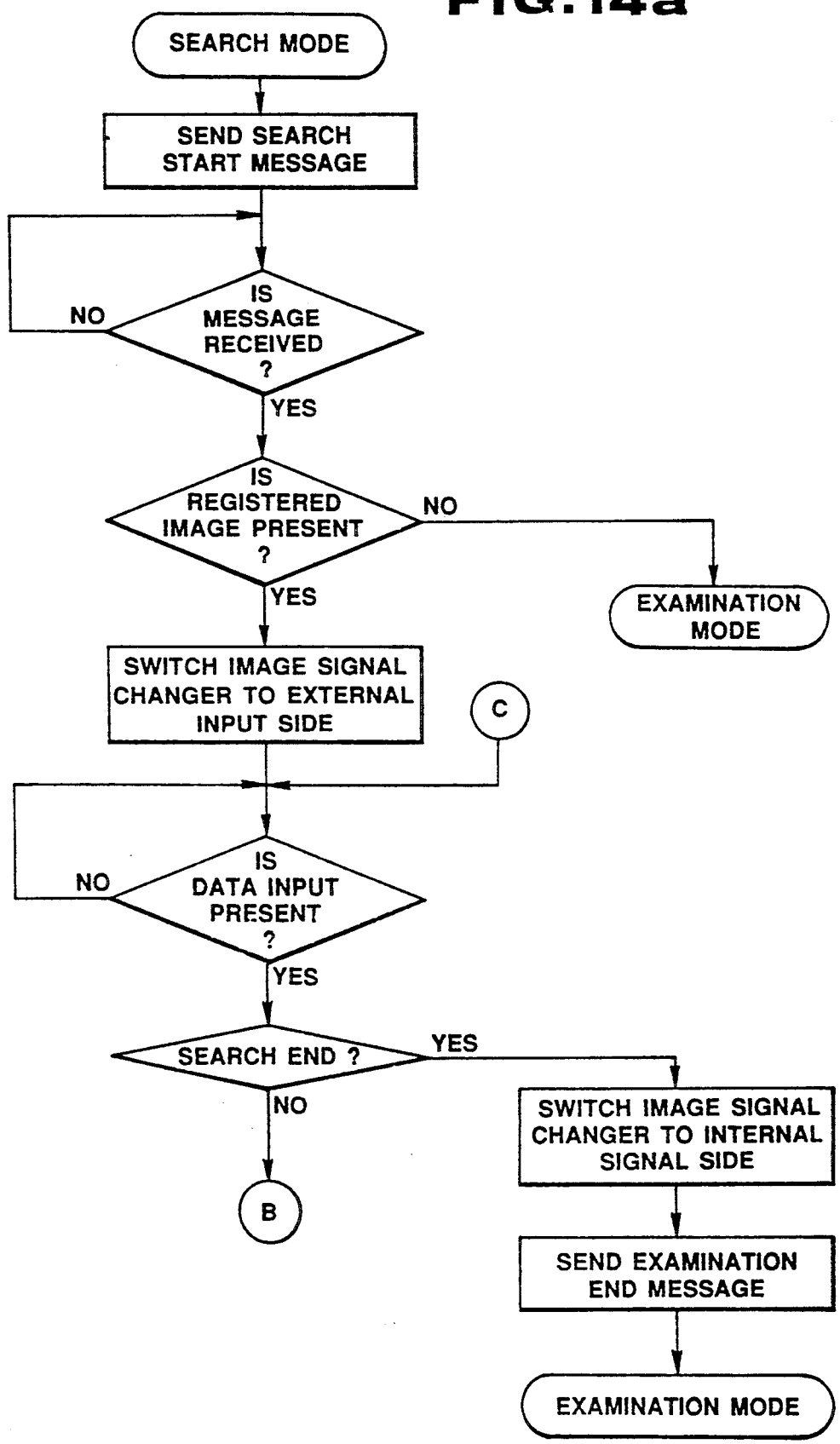
Figure 14B:
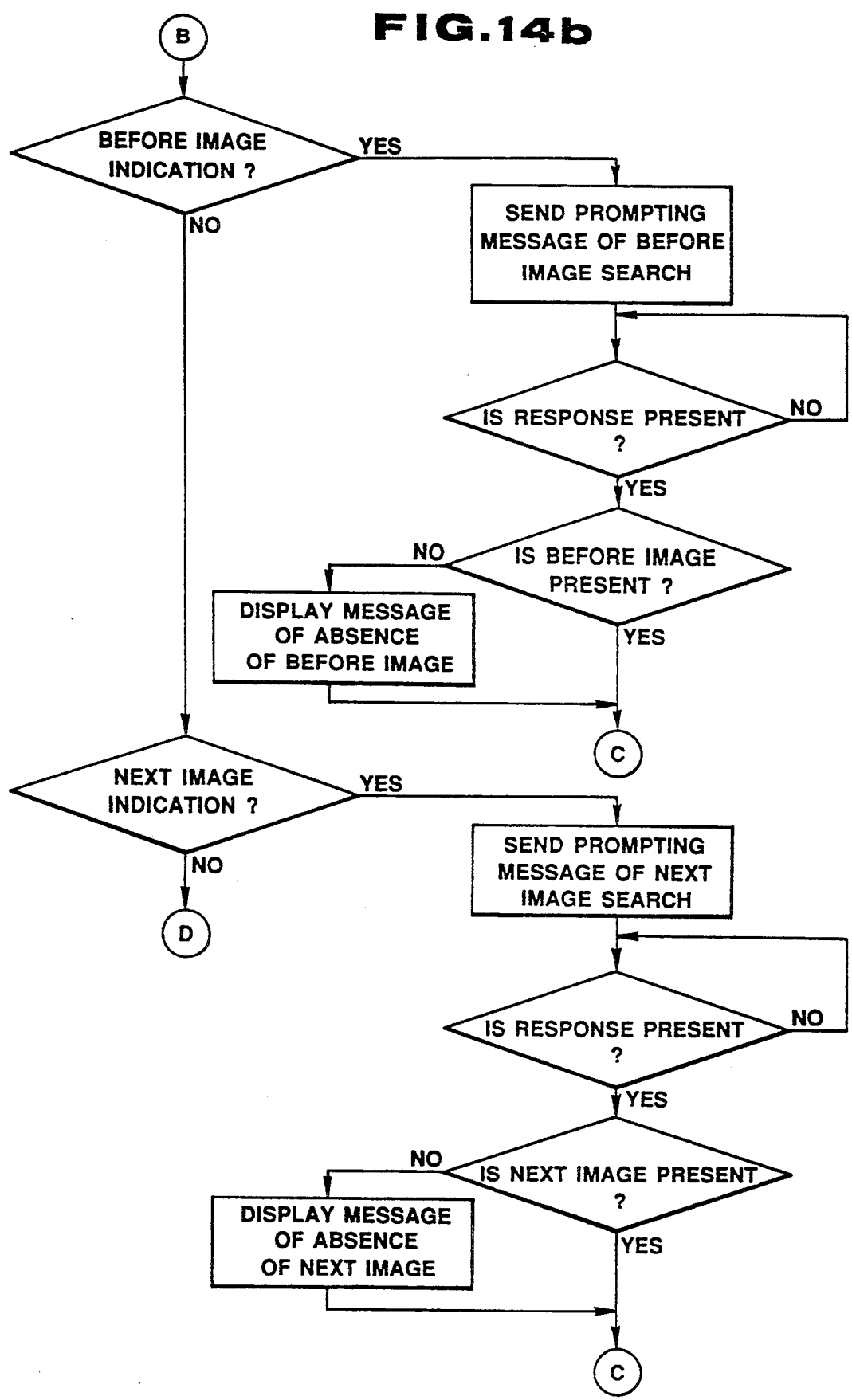
Figure 14C:
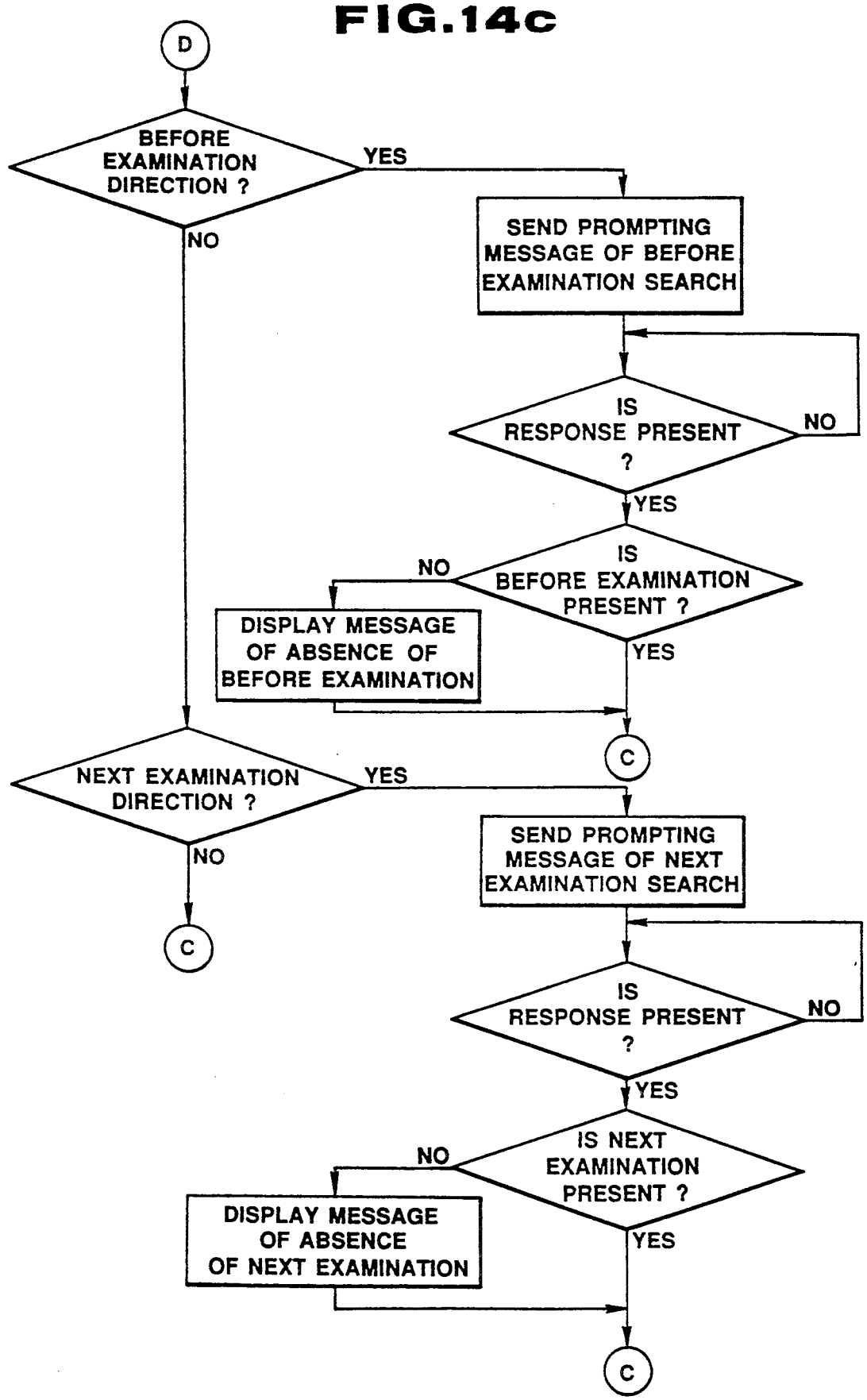

FIGS. 14a, 14b, 14c are flowcharts which show the operation in the search mode.

In the search mode, a search start message is transmitted through the communication interface section 37, which then waits for the reception of a message. If the message received indicates that there is no registered image, the search mode returns to the examination mode. When there is registered images, a control signal is output so that the image signal switch 35 is switched to the external input side so that a check on data input is then started. The switching causes the signal from the small capacity image filing apparatus 17I to be displayed on the color monitor 16I.

A check is made as to whether or not the input data indicates search end. When it is decided that the search is completed, a control signal for switching the image signal switch 35 to the internal signal side, and a search end message is then sent so that the search mode is moved to the examination mode.

Figure 4:
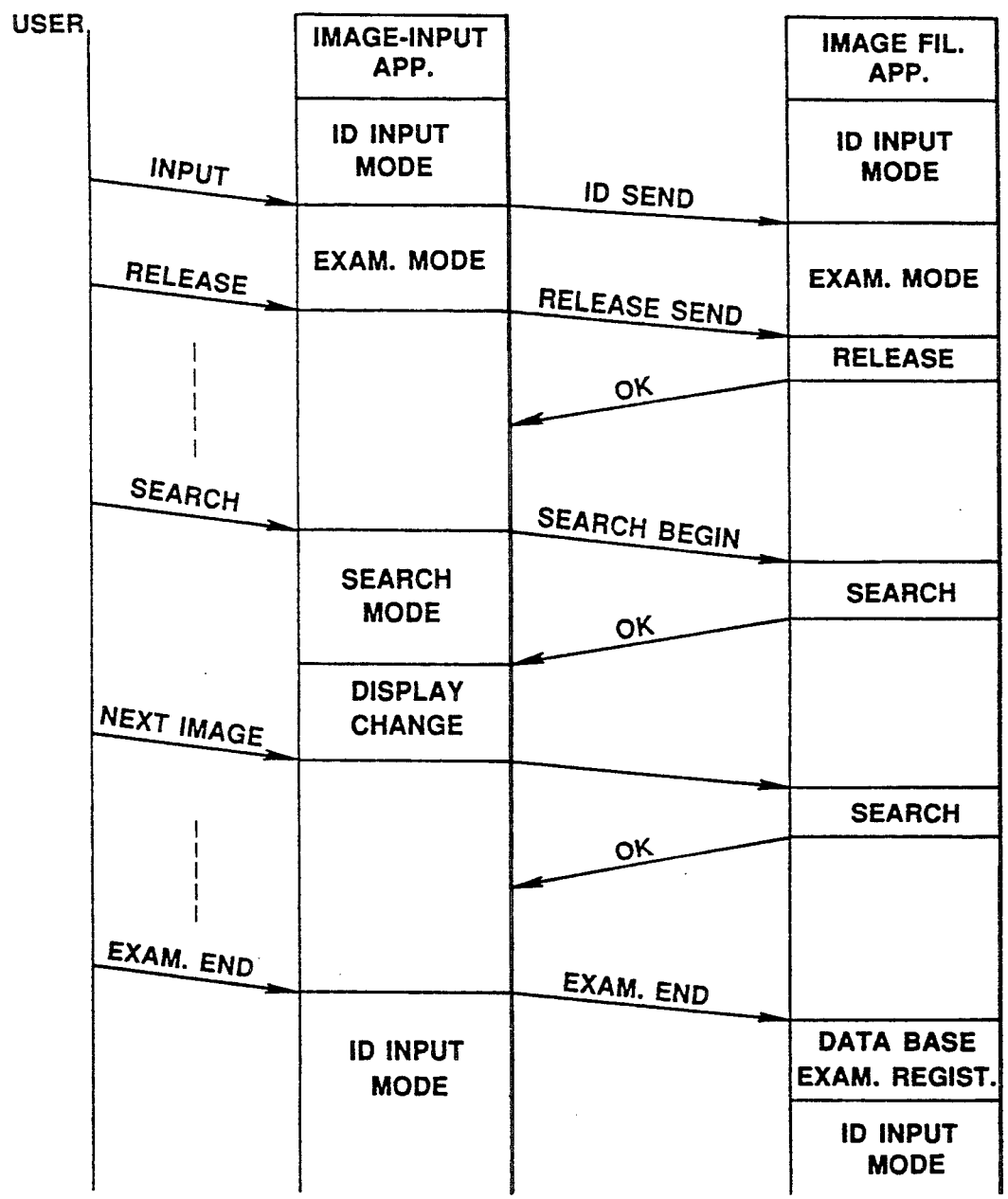

While, when it is decided that the search is not completed, a check is made as to whether or not the input data shows a direction of the before image, as shown in FIG. 4b. When it is decided that the data shows a direction of the before image, a image search prompting message is transmitted through the communication interface section 37, which then waits for a reply thereto. If there is a reply, a decision is made as to whether or not the reply is a message of the presence of the before image. When there is the before image, a state wherein data input is waited for is created. While if there is no before image, a control signal for causing the display of a message of the absence of the before image is output to the image processing section 31, and then data input is waited for.

When it is decided that the data does not show a direction of the before image, a check is made as to whether or not the data shows a direction of the next image. The processes after such a check are the same as in the case of the before image and are thus not described below.

The before (next) image represents the image before (next) the image which is presently searched or displayed in the examination involving the image.

When it is decided that the data does not show a direction of the next image, a decision is made as to whether or not the data shows a direction of the before examination, as shown in FIG. 14c. When it is decided that the data does not show a direction of the before examination, a check is made as to whether or not the data shows a direction of the next examination. The processes after these checks on the directions of the before and next examinations are the same as those described above and are thus not described below. The before (next) examination represents the examination before (next) the examination which involves the image that is presently searched or displayed.

A description will now be given of the operation of each small capacity image filing apparatus 17I for inputting and outputting the RGB video signals from and to each image input apparatus 15I and sending the patient data and control signals with reference to FIGS. 15 to 21.

Figure 15:
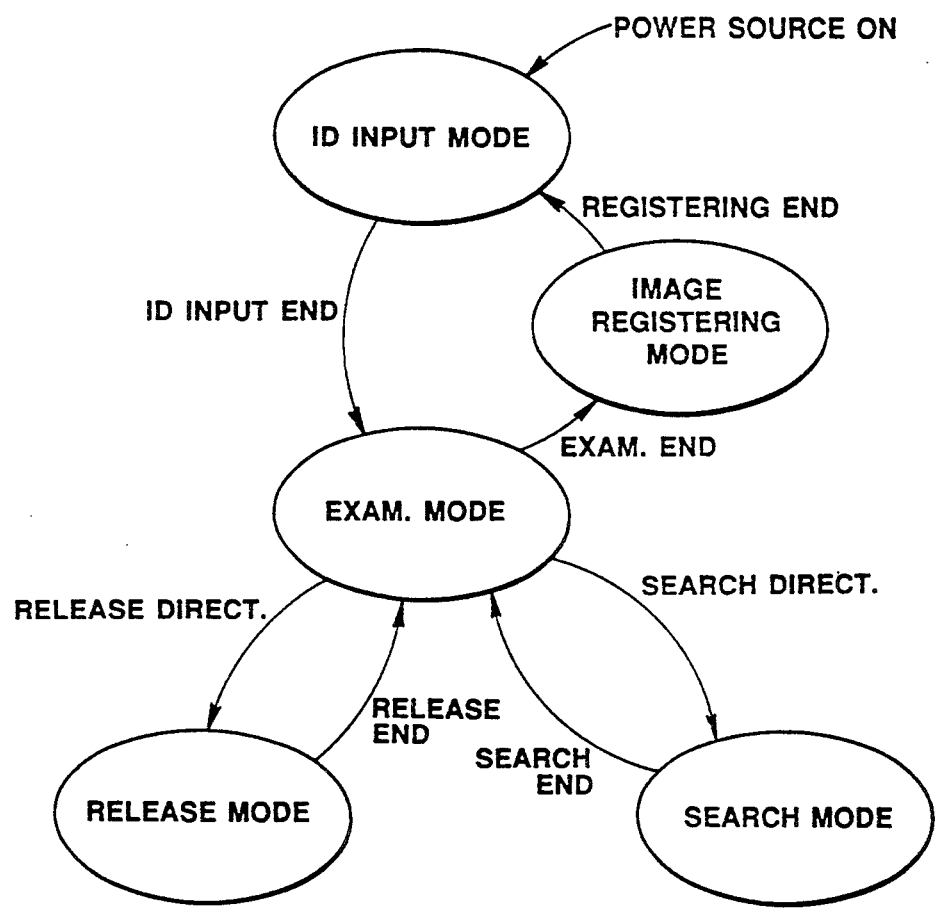

FIG. 15 is a state transition drawing which shows the states in a plurality of operation modes of each small capacity image filing apparatus and which corresponds to the state transition drawing in the image input apparatus shown in FIG. 10. In FIG. 15, however, the examination mode is moved to an image registering mode before it is moved to the ID input mode by a direction of examination end. In the image registering mode, the image data for a single examination which is stored in the frame memory sections 44-1, 44-2, ... in each small capacity image filing apparatus 17I and the image information thereof are registered (recorded) in the large capacity image filing apparatus 4 through the image FIF apparatus 3. The image registering mode is then moved to the ID input mode.

A description will now be given of the operation in each of the modes.

Figure 16:
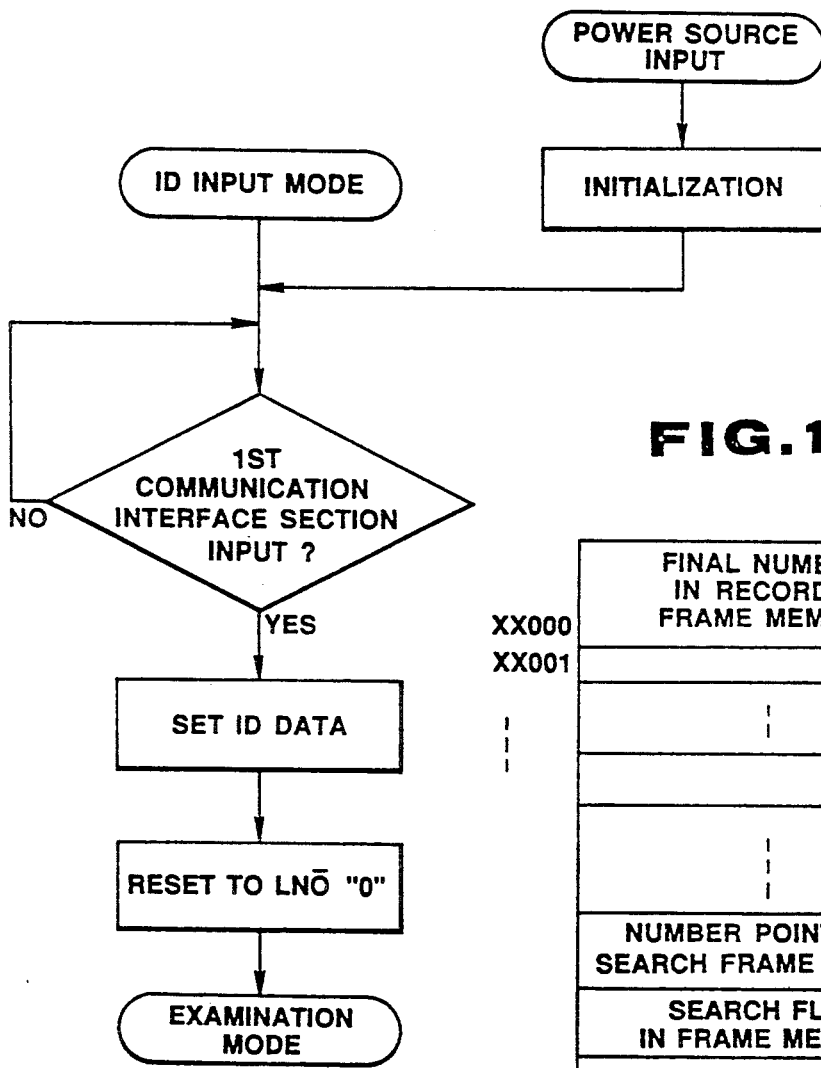

FIG. 16 shows the operation in the ID input mode.

Figure 17:
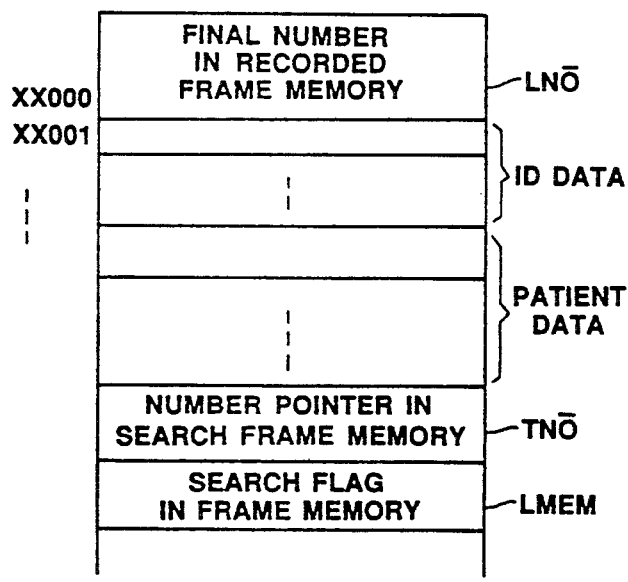

The initialization is effected by turning the power source on to bring about the ID input mode. In the ID input mode, input of data in the first communication interface section 53 shown in FIG. 7 is waited for. In this case, since the input data is the ID data, the ID data is set. In this case, as shown in FIG. 17, for example, the storage area for the final number LNO of the recorded frame memory, ID data, patient data such as the dates of birth, the names and the like, the search number pointer TNO in the frame memory sections and the search flag LEME in the frame memory sections are set in a given area of RAM 52. When the final number LNO of the recorded frame memory section is first reset to zero, the ID input mode is moved to the examination mode.

The search number pointer TNO in the frame memory sections is data for indicating the number of the frame memory section 44-i under search. The search flag LMEM in the frame memory sections is a flag for discriminating search and non-search in the frame memory sections during search, the flag being "1" in the case of search in the frame memory sections.

Figure 18:
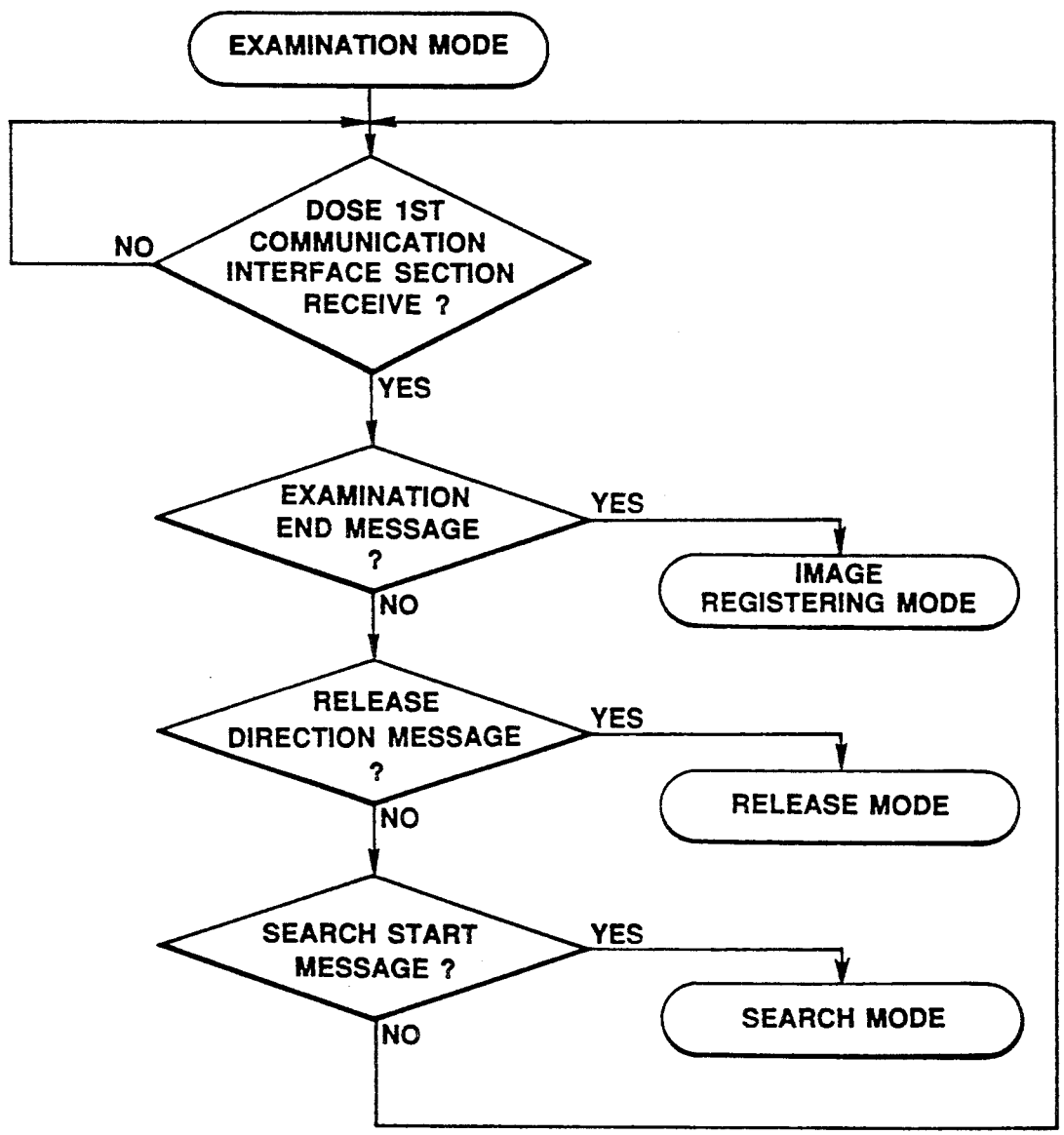

FIG. 18 shows the operation in the examination mode.

A check is first made as to whether or not data is input to the first communication interface section 53. When data is input, decisions are made as to whether or not the input data is a message of examination end, whether or not it is a release prompting message and whether or not it is a search start message. In the case of a message of examination end, the examination mode is moved to the image registering mode shown in FIG. 21. In the case of a release prompting message, the examination mode is moved to the release mode shown in FIG. 19, and, in the case of a search start message, the examination mode is moved to the search mode shown in FIG. 20.

In another case, the examination mode returns to the initial state in which data input is waited.

FIG. 19 shows the operation in the release mode.

In the release mode, a decision is made as to whether the final number LNO of the recorded frame memory sections (also described as "memory final number" for short) is the maximum value (40 in this embodiment). In the case of YES, a message of abnormal end is transmitted to each image input apparatus 15I through the first communication interface section 53 because any data cannot be further stored, and the release mode returns to the examination mode. In this case, the control section 34 in each image input apparatus 15I outputs a control signal to the image processing section 31 so that a message of abnormal end is superimposed and displayed, and then the freezing is released for the next release operation.

While when the memory final number LNO is not 40, the memory final number LNO is increased by one, and then a direction of write is output to the frame memory section 44-i (i=LNO) of the memory final number LNO so that the RGB signals output from each image input apparatus 15I are written in the frame memory section 44-i of the number LNO. A message of normal end is then transmitted to the image input apparatus 15I through the first communication interface section 53, and the release mode returns to the examination mode. In this case, when each image input apparatus 15I receives a normal end message, it outputs a signal for releasing the freeze to the image memory 33.

Figure 20A:
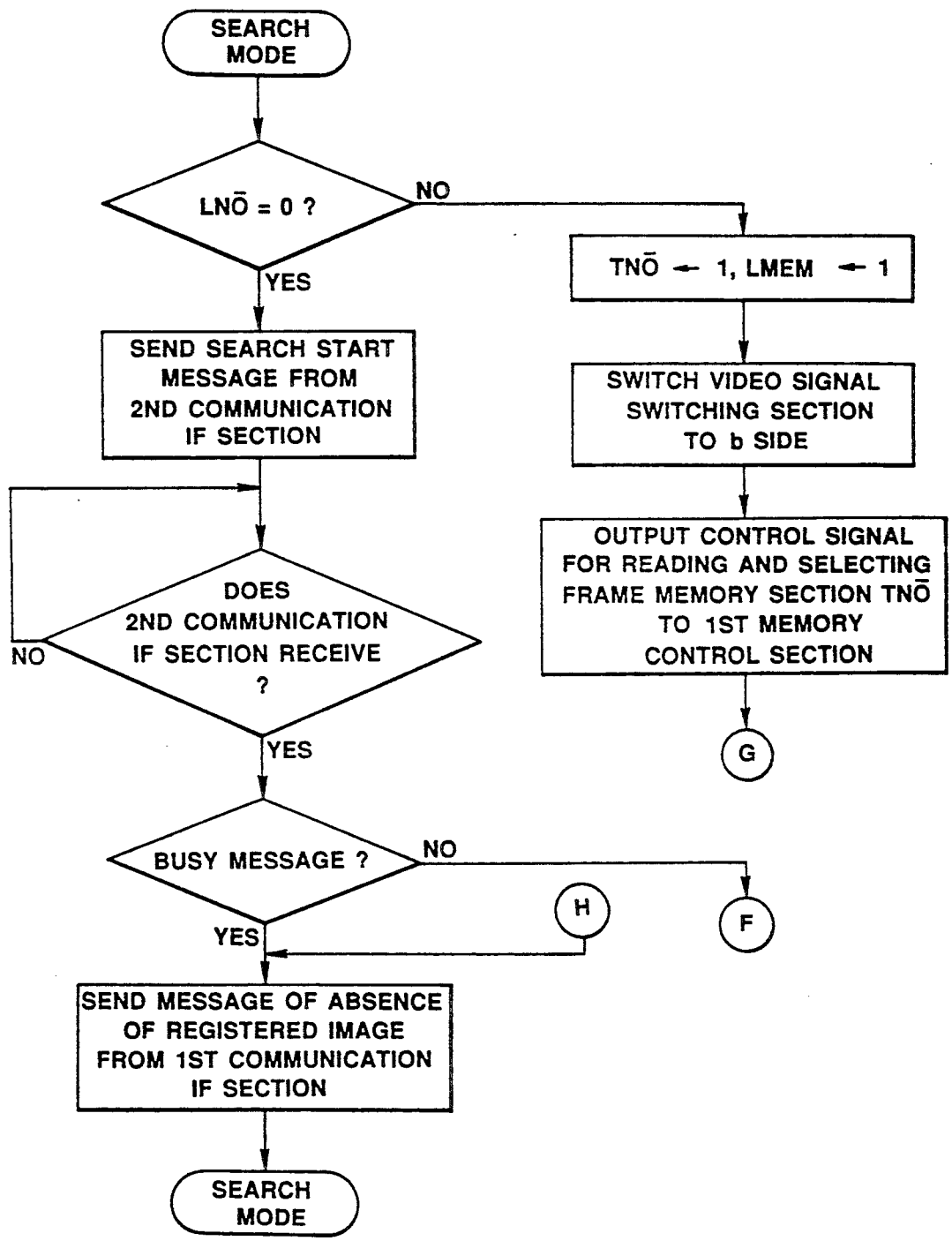

FIGS. 20a, 20b, . . . , 20g show the operation in the search mode.

In the search mode, a decision is first made as to whether or not the memory final number LNO is zero. In other words, a check is made as to whether or not there are images for search in each small image filing apparatus 17I. In the case of "0", since there is no search image in the small capacity image filing apparatuses 17I, a search start message is sent to the external image FIF apparatus 3 (i.e., to the large capacity image filing apparatus 4 through the image FIF apparatus).

Then, input of data from the side of the image FIF apparatus 3 through the second communication interface section (abbreviated to the "second communication FI section in the flowcharts) 54 is waited. It is the decided whether or not the input data is a busy message. When the input data is not a busy message, the processing shown in FIG. 20b is performed, while when the input data is a busy message, (in this embodiment), a message of the absence of any registered image is sent to the image input apparatuses 15I through the first communication interface section 53, and the search mode returns to the initial state thereof. In the case of the busy message, it is also possible to send to each image input apparatus 15I a message os the check as to whether or not the search is waited until a busy message is not input so as to perform processing in accordance with an answer thereto.

On the Other hand, when the memory final number LNO is not zero, both of the number pointer TNO in the search frame memory sections and the search flag LMEM in the frame memory sections, both of which are shown in FIG. 17, are set to "1", and the video signal switching section 59 shown in FIG. 7 is switched to the b-side so that the video signals from the frame memory Sections 44-i can be output. In other words, the TNO value is set to "1" so as to set search in the first frame memory 44-1, which is first released, in each small capacity image filing apparatus 17I. At the same time, the LMEM value is set to "1" so as to show a flag indicating the search on the frame memory section side.

A control signal is then output to the first memory control section 45 so that the first frame memory section 44-1 is selected and read, and the process is transferred to the processing shown in FIG. 20c. The video signal read from the first frame memory section 44-1 by the control signal is output to the image input apparatus 15I through the video signal switching section 59, and the image of the signal is displayed on the color monitor 16I.

When the data received by the second communication interface section 54 is not a busy message, as shown in FIG. 20b, after the ID data has been transmitted from the second communication interface section 54 to the side of the image FIF apparatus 3, the second communication interface section 54 waits for data as a reply. The ID data sent to the image FIF apparatus 3 side is further transferred to the large capacity image filing apparatus 4 in which a search is made as to whether or not the image of the ID data is present in the large capacity image filing apparatus 4.

This search causes an examination on the registered image, and a reply message is returned to the second communication interface section 54. A decision is made as to whether or not the data input to the second communication interface section 54 indicates the presence of the registered image. When there is no registered image, as shown in FIG. 20a, a message of the absence of the registered image is sent to each image input apparatus 15I through the first communication interface section 53. While when there is the registered image, the search flag LMEM in the frame memory sections is set to "0" so as to indicate that the search is not local image search in each small capacity image filing apparatus 17I.

In addition, a direction is sent to the second memory control section 56 so that the image data is written in the display memory section 55, and the RGB signals read by the search from the large capacity image filing apparatus 4 through the image FIF apparatus 3 are stored in the frame memory section 55. Further, the video signal switching section 59 is switched to the a-side so that the image data written in the frame memory section 55 is output, and the process proceeds to the processing shown in FIG. 20c.

In other words, after a message of the Presence of the registered image has been transmitted to each image input apparatus 15I from the first communication interface section 53, data input from each image input apparatus 15I is waited for. In this case, each image input apparatus 15I switches the image signal switch 35 to the external signal side so that the image input through the image FIF apparatus 3 is displayed on each color monitor 16I, as shown in FIG. 14a. In this state, data input is waited as to whether or not the search is finished. The input data is transmitted to the first communication interface section 53 of each small capacity image filing apparatus 17I through the communication interface section 37.

When the data is input to the first communication interface section 53, a decision is made as to whether the data indicates a message of search end, a direction of search for the before image, a direction of search for the next image, a direction of search for the before examination or a direction of search for the next examination. In the case of a message of search end, the message of search end is sent to the large capacity image filing apparatus 4 from the second communication interface section 54 through the image FIF apparatus 3, and the search mode returns to the examination mode.

While, in the case of the search for the before image, the next image, the before examination or the next examination, the processing shown in FIGS. 20d, 20e, 20f or 20g is performed.

When it is decided that the input data indicates a direction of search for the before image, a decision is made as to whether or not the search flag in the frame memory sections is "1". When the flag is "1" (local search in each small capacity image filing apparatus 17I), a decision is further made as to whether or not the search number pointer TNO in the frame memory sections is "1". When the number pointer is "1", since there is not before image, a message of the absence of the before image is transmitted to each image input apparatus 15I from the first communication interface section 53, and the input of data transmitted from the image input apparatus 15I is waited for. While, when the number pointer TNO is not 1, the number pointer TNO is decreased by 1, and a control signal is output to the first memory control section 45 so that the frame memory section 44-i (i=TNO) of the number pointer TNO is selected and read. The image data read from the frame memory section 44-i by the control signal is output to the image input apparatus 15I. After the control signal has been output, a message of the presence of the before image is transmitted from the first communication interface section 53, and data input to the first communication interface section 53 is waited for, as shown in FIG. 20c.

When the search flag LMEM in the frame memory sections is not "1", since the search is not local search, a direction of search for the before image is sent to the large capacity filing apparatus 4 from the second communication interface section 54 through the image FIF apparatus 3, and then the return of data to the second communication interface section 54 is waited for. When data is input, a decision is made as to whether or not the before image is present. When the before image is present, a direction is given to the display frame memory section 55 so that the image data is written. Then, a message of the present of the before image is transmitted from the first communication interface section 53. (This transmission causes the display of the before image on the color monitor connected to each image input apparatus).

On the other hand, when it is decided that there is no before image, a message of the absence of the before image is transmitted from the first communication interface section 53.

When it is decided that the input data indicates a direction of search for the next image, the processing shown in FIG. 20e is performed.

Figure 20D:
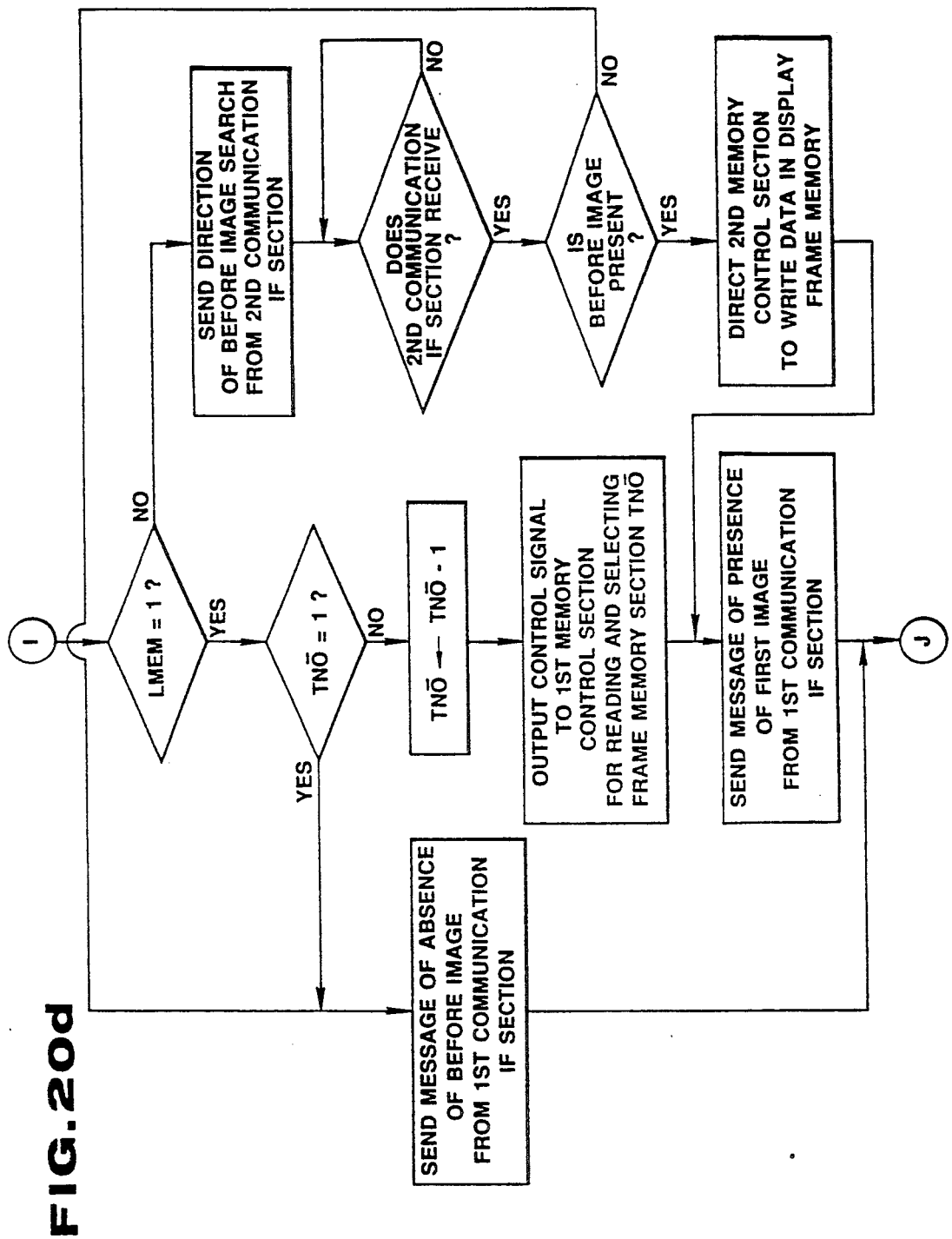

In this case, a decision is made as to whether or not the search flag LMEM in the frame memory sections is "1", in the same way as in FIG. 20d. In the case of local search with the flag of 1, a decision is made as to whether or not the search number pointer TNO in the frame memory sections equals to the final number LNO of the recorded frame memory sections. In other words, a decision is made as to whether or not the search is performed for the newest recorded image. In the case of YES, therefore, there is no image next the present image. While, in the case of NO, since there is the next image, the number pointer TNO is increased by 1 so that the image of the frame memory section 44-i of that number pointer TNO is displayed. The other processes are the same as those shown in FIG. 20d and are thus not described below.

In FIG. 20c, when it is decided that the input data shows search for the next examination, the processing shown in FIG. 20f is carried out.

A decision is first made as to whether or not the search flag LMEM in the frame memory sections is "1", i.e., whether or not the present search is local search. When the present search is local search, a search start message is transmitted to the large capacity image filing apparatus 4 from the second communication interface section 54 through the image FIF apparatus 3. The second communication interface section 54 then waits for data. When the interface section 54 receives data, a decision is made as to whether or not the data received is a busy message. In the case of a busy message, there-fore, a message of the absence of the before examination is transmitted from the first communication interface section 53, and the first communication interface section 53 shown in FIG. 20c waits for data input. While when the data input is not a busy message, the ID data is transmitted from the second communication interface section 54, and reply data is waited for. In this case, the large capacity image filing apparatus 4 performs image search of the ID data and then sends the results of the search.

When there is the registered image, after "0" has been substituted for the flag LMEM and "1" has been substituted for the number pointer TNO, a direction is given to the second memory control section 56 so that the image data is written in the display frame memory section 55. A message of the presence of the before examination is then transmitted from the first communication interface section 53.

The image data written in the display frame memory section 55 is input to the image input apparatus 15I and displayed on the color monitor 16I.

On the other hand, when the flag LMEM is not "1", since the large image filing apparatus 4 has already been searched, a direction of search for the before examination is transmitted from the second communication interface section 54, and the second communication interface section 54 then waits for data input from the large capacity image filing apparatus 4. When data is input, a decision is made whether or not the before examination is present. When there is no before examination, a message of the absence of the before examination is transmitted from the first communication interface section 53.

While when there is the before examination, a direction is given to the second memory control section 56 so that the image data is written in the display frame memory section 55.

In FIG. 20c, when there is the next examination, the processing shown in FIG. 20g is performed.

A decision is made as to whether or not the flag LMEM is "1", in the same manner as in FIG. 20f. In the case of "1", since the present search state is local search, there is no next examination. Thus, a message of the absence of the next examination is transmitted from the first communication interface section 5, data input from the image input apparatus 15I waited for.

On the other hand, when the flag LMEM is not "1", a message of search for the next examination is sent from the second communication interface section 54, and the interface section 54 then waits for data input from the large capacity image filing apparatus 4 through the image FIF apparatus 3. When data is input, a decision is made whether or not the data shows the presence of the next examination. In the case of the presence of the next examination, a direction is given to the second memory control section 56 so that the image data is written in the display frame memory section 55. A message of the presence of the next examination is then sent from the first communication interface section 53, the interface section 53 waits for data input from each image filing apparatus 15I. On the other hand, when it is decided that there is no next examination, a decision is made as to whether or not the final number LNO of the recorded frame memory sections is "0". In the case of "0", since no image is recorded in each small capacity image filing apparatus 15I, a message of the absence of the next examination is transmitted through the first communication interface section 53. When the final number LNO is not "0", since there are recorded images, after both the search number pointer TNO in the frame memory sections and the flag LMEM of search in the frame memory sections have been set to "1", the video signal switching section 59 is switched to the b-side so that the image data in the frame memory sections 44-i is selected. Then, a control signal is output to the first memory control section 45 so that the first frame memory section 44-1 is selected and read. The control signal causes the image data in the first frame memory section 44-1 to be read and output to the side of the image input apparatuses 15I. The image data output is displayed on the color monitors 16I. After the control signal has been output, a message of search end is transmitted from the second communication interface section 54 to the large capacity image filing apparatus 4 through the image FIF apparatus 3, and then a message of the presence of the next examination is sent to the image input apparatuses 15I from the first communication interface section 53.

After a release operation for a single examination has been performed in the examination mode, when data for examination end is input from the data is input to the section 36 of each image input apparatus 15I, the data input is first communication interface section 53 of each small capacity image filing apparatus 15I. When it is decided that the data input is a message of examination end, as shown in FIG. 14, the examination mode is moved to the image registering mode shown in FIG. 21. In this mode, the image data recorded in the frame memory sections 44-1, 44-2, . . . by the release operation is output to the large capacity image filing apparatus 4. The image data for a single examination is recorded in the apparatus 4, as well as the information with respect to the recorded image data being written in the database thereof.

Figure 21:
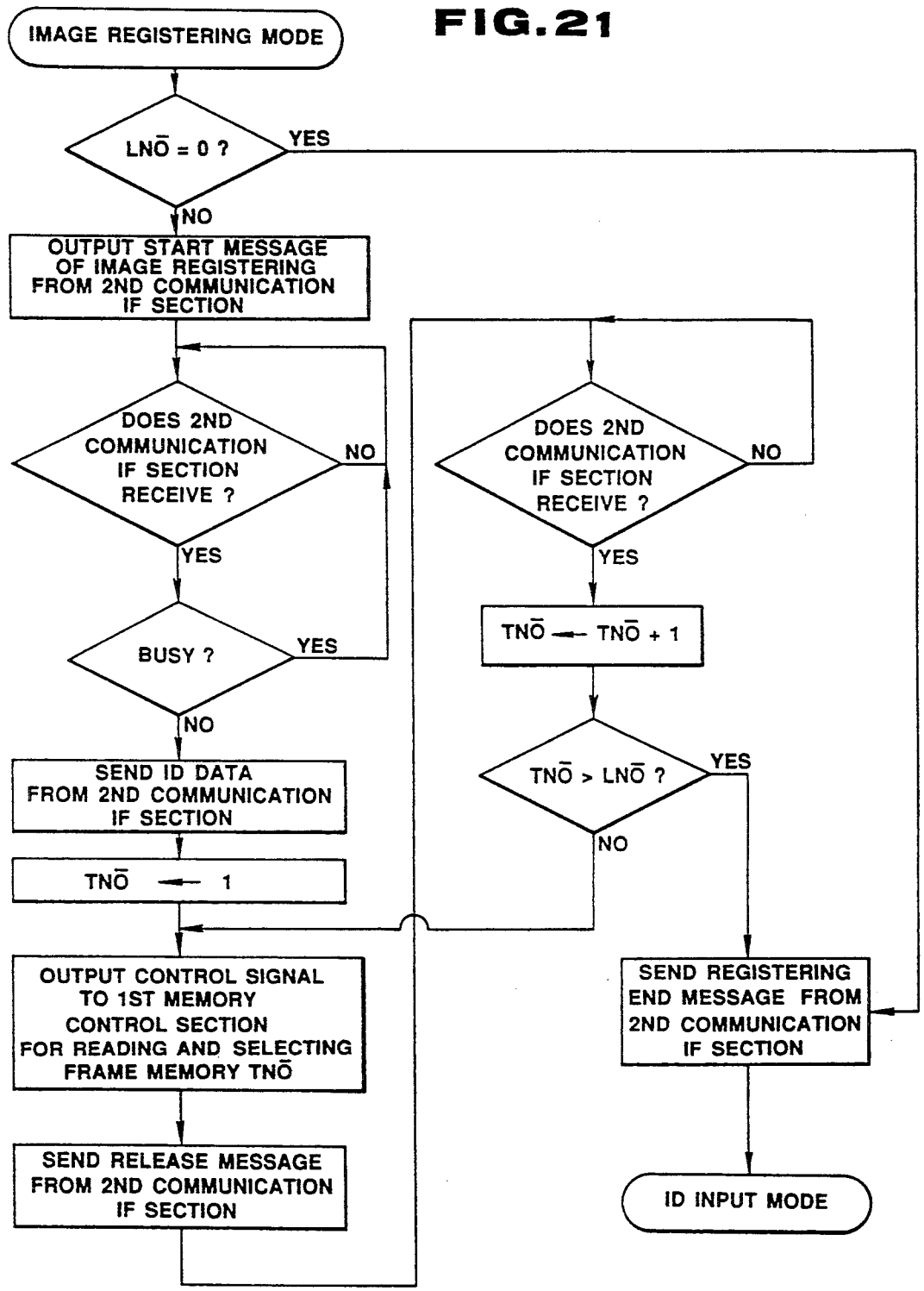

In FIG. 21, in the image registering mode, a decision is first made as to whether or not the final number LNO of the recorded frame memory sections is "0". When the final number is "0", since there is no recorded image, the registering mode is moved to the ID input mode.

While when the final number LNO is not "0", a start message for image registering is output to the large capacity image filing apparatus 4 from the second communication interface section 54 through the image FIF apparatus 3, and a reply thereto is waited. A decision is then made as to whether or not the input data is a busy message. In the case of a busy message, input of a message, which is not a busy message, is waited for. When the input data is not a busy message, the patient data such as the ID data of a patient and the date of birth thereof are sent from the second communication interface section 54, and the search number pointer TNO of the frame memory sections is then set to "1" so that the images are recorded in turn from the image data in the first frame memory section 44-1.

Namely, after a control signal has been output to the first memory control section 45 so that the first frame memory section 44-1 is selected and read, a release message is transmitted from the second communication interface section 54, and the communication interface section 54 waits for a reply thereto. The release message causes the recording of the image data read from the first frame memory 44-1 in the large capacity image filing apparatus 4. When the recording is completed, a reply is given to the second communication interface section 54. In this case, the number pointer TNC is increased by 1, and a decision is made as to whether or not the increased number pointer TNO is greater than the final number LNO of the recorded frame memory sections. When the number pointer YNO is over the final number LNO, since there is no more image data to be registered, a message of registering end is transmitted from the second communication interface section 54, and the registering mode is moved to the ID input mode.

While, when the number pointer TNO is less than the final number LNO, since there is further images to be registered, a control signal is output to the first memory control section 45 so that the frame memory section 44-TNO is selected and read, and a release message is then sent from the second communication interface section 54. In this way, the image data for a single examination is recorded in the large capacity image filing apparatus 4, as well as information of the recorded image data such as the I data and the patient data being recorded in the data base, and the registering of the image is completed and moved to the ID mode.

A description will now be given of the operation of the image FIF apparatus 3 which is interposed between the each small capacity image filing apparatus 15I and the large capacity image filing apparatus 4.

Figure 22:
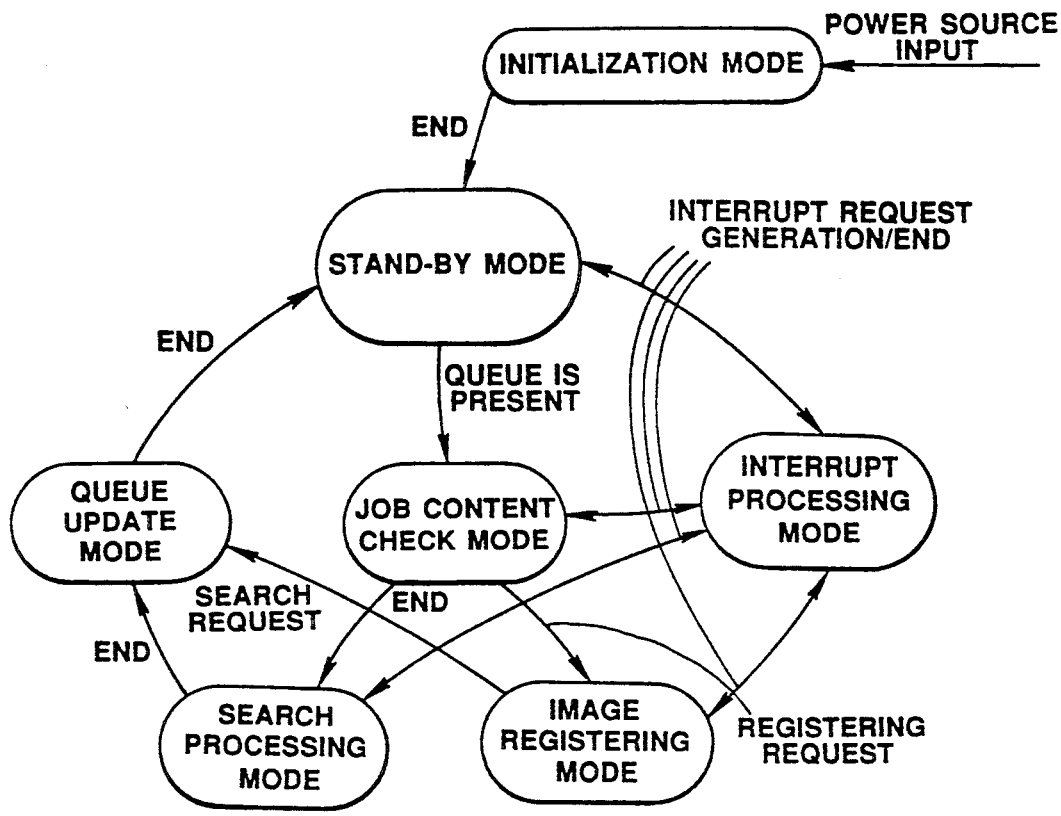

FIG. 22 is a state transition drawing which shows the transition states between respective operation modes of the image FIF apparatus 3.

After the image FIF apparatus 3 has been initialized in the initialization mode by turning the power source on, the mode is moved to the TSTAND-BY mode. The STAND-BY mode is a state wherein the first, second, . . . , or Nth communication interface section 69-1, 69-2, . . . , 69-N shown in FIG. 4 waits for the reception of a job request.

Figure 23:
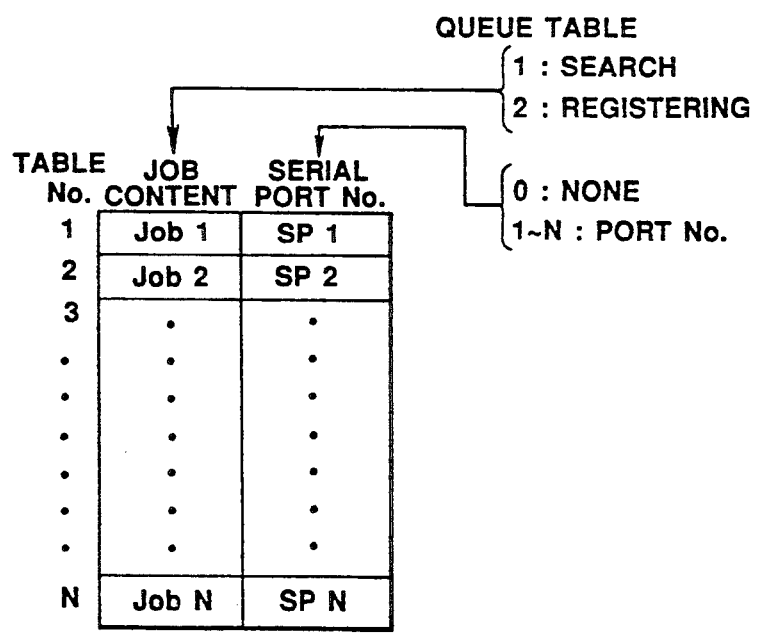

The contents of the jobs received by the first, second, Nth interface communication section 69-1, 69-2, . . . , 69-N are written in the queue table shown in FIG. 23. In the queue table, the contents are written in the order of priority of processing, the job content No.1 in the table having the highest priority (denoted by Job 1 in FIG. 23). Each of the job contents is written together with the serial port number so that is is possible to recognize which communication interface receives the job content. In FIG. 23, the serial port number is denoted by Spj (j=1, 2,. . . , N).

For example, in the job contents, numeral "1" denotes search and numeral "2" denotes registering. In addition, when the numeral of the serial port 69-i is "0", there is no job, and numerals 1 to N represent the jobs which are respectively received by the serial port of that numerals.

In the queue table, the contents in the table are upwardly moved and updated in turn each time the job with the highest priority is finished so that the job content at the top in the table is always the job with the highest priority. In the STAND-BY mode, therefore, a check is made as to whether or not there is a queue (job) by checking whether or not the serial port number of Table No. 1 in the queue table is "0". When the serial port number is not "0", the STAND-BY mode is moved to a mode of checking the job contents. In the case of "1", the mode is moved to a search processing mode, while in the case of "2", the mode is moved to the image registering mode. After the search processing mode or the image registering mode has been completed, the mode is moved to queue update mode in which the queue table is updated, and then the mode is returned to the STAND-BY mode.

The image FIF apparatus 3 further has an interrupt processing mode so that, when a request for interrupt is input to the first, second, . . . or Nth serial port 69-1, 69-2, . . . , 69-N, the interrupt processing mode is established as a mode other than the queue update mode. After the interrupt processing has been completed, the mode returns to the mode before the interruption.

Each of the modes will be described below.

In the initialization mode, interruption is first inhibited and then allowed after all the serial port numbers Nos. (Sp1 to SpN) in the queue have been cleared to "0". The initialization mode is then moved to the STAND-BY mode in which a decision is made as to whether or not the content of the the serial port No. Sp1 of the queue table No. 1 is "0". Since the job content of the table No. 1 is the job with the highest priority, if the content of the serial port No. Sp1 is "0", there is no job of processing, and thus data, which is not "0", is waited. When the data input is not "0", the STAND-BY mode is moved to the job content check mode. In the job content check mode, a decision is made whether Job1 is "1" or "2". In the case of "1", the mode is moved to the search processing mode shown in FIG. 25a, while in the case of "2", the mode is moved to the image registering mode shown in FIG. 22.

Figure 25A:
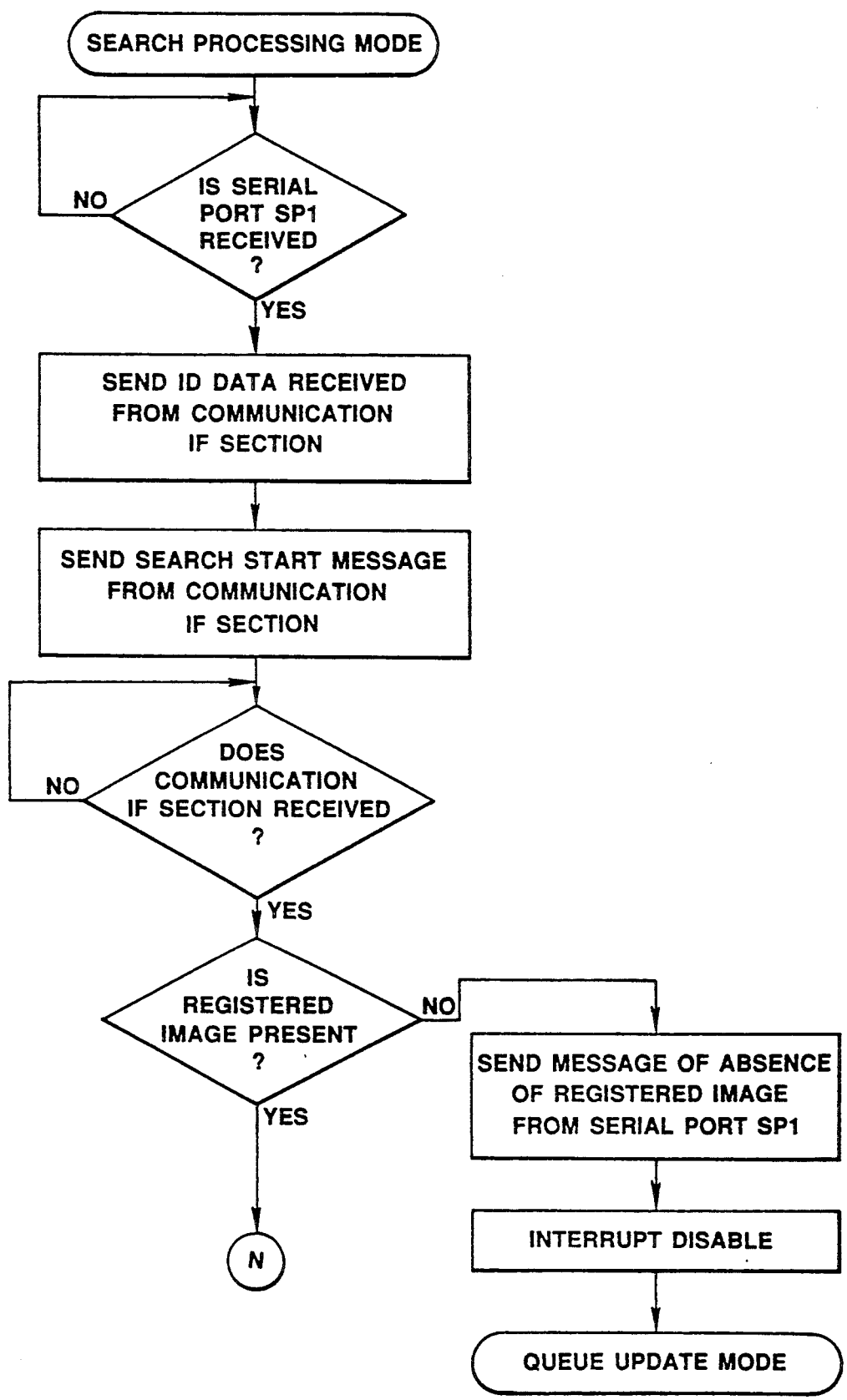
FIGS. 25a, 25b are flowcharts which show the process in a search processing mode.

In the search processing mode shown in FIG. 25a, a decision is made as to whether the ID data is input to the serial port No. SP1, and data input is waited for. When the data is input, the ID data received is transmitted to the large capacity image filing apparatus 4 from the communication interface section 68 shown in FIG. 8 which then outputs a search start message and waits for a reply thereto. When the communication interface section 68 receives a reply indicating that there is no registered image, a massage of the absence of registered images is transmitted from the serial port 69-Sp1 to the side (image input/filing apparatus) 2I of the small capacity image filing apparatus 17. Then, interruption is inhibited and the registering mode is moved to the queue update mode.

Figure 25B:
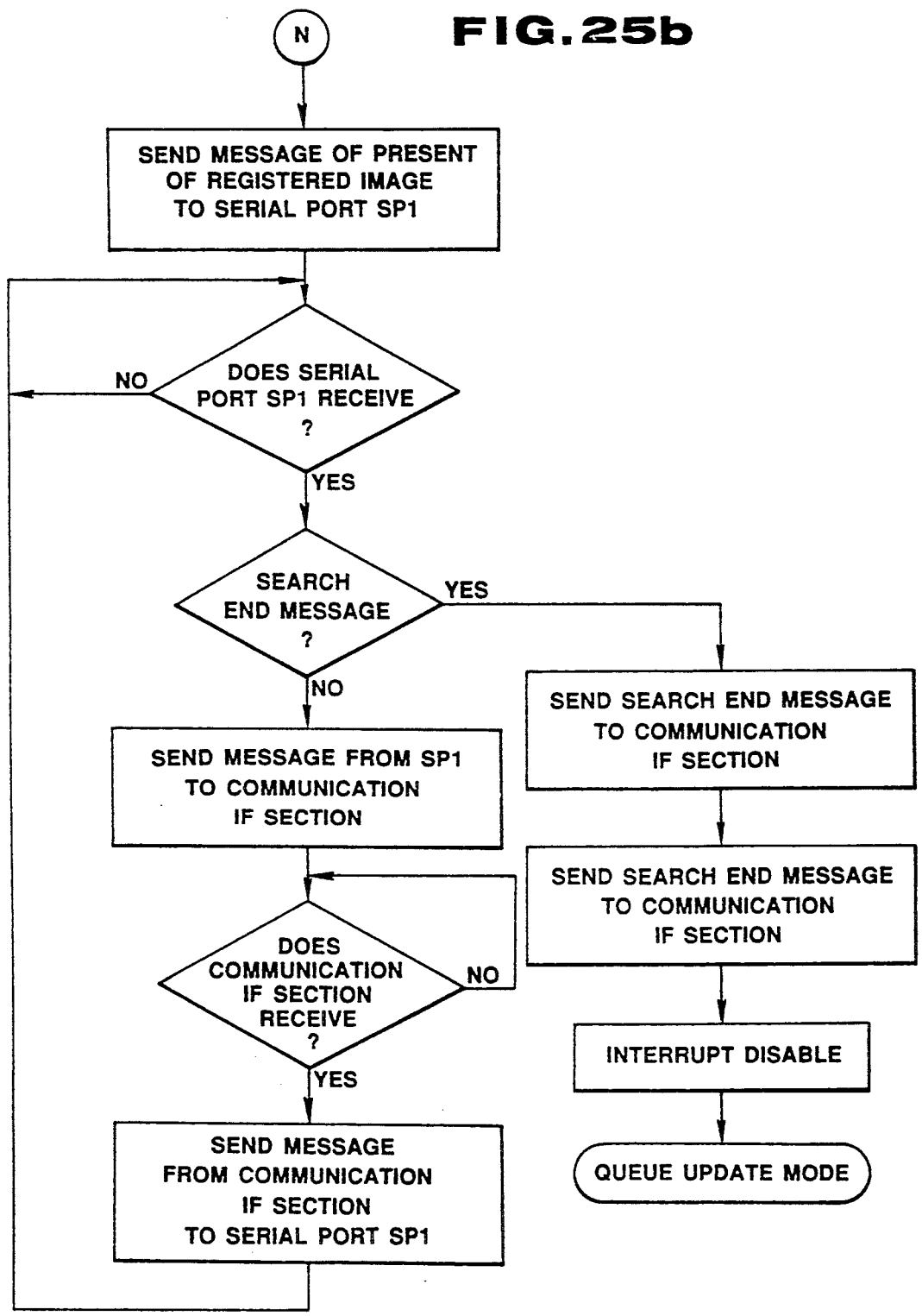

On the other hand, when the communication interface section 68 receives a reply indicating that there is the registered image, a message of the presence of the registered image is transmitted to the serial port 69-Sp1 of the port number Sp1, as shown in FIG. 25b. The communication interface section 68 then waits for a message from the image input/filing apparatus 2I. A decision is then made as to whether or not the data received is a message of search end. In the case of search end, a message of search end is transmitted from the communication interface section 68 to the large capacity image filing apparatus 4, and a message of examination end is then transmitted from the communication interface section 68 so that interruption is inhibited. The queue update mode is then established.

On the other hand, when it is decided that the input data is not the message of search end, since the data is a message of search for the before image, the next image, the before examination or the next examination, the message received by the serial port 69-Sp1 is transmitted to the large capacity image filing apparatus 4 from the communication interface section 68 without any processing. The communication interface section 68 then waits for a reply thereto. When data (message) is input to the communication interface section 68, the message is sent to the serial port 69-Sp1 as it was, and the serial port 69-Sp1 returns to a state wherein it waits for data (message).

To the image input/filing apparatus 2I which is connected to the serial port 69-Sp1 is input a message of a replay to the message, i.e., the search for the before image or the like, which is returned from the large capacity image filing apparatus. For example, when there is a search image, the image is displayed on the color monitor 16I of the image input/filing apparatus 2I.

Figure 24:
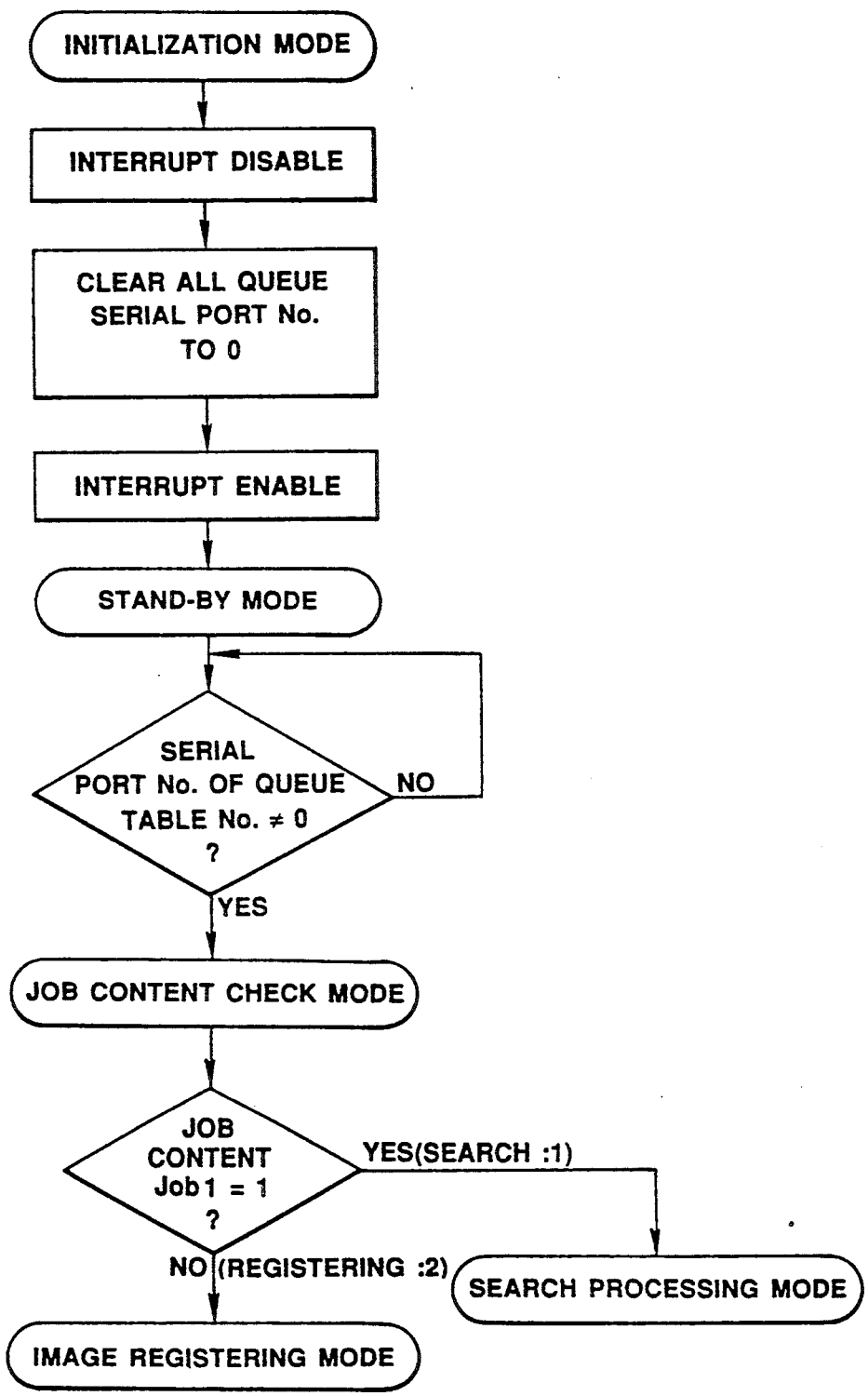
Figure 26:
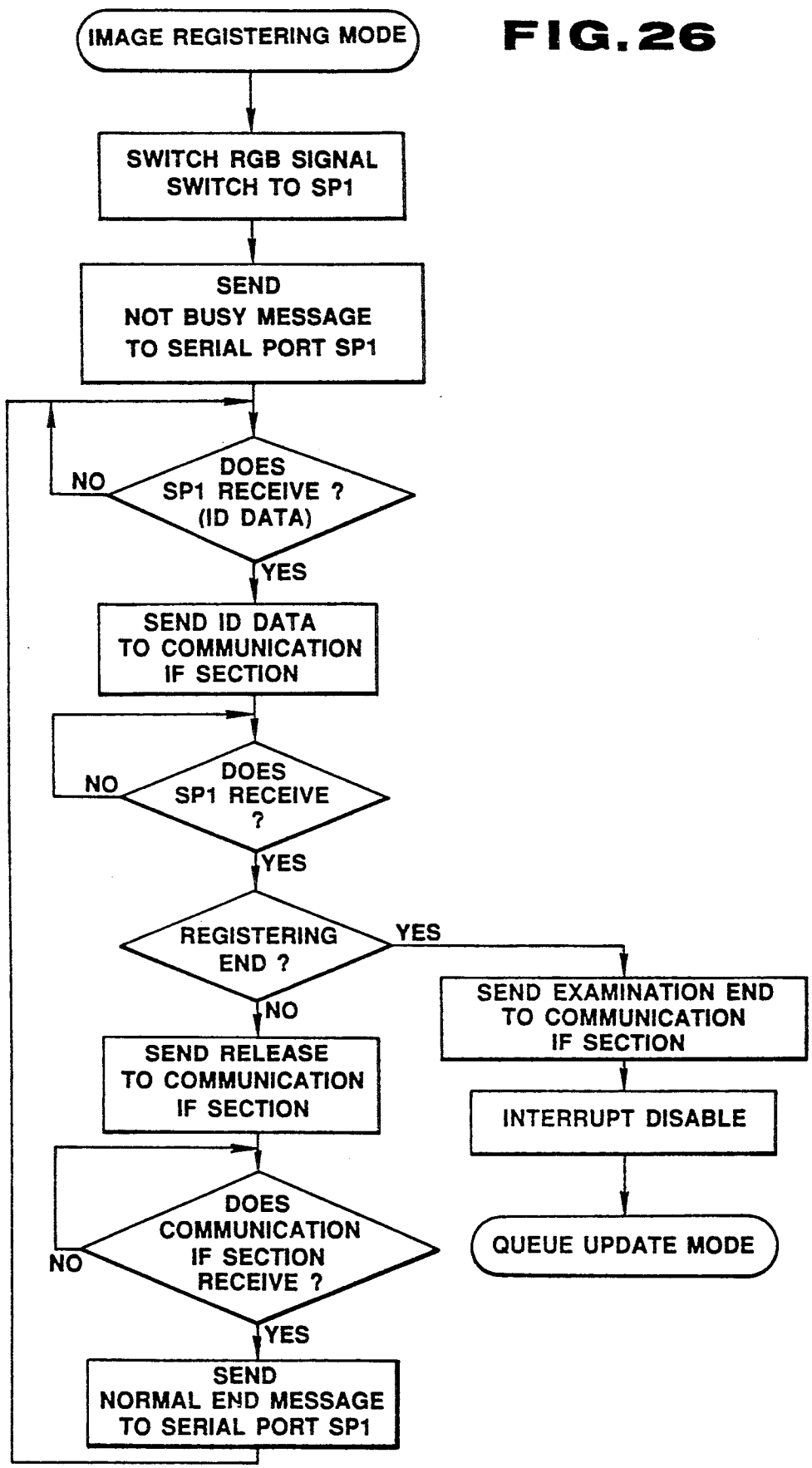

In the processing shown in FIG. 24, when the job content Job1 is "2", the image registering mode shown in FIG. 26 is established.

The RGB signal switch 61 is first switched so as to select the RGB signal from the image input/filing apparatus 2I of the serial port 69-Sp1, and a Not busy message is transmitted to the serial port 69-Sp1, and a reply is waited. When a message is input, the ID data received is sent to the communication interface section 68 which then sends the ID data to the large capacity image filing apparatus 4, and the serial port 69-Sp1 then waits for input.

When the serial port 69-Sp1 receives data, a decision is made as to whether or not the data is a prompting message of registering end. In the case of registering end, a message of examination end is transmitted from the communication interface section 68, and an interruption is then inhibited. The queue update mode is then established.

While when the data is not a message of registering end, since the data is a release message, the release message is transmitted to the large capacity image filing apparatus 4 from the communication interface section 68 which then waits for a reply to the release message. When a reply is received, a message of normal end is sent to the serial port 69-Sp1 which then returns to a state wherein it waits for input.

Figure 27:
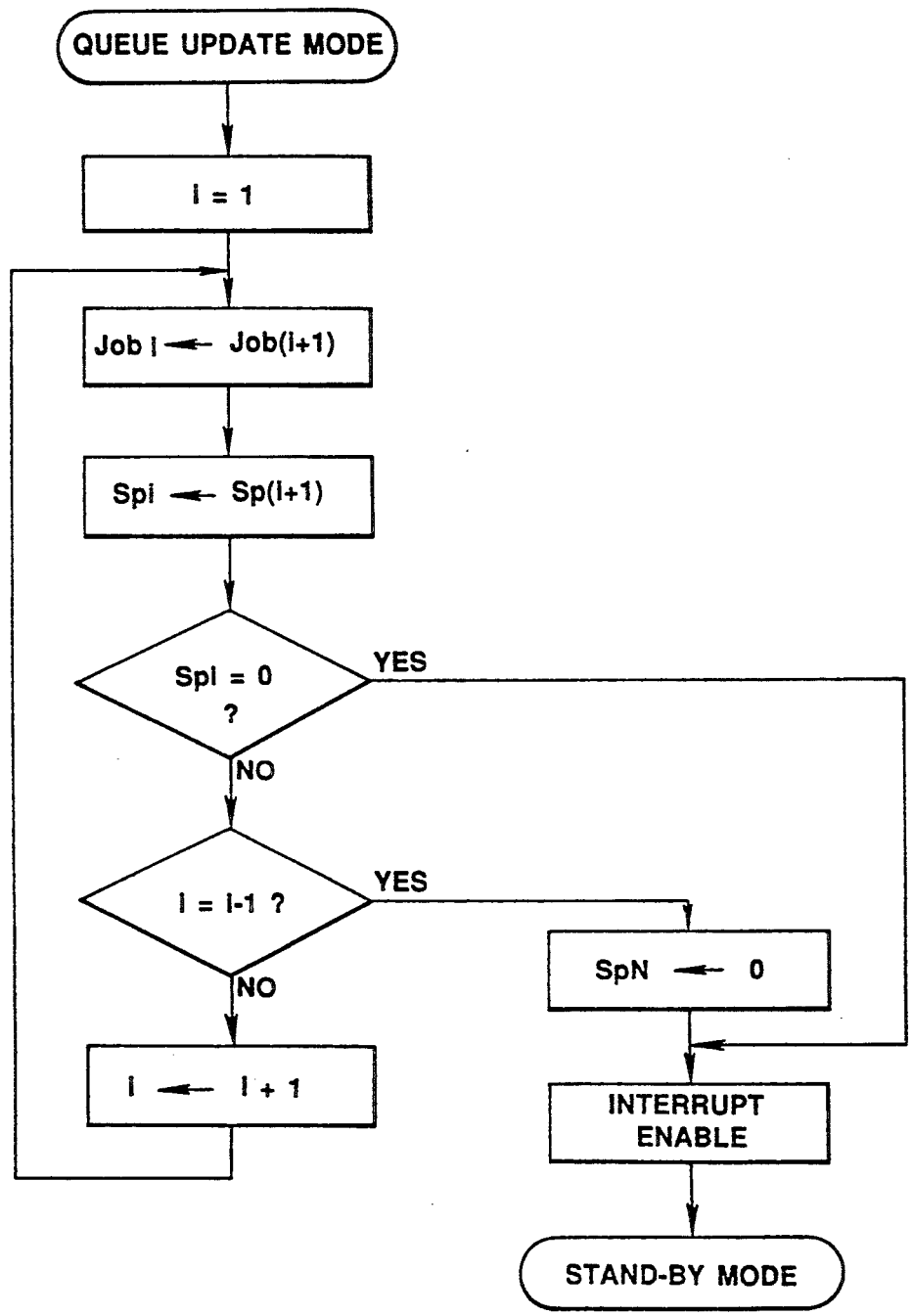

In the queue update mode, the processing shown in FIG. 27 is performed.

Numeral 1 is first set as a local variable i, and the content of Job $(i+1)$ is substituted for Job i (in this case, $i=1$) in the queue table shown in FIG. 23. The content of serial port number $Sp(i+1)$ is then substituted for the serial port No. Spi (in this case, $i=1$), and a decision is then made as to whether or not the content of the serial contents of the subsequent serial port Nos. are "0", it is unnecessary to update. Therefore, after a state wherein interruption is allowed has been established, the queue update mode is moved to the STAND-BY mode. When the content of the serial port No. Spi is not "0", a decision is made as to whether or not the local variable i is $N-1$. In the case of. $i=N-1$, "0" is substituted from the next serial port No. N (the serial port No. having the lowest priority), and a state wherein interruption is allowed is established. The queue update mode is then moved to the STAND-BY mode.

In the case of $i \neq N-1$, after i has been increased by one, the content of Job $(i+1)$ is substituted for Job i. The contents in the queue table shown in FIG. 23 are upwardly moved in turn by repeating the above processing so that "0" is substituted for the serial port No. at the bottom.

Figure 28:
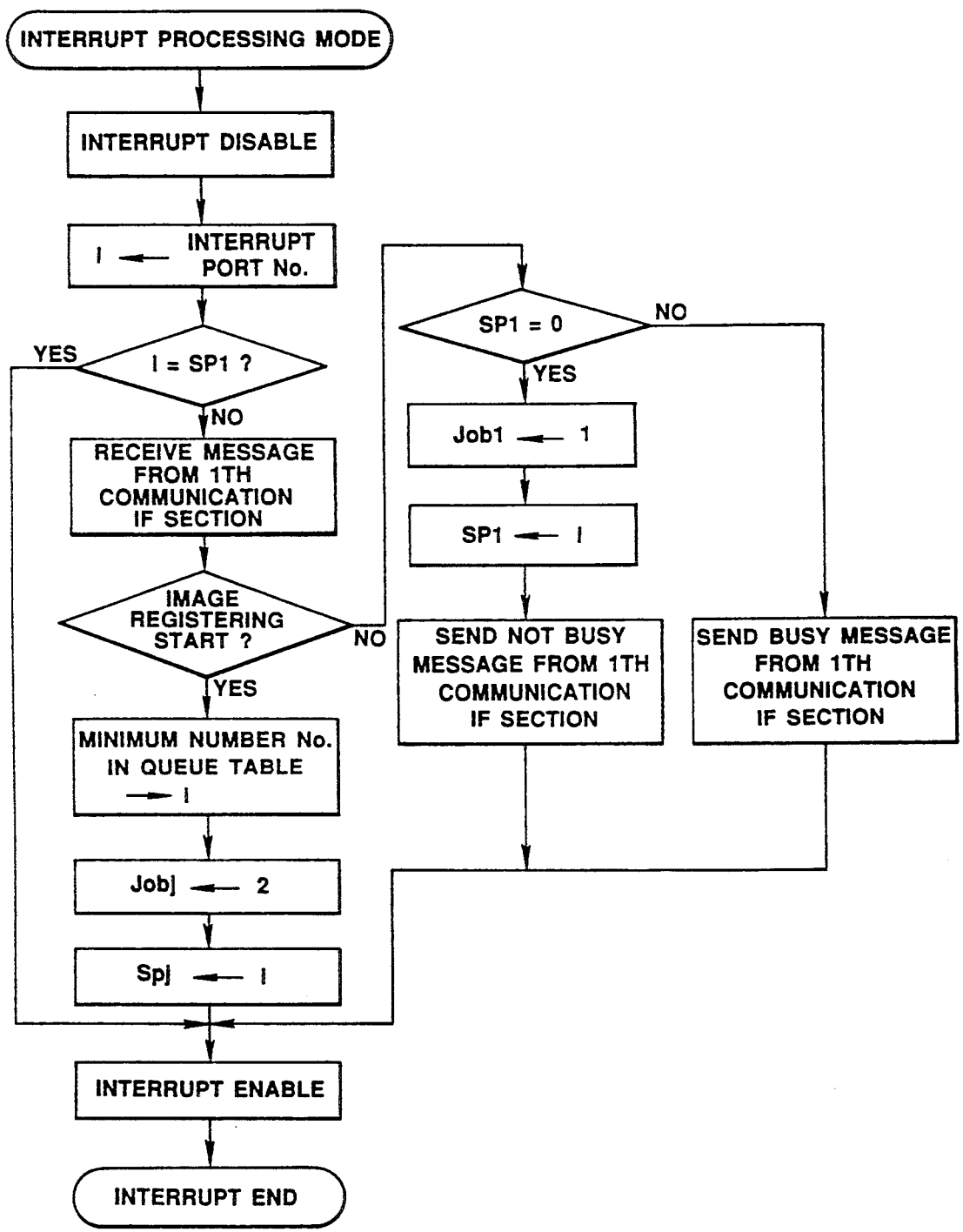

A description will now be given of the operation in the interrupt processing mode with the reference of FIG. 28.

In this mode, after interruption has been inhibited so that no other interruptions can be performed, the serial port No. for which interruption is inhibited is substituted for the local variable i. A decision is made as to whether or not the variable i is the serial port No. Sp1 with the highest priority (i.e., whether or not the variable i is equal to the serial port No. under processing). When the variable i is equal to that serial port No., the processing of the serial port No. Sp1 with the highest priority may be continued. The interrupt inhibit is released (interrupt enable) so that the interruption is finished.

While when the variable i is not equal to the serial port No. Sp1 with the highest priority, a message is received from the serial port i to which interrupt is applied for interrupt processing. A decision is then made as to whether or not the message indicates the start of image registering (i.e., whether the message indicates the start of image registering or the search for an image). In the case of NO, since the message indicates search, a decision is made as to whether or not the queue is in an empty state. That is, a decision is made as to whether the serial port No. Sp1 with the highest priority is "0". When the serial port No. Sp1 is not "0", a busy message is sent from the serial port i to which interruption is applied, and then interruption is enabled.

On the other hand, when the serial port No. Sp1 is "0", "1", i.e., the content of search, is substituted for the job Job1 with the highest priority, and then the value i of the serial port No. to which the interruption is applied is substituted for the serial port No. Sp1 in which the job content Job1 with the highest priority is performed. A not busy message is then transmitted from the serial port i, and an interruption enabled state is again established.

When the message indicates the start of image registering, the minimum empty No. in the queue table is substituted for a local variable j, and then "2" (registering) is substituted for the job content Jobj. The the serial port No., to which the interruption is applied, is then substituted for the serial port No. Spj, and then an interruption enabled state is established. This substitution enables the process of starting image registering to be performed in the process in which the jobs are performed in turn from the job content Job1 with the highest priority in the order of priority.

When the interruption is enabled and completed, the mode before the interruption is established.

A description will now be given of the operation of the large capacity image filing apparatus.

Figure 29:
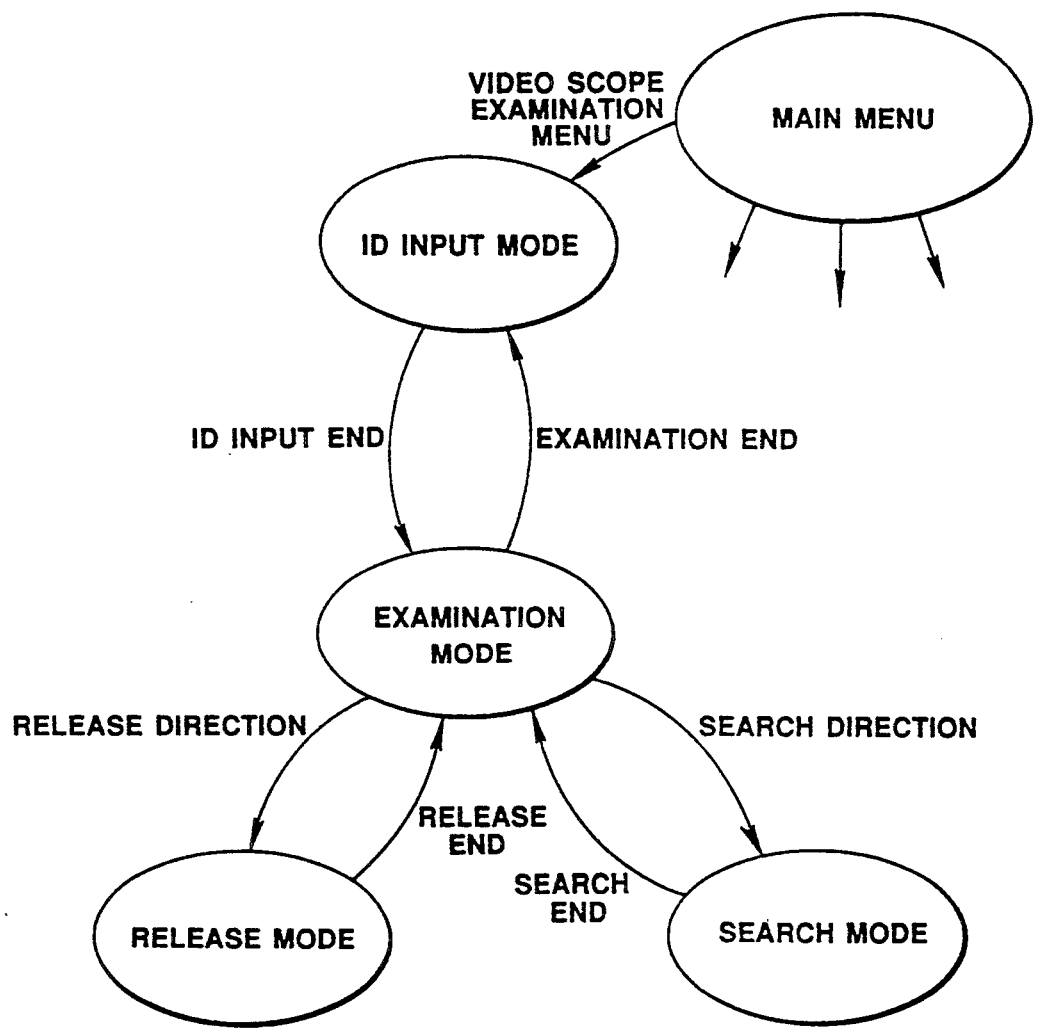
Figure 30:
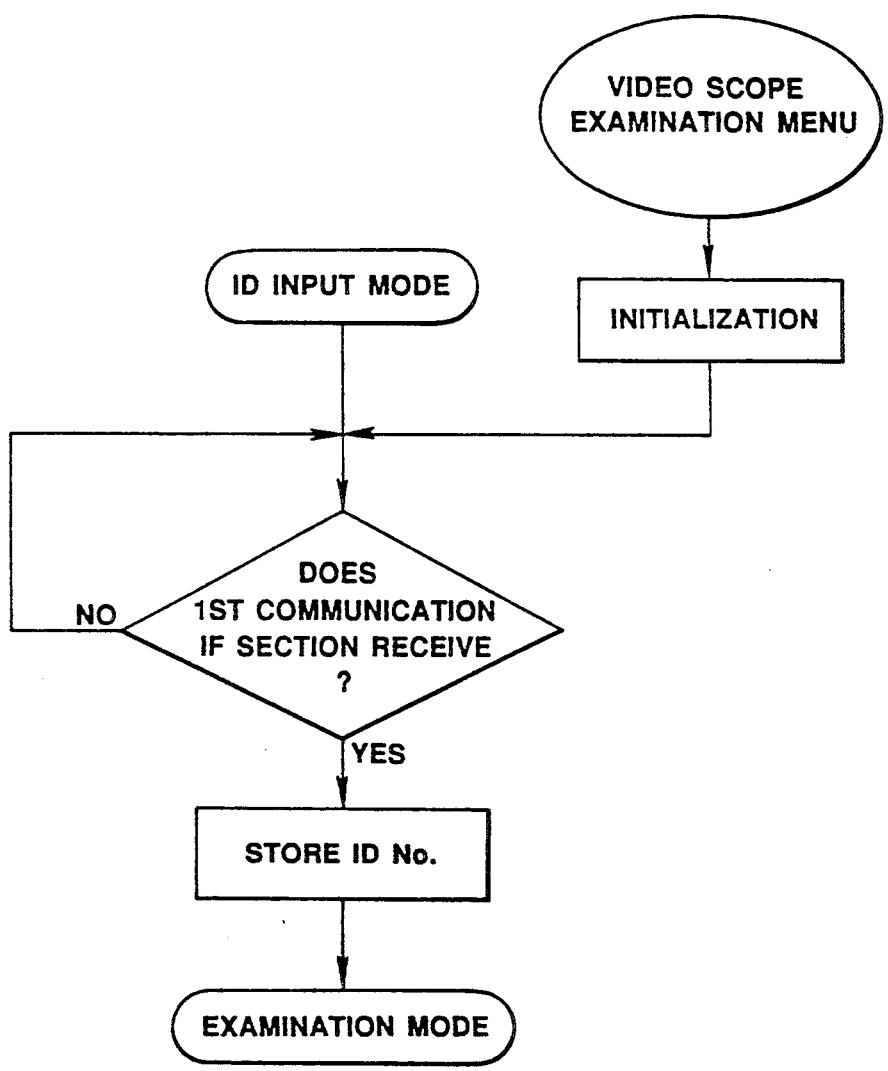

FIG. 29 is a state transition drawing of the large capacity image filing apparatus 4.

As shown in FIG. 29, when a video scope (electronic scope) examination menue which is a main menue is selected, the apparatus 4 has the same operation modes as that shown in the state transition drawing of each image input apparatus 15I. Namely, the apparatus 4 operates in the operation modes corresponding to each image input apparatus 15I.

The operation of each of the modes will be described in below.

As shown in FIG. 20, when the video scope examination menue is selected, after initialization has bee effected, the ID input mode is established.

Figure 31:
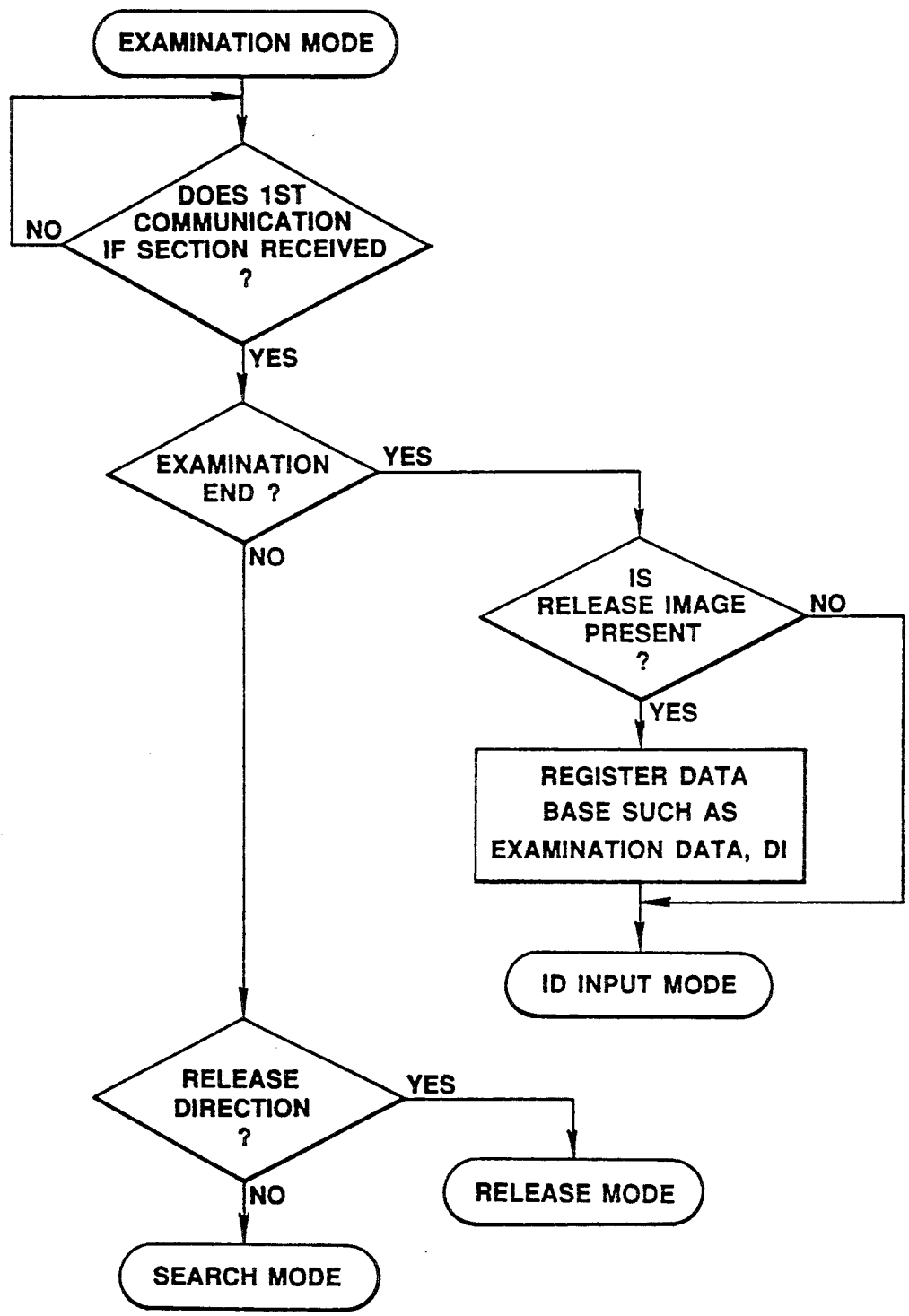

In the ID input mode, the first communication interface section 78 shown in FIG. 9 first waits for input of data. When data is input, since the first data is the ID data, the ID data No. is stored in a register or a memory 76, and the mode is moved to the examination mode shown in FIG. 31.

In the examination mode, the fist communication interface section 78 first waits for data input, and when data is input, a decision is made as to whether or not the data is message of examination end. In the case of examination end, a decision is made as to whether or not there is a release image. When there is a released image, the examination data and the ID data with respect to the released image are registered in the data base, and then the mode is returned to the ID input mode. While when there is no released image, since there is no need for registering in the data base, the mode is moved to the ID input mode.

On the other hand, the data is not a message of examination end, a decision is made as to whether or not the data is a message of a release direction. In the case of a release direction, the examination mode is moved to the release mode shown in FIG. 32. When the data is not a message of a release direction, the examination mode is moved to the search mode shown in FIG. 33.

Figure 32:
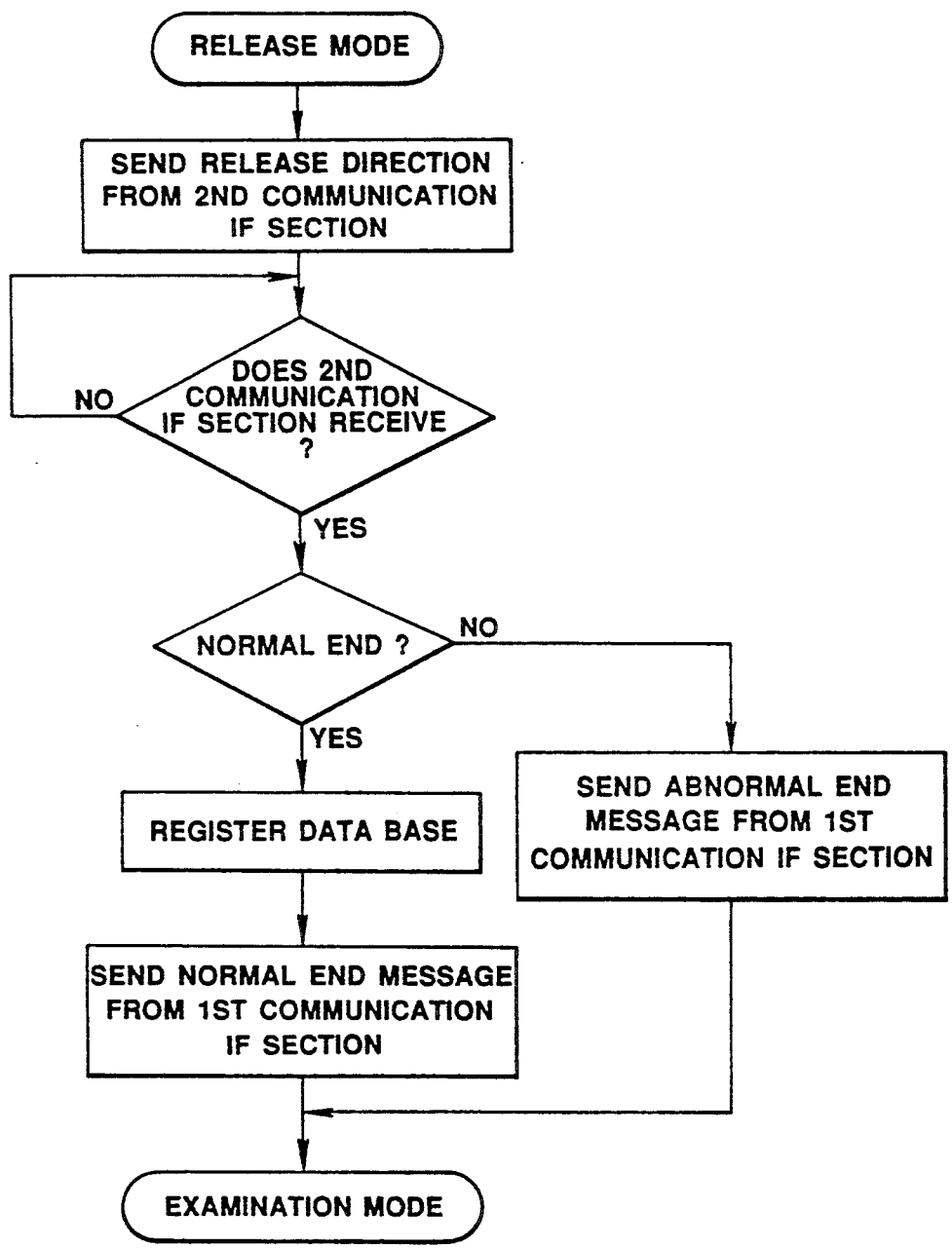

In the release mode shown in FIG. 32, a message of a release direction is sent to an optical disk recorder 72 from a second communication interface section 79 so that a direction is given to it so that the NTSC signal output from each image input/filing apparatus 2I through the image FIF apparatus 3 is recorded, and then the interface section 79 waits for a reply thereto. When a reply is returned, a decision is made as to whether the reply is a message of normal end. In the case of normal end, after the information with respect to the image has been registered in the data base, a message of normal end is sent from the first communication interface section 78, and the release mode is returned to the examination mode. When the replay is not a message cf normal end, the first communication interface section 78 transmits a message of abnormal end, and the mode is moved to the examination mode.

Figure 33A:
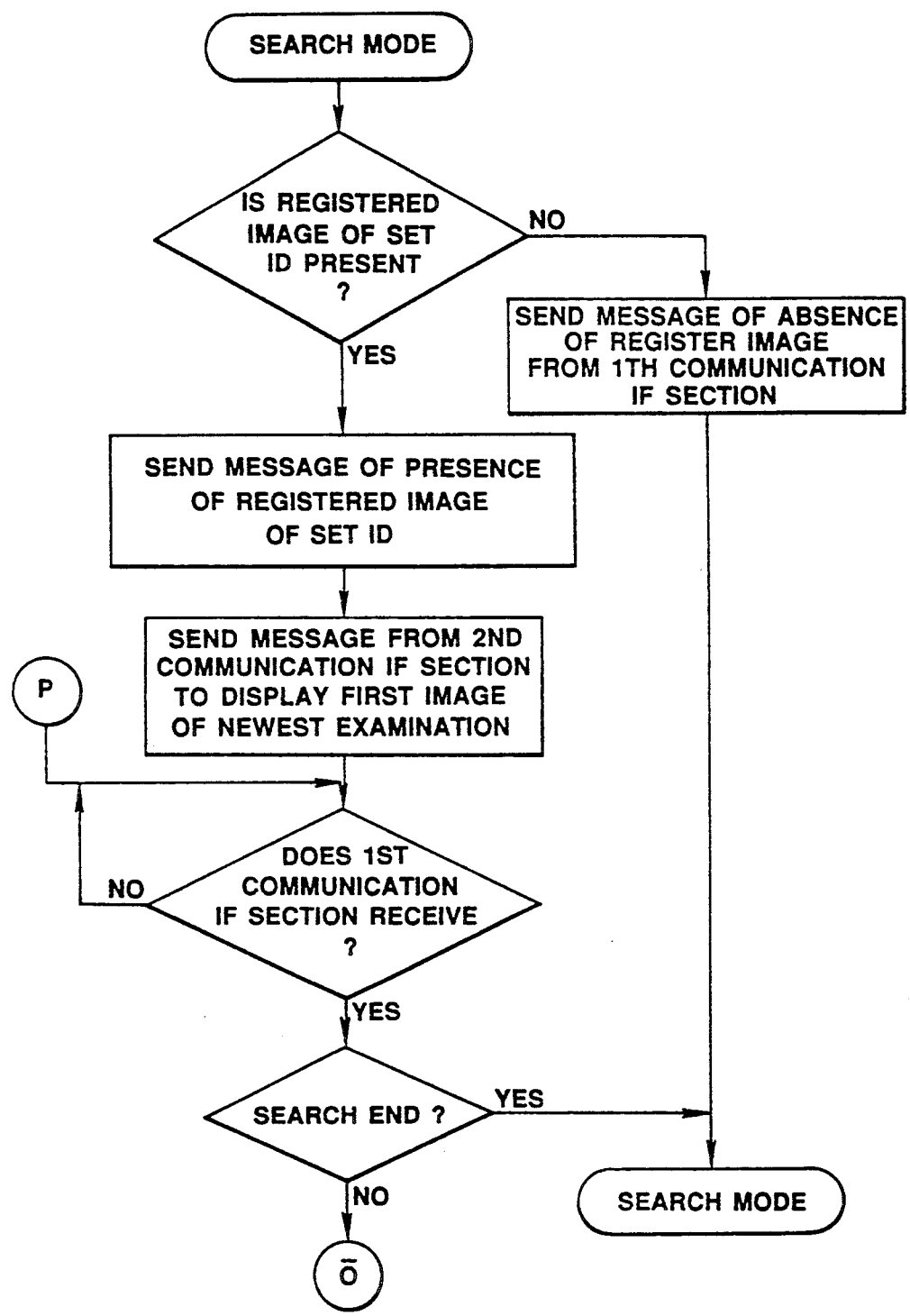
FIGS. 33a, 33b are flowcharts which shows the process in a search mode, FIGS., and 34a, 34b are explanatory views which show the processing states of each of the sections in the first embodiment.

In the search mode shown in FIG. 33a, a decision is first made as to whether or not there is the registered image of the set ID. When there is no registered image, the first communication interface section 78 sends a message of the absence of the registered image, and the search mode returns to the examination mode.

While when there is the registered image, a message of the presence of the registered image of the set ID is transmitted, and the second communication interface section 79 then sends a direction to the optical disk recorder 72 so that the first image of the newest examination is displayed, and the first communication interface section 78 waits for data input. The sending of the direction causes the optical disk recorder 72 to output the first image.

When data is input to the first communication interface section 78, a decision is made as to whether or not the data is a message of search end. In the case of YES, the search mode is moved to the examination mode, while in the case of NO, the processing shown in FIG. 33b is performed.

Figure 33B:
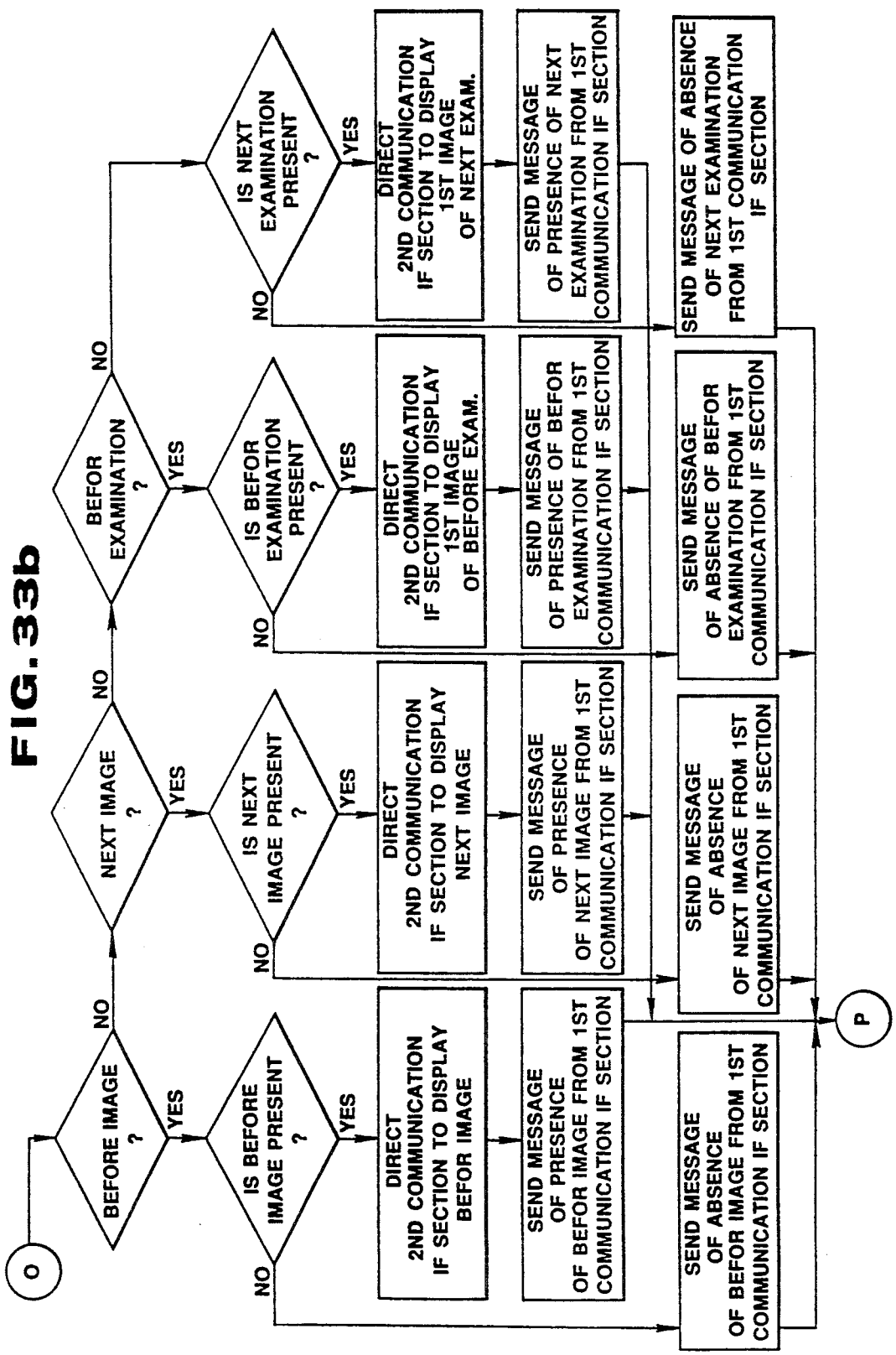

In the case of NO, as shown in FIG. 33b, since the message indicates the search for the before image, the next image, the before examination or the next examination, a decision is made on each of the directions.

For example, in the case of a message of the search for the before image, a decision is made as to whether or not there is the before image to be searched for. When it is decided that there is the before image, the second communication interface section 79 gives a direction to the optical disk recorder 72 so that the before image is displayed (regenerated). The second communication interface section 79 causes the optical disk recorder 72 to output the image, and at the same time, the first communication interface section 78 sends a message of the presence of the before image to the image FIF apparatus 3 (so that the image is displayed on the color monitor 16I connected to each image input apparatus 15I) and then waits for input of data therein. When there is no before image, a message of the absence of the before image is transmitted from the first communication interface section 78 to the side of the image FIF apparatus 3, and the first communication interface section 78 returns to a state wherein it waits for input of the next data.

Since the search for the next image, the before examination and the next examination is performed by the same processing as that described above, it is not described below.

Figure 34B:
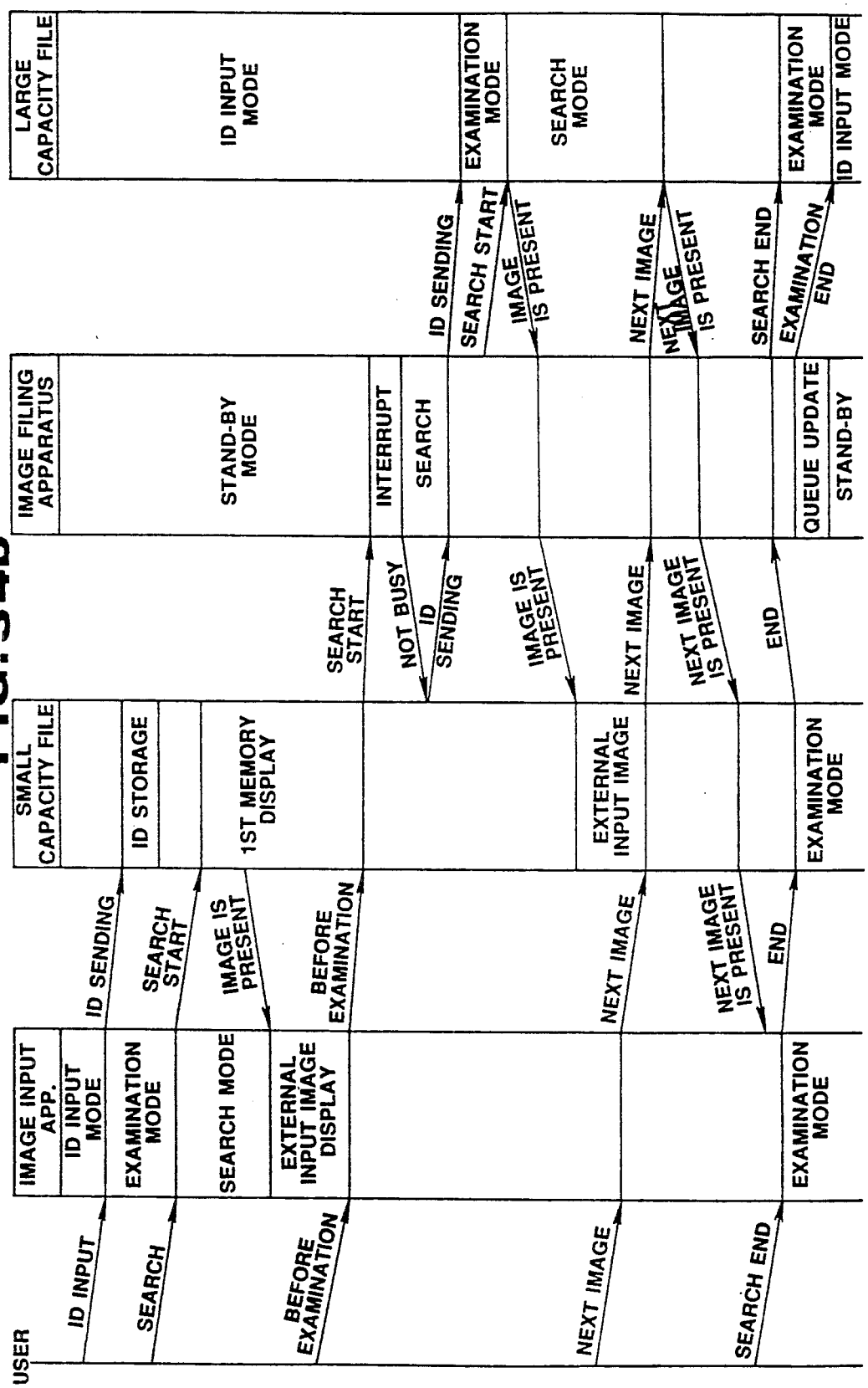

A description will now be given of a typical example of he operation of the first embodiment with reference to FIGS. 34a, 34b.

FIG. 34a shows the processes of starting search, imaging (releasing) and then completing the search.

In the drawing, when the user inputs the ID data, each image input apparatus 15I is moved from the ID input mode to the examination mode, as well as the input ID being sent to each small capacity image filing apparatus 17I through the communication line and stored therein. When the user then performs a release operation, each image input apparatus 15I is moved to the release mode in which the release signal is transmitted to each small capacity image filing apparatus 17I and written in the first frame memory section 44-1. When the writing is normally performed, a message of the normal end is transmitted to each image input apparatus 15I through the communication line, and the image input apparatus 15I returns to the examination mode. When a release operation is further carried out, the same processing in which the release image is written in the next frame memory section 44-2 is repeated. When the data input section 36 gives a direction of the examination end, each image input apparatus 15I is moved to the ID input mode, and at the same time, a message of the examination end is sent to each small capacity image filing apparatus 17I, and the mode is moved to the registering mode.

In this registering mode, each small capacity image filing apparatus 17I sends a message of the registering start to the image FIF apparatus 3, and the STAND-BY mode is moved to the interrupt processing mode. When an interruption is accepted, a not busy message is sent to each small capacity image filing apparatus 17I, the mode is moved to the image registering mode in which the ID of the patient whose image to be registered is received. When the ID is received, the ID is transmitted as it was to the large capacity image filing apparatus 4 in which the ID is stored, and the ID input mode is then moved to the examination mode.

Each small capacity image filing apparatus 17I outputs the image data stored in the first frame memory section 44-1, as well as sending a release message to the large capacity image filing apparatus 4 through the image FIF apparatus 3, so that the output image data is recorded in the apparatus 4. In the case of normal recording, the large capacity image filing apparatus 4 sends a message of OK (normal end) to each small capacity image filing apparatus 17I through the image FIF apparatus 3. When the message is received, the image data in the next frame memory section 44-2 is output and recorded in the large capacity image filing apparatus 4. In this way, the image data for a single examination recorded in each small capacity image filing apparatus 17I is output to the large capacity image filing apparatus 4 and recorded therein. When the image data for a single examination is recorded, each small capacity image filing apparatus 17I sends a message of the registering end to the image FIF apparatus 3 which is moved to the queue processing mode and which sends a message of the examination end to the large capacity image filing apparatus 4. When the examination registering is completed, the ID mode is established. The image FIF apparatus 3 is moved to the STAND-BY mode after the queue processing.

A description will now be given of the operation in a case in which search is the performed after the examination has been started and is then completed with reference to FIG. 34b.

When the user inputs a message of search after the ID input, each image input apparatus 15I is moved from the examination mode to the search mode, as well as sending a message of the search start to each small capacity image filing apparatus 17I. If a release operation is performed before each small capacity image filing apparatus 17I receives the message, a signal representing the presence of the image is returned, and the image in the first frame memory section 44-1 is output so that it can be displayed. Each image input apparatus 15I is switched from an image display state of internal input to an image display state of external input so that the image of the first frame memory section 44-1 is displayed.

When a message for the before examination is then input to the data input section 36 from each image input apparatus 15I, the message for the before examination is sent to each small capacity image filing apparatus 17I. The small capacity image filing apparatus 17I sends a message of the search start to the image FIF apparatus 3, the interrupt processing mode is established. When the mode before the interruption is the STAND-BY mode, a Not busy message is sent to the small capacity image filing apparatus 17I. When the small capacity image filing apparatus 17I receives the message, it sends the ID data and causes the large capacity image filing apparatus 4 to receive the ID data through the image FIF apparatus 3. When the large capacity image filing apparatus 4 receives the ID, it is moved from the ID input mode to the examination mode. When the large capacity image filing apparatus 4 receives a message of the search start after it has received the ID, the examination mode is moved to the search mode in which the image of the ID is searched for. When there is the image, a message of the presence of the image is returned to the small capacity image filing apparatus 17I through the image FIF apparatus 3. When the small capacity image filing apparatus 17I receives the message, the external input image side thereof is selected so that the image is output to the side of the image input apparatuses 15I and the searched image is displayed on the color monitor 16I.

For example, when the user then inputs a direction of the search for the next image, the direction is transmitted from each image input apparatus 15I through each small capacity image filing apparatus 17I and the image FIF apparatus 3 to the large capacity image filing apparatus 4 in which the next image is searched for. When there is the next image, a message of the presence of the next image is sent to each image input apparatus 15I through the image FIF apparatus 3 and the small capacity image filing apparatus 17I. At the same time, the large capacity image filing apparatus 4 outputs the image to the image input apparatus 15I through the image FIF apparatus 3 and the small capacity image filing apparatus 17I so that the next image is displayed on the color monitor 16I.

After the search has been performed in the above-mentioned manner, when a direction of the search end is given, the image input apparatus 15I is returned to the search mode, and a message of the search end is sent through the small capacity image filing apparatus 17I and the image FIF apparatus 3 to the large capacity image filing apparatus 4 which is moved from the search mode to the examination mode. The image FIF apparatus 3 sends a message of the examination end to the large capacity image filing apparatus 4 after a message of the search end, then performs the queue update processing and is then moved to the STAND-BY mode. When the large capacity image filing apparatus 4 receives a message of the examination end, it returns to the ID input mode.

In the first embodiment which operates in above-mentioned manner, the image input apparatus 15I are respectively connected to the small capacity image filing apparatuses 17I having the frame memory sections 44-1, 44-2, . . . 44-40 for temporarily storing a plurality of images so that the data of an image obtained by each electronic scope 13I and the image information thereof can be recorded for a single examination.

In addition, each small capacity image filing apparatus 17I is connected to the common large capacity image filing apparatus 4 through the image FIF apparatus 3 so as to send a message of the examination end of a single examination, which is sent from the side of a plurality of small capacity image filing apparatuses 17I connected to the image FIF apparatus 3, to the large capacity image filing apparatus 4 and cause the ID data and the patient data of the examination and the image data thereof to be registered in the apparatus 4. In this way, the first embodiment enables the simultaneous use of a plurality of image input means, as well as enabling collective registering of the image data for a single examination, which has been completed, in the common large capacity image filing apparatus 4.

Further, in the case of search for an image, it is possible to access the large capacity image filing apparatus 4 through the image FIF apparatus 3 and to perform the search for the image by using the large capacity image filing apparatus which is common to the image input apparatuses 15I. In this case, since the large capacity image filing apparatus 4 serves to collectively control the image information and the image data input from a plurality of image input apparatuses 15A, 15B, . . . , a desired image can be searched for a time which is shorter than in a case in which data is divided and controlled by separated apparatuses.

The first embodiment also enables a plurality of images (in some cases, a single image) for a single examination to be sequentially recorded on a continuous track or sector and thus enables the simplification of the control structure of the data base. For example, it is sufficient to record only the first image track number (including sector) and the final track number, without the need for holding data such as the track numbers for the intermediate images.

Further, desired image data can be accessed for a time which is shorter than with random file control in which image data is recorded for one page.

In addition, in the first embodiment, the image FIF apparatus 3 is connected to a plurality of small capacity image filing apparatuses 17I and interposed between these apparatuses 17I and one large capacity image filing apparatus 4 so that a plurality of image input apparatuses 15I can be simultaneously used.

In other words, since the prior art has a configuration in which one image input apparatus 15I is connected to a large capacity image filing apparatus 4 through a small capacity image filing apparatus 17I or directly, it is possible to image and search only in the unit of a single apparatus (single). However, the first embodiment also has an advantage in that the interposition of the image FIF apparatus 3 enables simultaneous imaging and searching by a plurality of image input apparatuses 15I.

FIG. 35 shows an image input/filing apparatus 2B' in a modification of the first embodiment of the present invention. In this modification, for example, the image input/filing apparatus 2B comprising the electronic scope 13B in the image filing apparatus 1 shown in FIG. 5 is replaced by the image input/filing apparatus 2B' which comprises a scope 254 with an external television camera in which a television camera 253 is mounted on a fiberscope 252.

FIG. 36 shows the configuration of the scope 254 with an external television camera.

In the fiberscope 252, the CCD 26 is not disposed on the focal surface of the objective lens 25, as in the electronic scope 13A shown in FIG. 5, but one end of an image guide 255 for transmitting optical images is disposed on the focal surface. The image guide 255 has the function of transmitting an optical image to the other end near the ocular portion 256 which is formed at the rear end of the operational portion 20 inserted into the long thin insertion portion 12. An ocular 257 is disposed opposing the other end. In the television camera 253 which can be mounted on the ocular portion 256, an image formation lens 258 is disposed opposing the ocular 257 for the purpose of forming the optical image transmitted on CCD 259. On the imaging surface of the CCD 259 is disposed a mosaic color filter 260 for separating colors. A connector 262 provided at the rear end of a cable 261 of the television camera 253 is connected to the image input apparatus 15B so that a signal subjected to photoelectric conversion in the CCD 259 is processed in the same manner as in the electronic scope 13B.

To the television camera 253 is also provided a release switch 38 so that, when the release switch 38 is turned on, the image signal formed by CCD 259 is stored in the small capacity image filing apparatus 17B.

A light guide cable 263 through which a light guide 21 is inserted is extended from the operational portion 20 of the fiberscope 252, the end of the guide cable being connected to the light source 14B so that illumination light is supplied from the light source 14B.

In this modification, the scope 254 with an external television camera can be used in place of the electronic scope 13B. It is a matter of course that the scope with an external television camera can be used in place of other electronic scopes.

Figure 37:
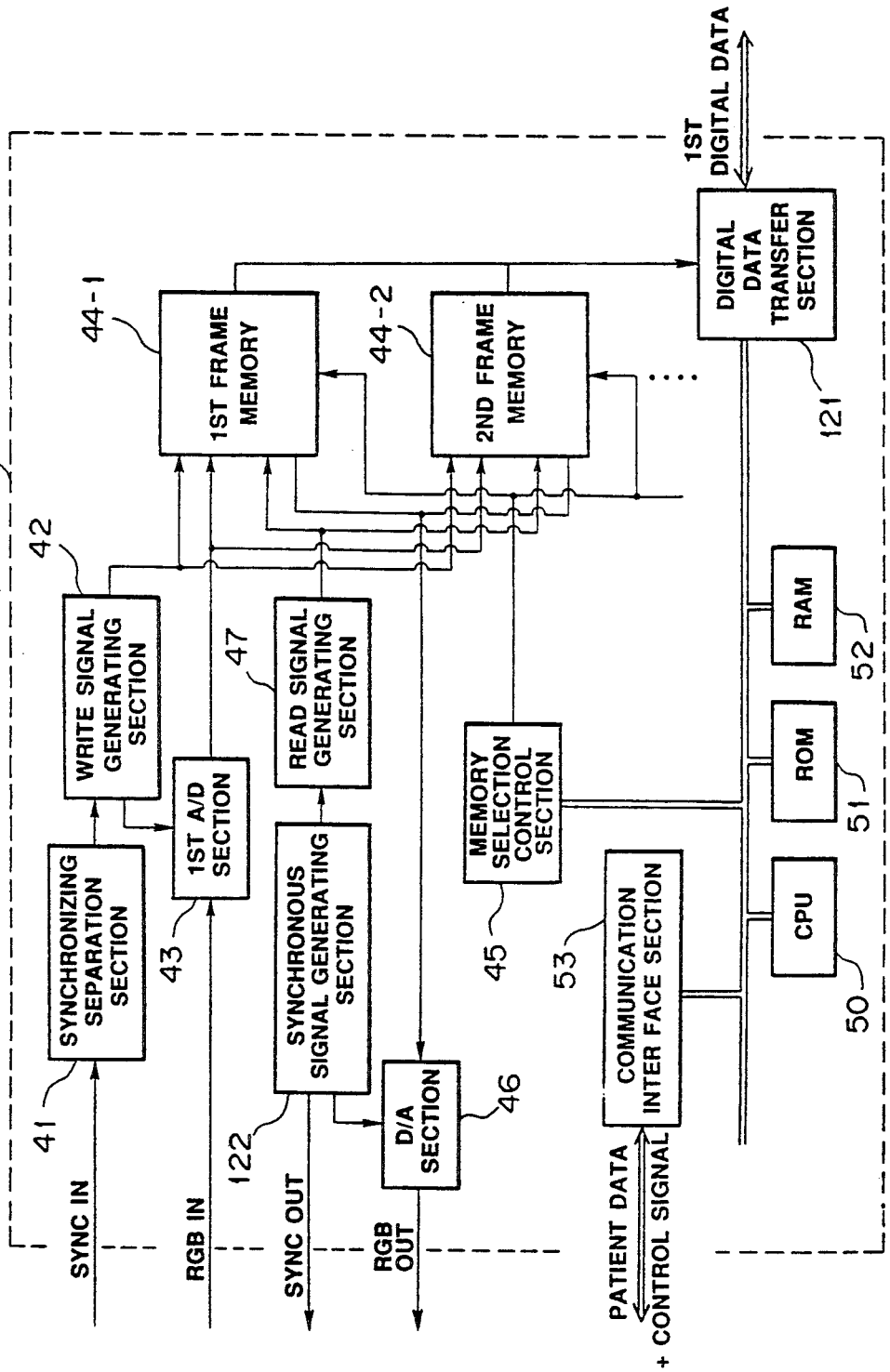
Figure 38:
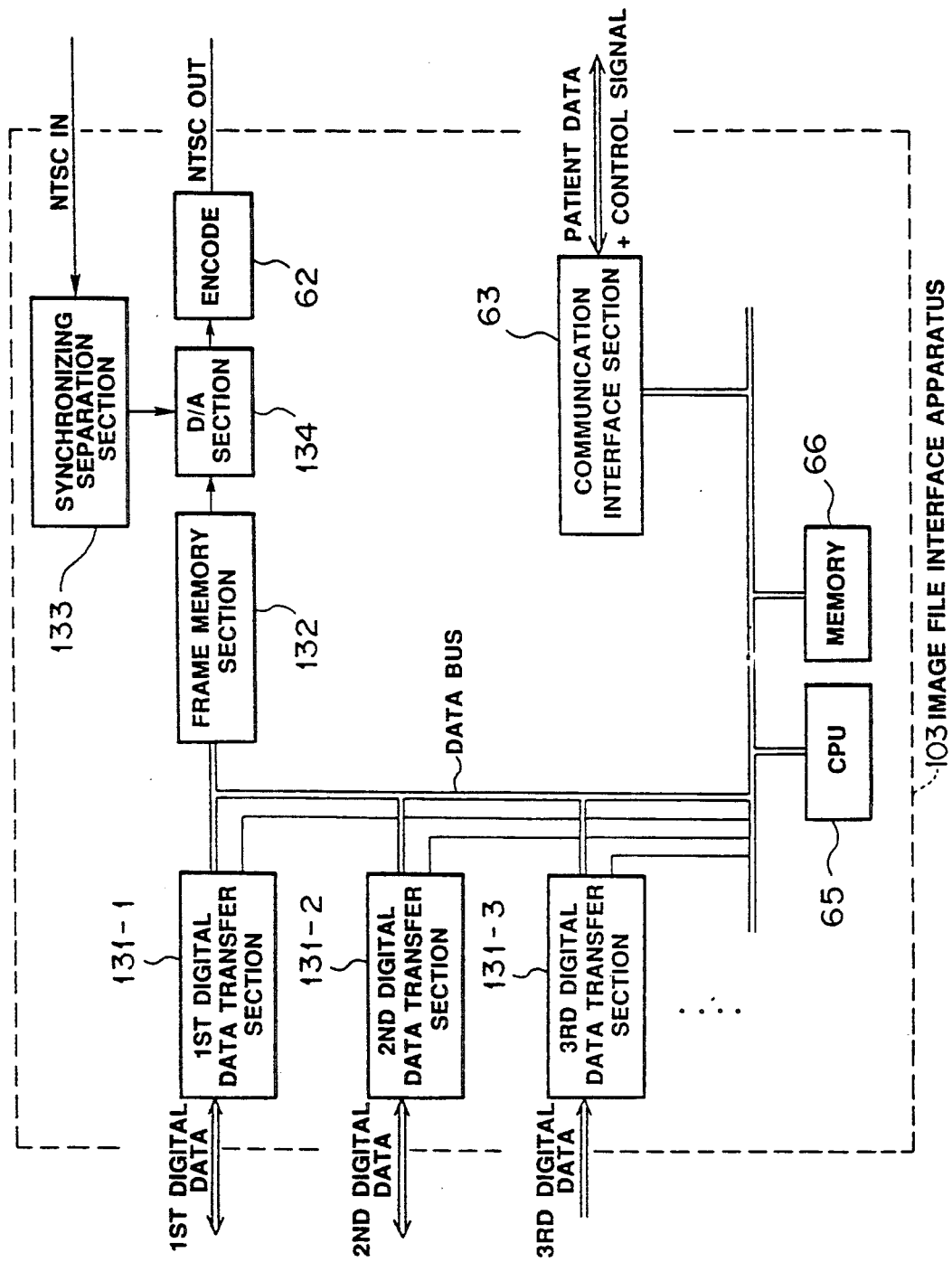

FIG. 37 shows the configuration of each small capacity image filing apparatus 117I in a second embodiment, and FIG. 38 shows the configuration of an image FIF apparatus 103 in the second embodiment.

This embodiment is designed so that data (including control signals) such as the image data and patient data is transmitted by using digital communication from each small capacity image filing apparatus 171 to the image FIF apparatus 3 in the first embodiment.

In the small capacity image filing apparatus 117I shown in FIG. 37, therefore, the output terminals of the frame memory sections 44-i are connected to a digital data transfer section 121 so that image data from each frame memory section 44-i can be transferred to a buffer of the digital data transfer section 121 and transferred to the side of the image FIF apparatus 103. The image data is read in turn from the first frame memory section 44-1 and output and transferred together with the patient data and the control signals.

Each small capacity image filing apparatus 117I contains a synchronous signal generating section 122 for generating a synchronous signal for controlling the operations of a read signal generating section 47 and D/A section 46.

In each frame memory section 44-i, the selection of write or read is controlled by a memory selection control section 45.

The other sections of the small capacity image filing apparatus 117 shown in FIG. 37 are substantially the same as those in FIG. 7, and the same components are denoted by the same reference numerals (only one element is shown without being provided wit the term of "first").

The image FIF apparatus 103 shown in FIG. 38 has a plurality of digital data transfer sections 131-1, 131-2, ... which are disposed in a line so that digital data can be sent to and received from the respective small capacity image filing apparatuses 117A, 117B, ....

The digital data transmitted is divided into the patient data, control data and image data. The image data is written in a frame memory section 132, synchronized with the synchronous signal separated from a synchronizing separation section 133 and then output as an NTSC video signal to the outside (the large capacity image filing apparatus 4) through D/A section 134 and an encoder 62. In this case, synchronous signal generating means may be provided in the frame memory section 132 so as to be synchronized with a synchronous signal.

On the other hand, the patient data and the control data are sent to the external large capacity image filing apparatus 4 through a communication interface section 63. The above-described digital data transfer section 121 may transfer data in either a parallel manner or a serial manner.

The second embodiment enables the compression of digital data and the transfer of the compressed data.

In addition, since image data is sent through a digital circuit, image data can be transmitted to a remote place, and the level of degradation of image data is lower than in the case of a analogue signal because the image data is digital data.

Figure 39:
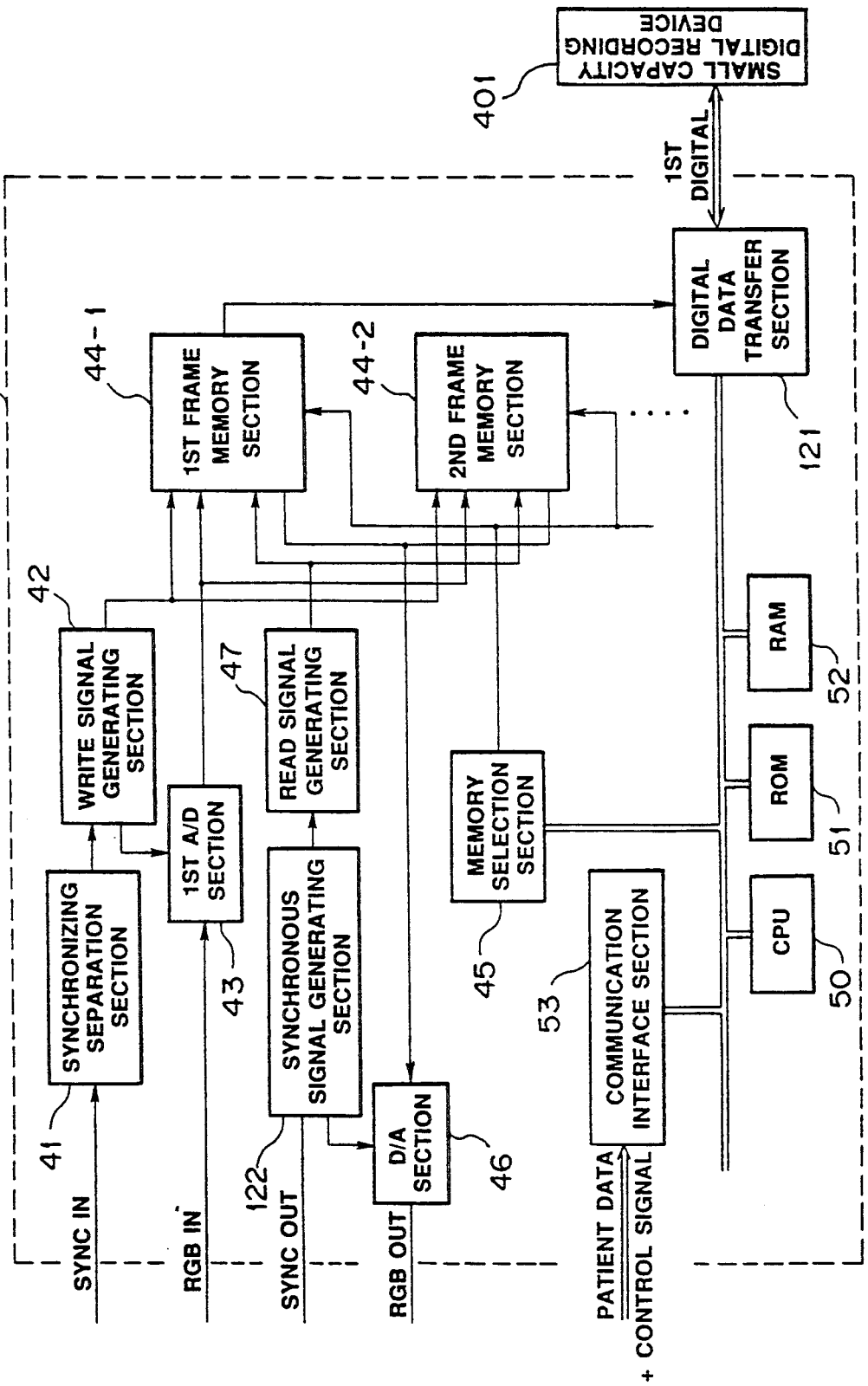
FIG. 39 is a block diagram of the configuration of principal sections in a modification of the second embodiment.

FIG. 39 shows a principal portion of a modification of the second embodiment of the present invention.

Although all of a plurality of small capacity image filing apparatuses 117A, 117B,... are connected to the image FIF apparatus 103 in the second embodiment, only one, for example 117M, of the small capacity image filing apparatus is connected to a small capacity digital recording device 401.

In other words, for example, the image data, ID and patient data for a single examination of the small capacity image filing apparatus 117M are recorded in the small capacity digital recording device 401 which is then connected to a large capacity image filing apparatus 154 so that the contents recorded in the small capacity digital recording device 401 can be transferred, whereby the image data and the data information can be recorded and registered in the data base.

This modification enables the use of image input apparatuses 151 of a number that is greater than the number of the digital data transfer sections 131-i in the image FIF apparatus 103. An image input apparatus used in a case in which image search is scarcely performed, and only a release operation is performed may be separated so that only a release operations can be performed. Further, since it is possible to separately use image input apparatuses, the use is not influenced by the environment thereof.

Figure 40:
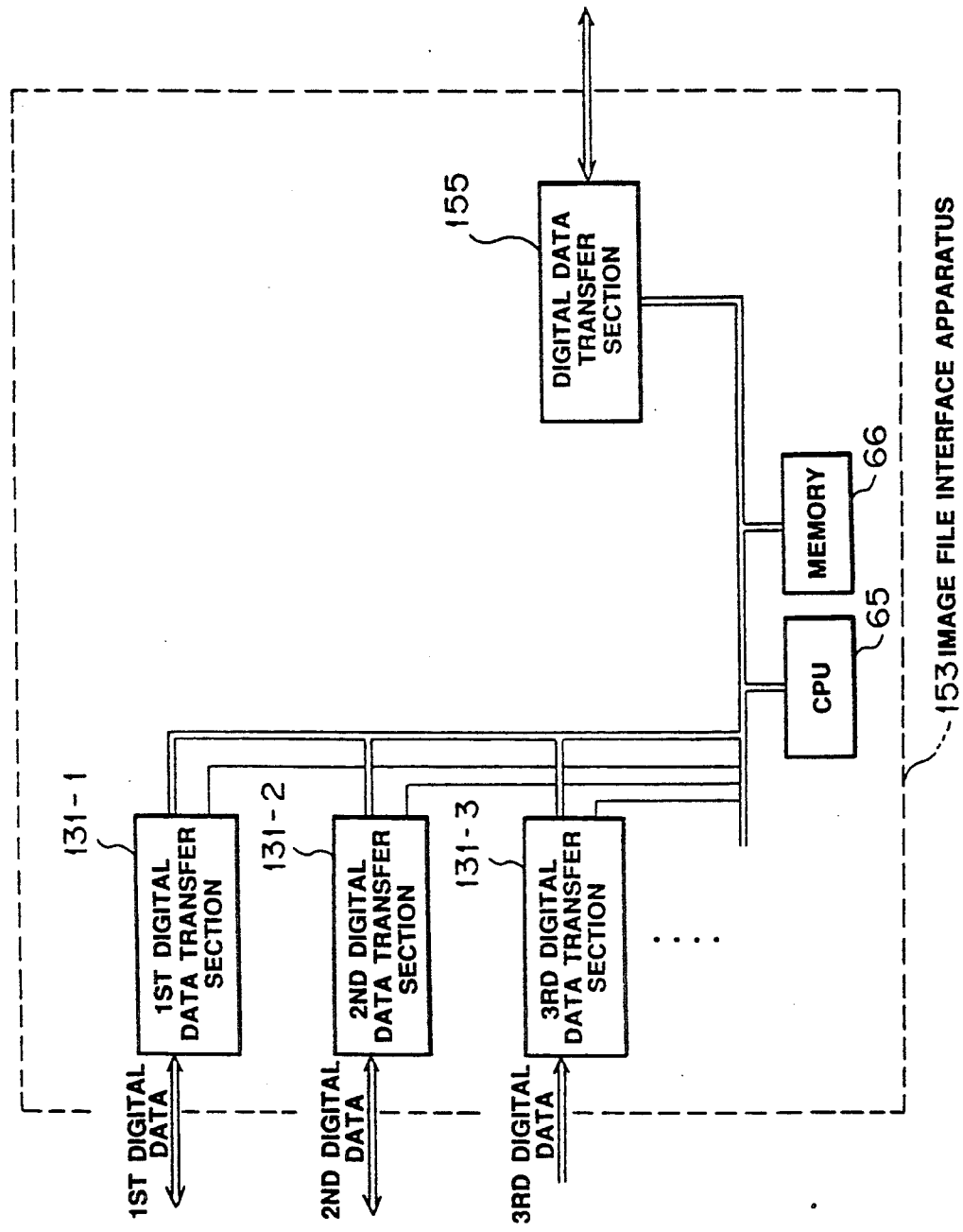
Figure 41:
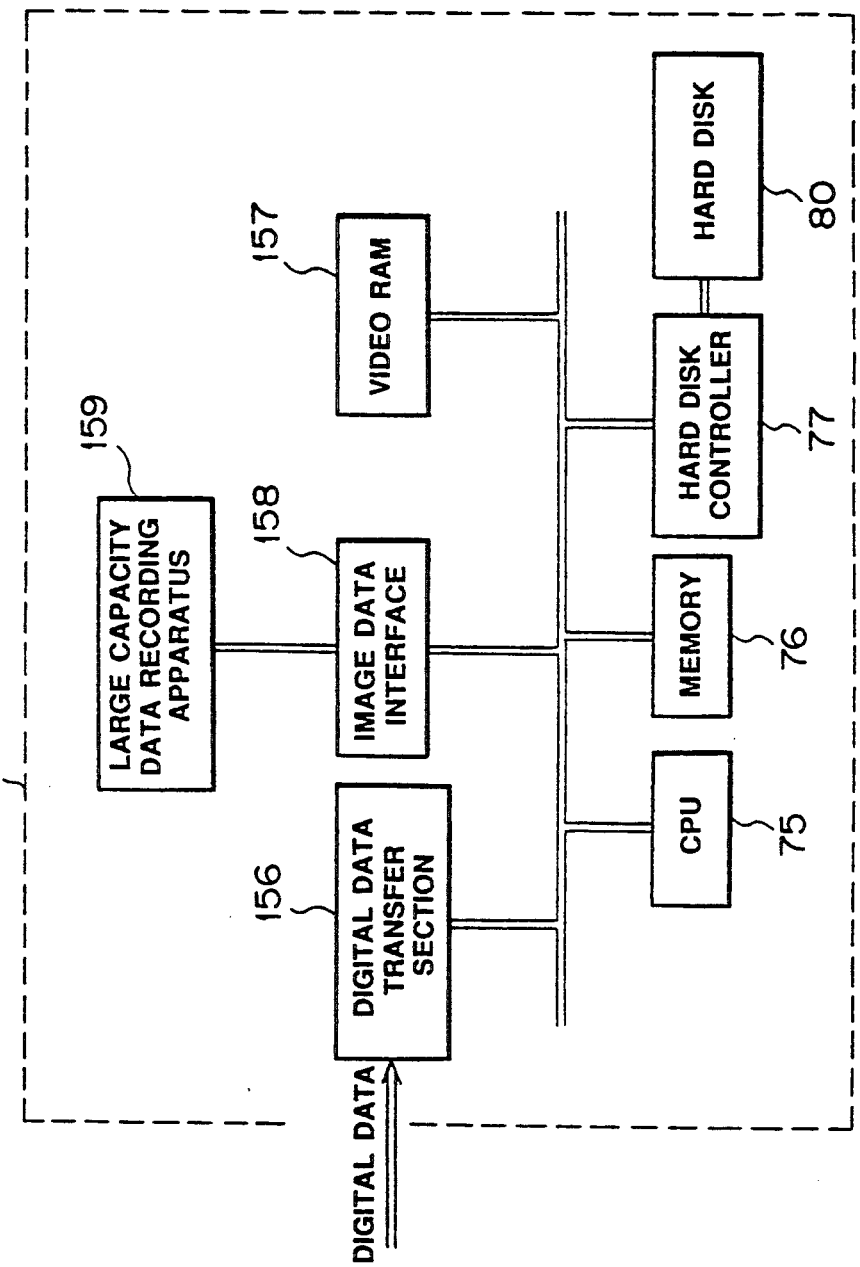

FIGS. 40 and 41 concern a third embodiment of the present invention in which FIG. 40 shows the configuration of an image FIF apparatus 153 in the third embodiment and FIG. 41 shows the configuration of a large capacity image filing apparatus 154 of the third embodiment.

In the third embodiment, the large capacity image filing apparatus in the second embodiment is designed so as to record data therein in a digital manner. Accordingly, in the image FIF apparatus 153, as shown in FIG. 40, a plurality of digital data transfer sections 131-i (i=1, 2, ... N) are connected to a digital data transfer section 155, which transfers digital data to the large capacity image filing apparatus 154, through a bus line.

When digital data is input to each digital data transfer section 131-i, the data is sent from the digital data transfer section 155 to the digital transfer section 156 of the large capacity image filing apparatus 154 shown in FIG. 41 through a digital communication circuit using an instruction from CPU 75.

When the digital data sent is image data, it is written in a video RAM 157 and then recorded in a large capacity digital image data recording device 159 through an image data interface 158.

The indexes such as the patient data and the image data are recorded in a hard disk 80 through a hard disk controller 77 so that images can be registered. The search for an image can be simultaneously effected through the digital communication line.

The third embodiment has the effect of preventing degradation of an image during recording and regeneration of the image because it is further digitized.

Figure 42:
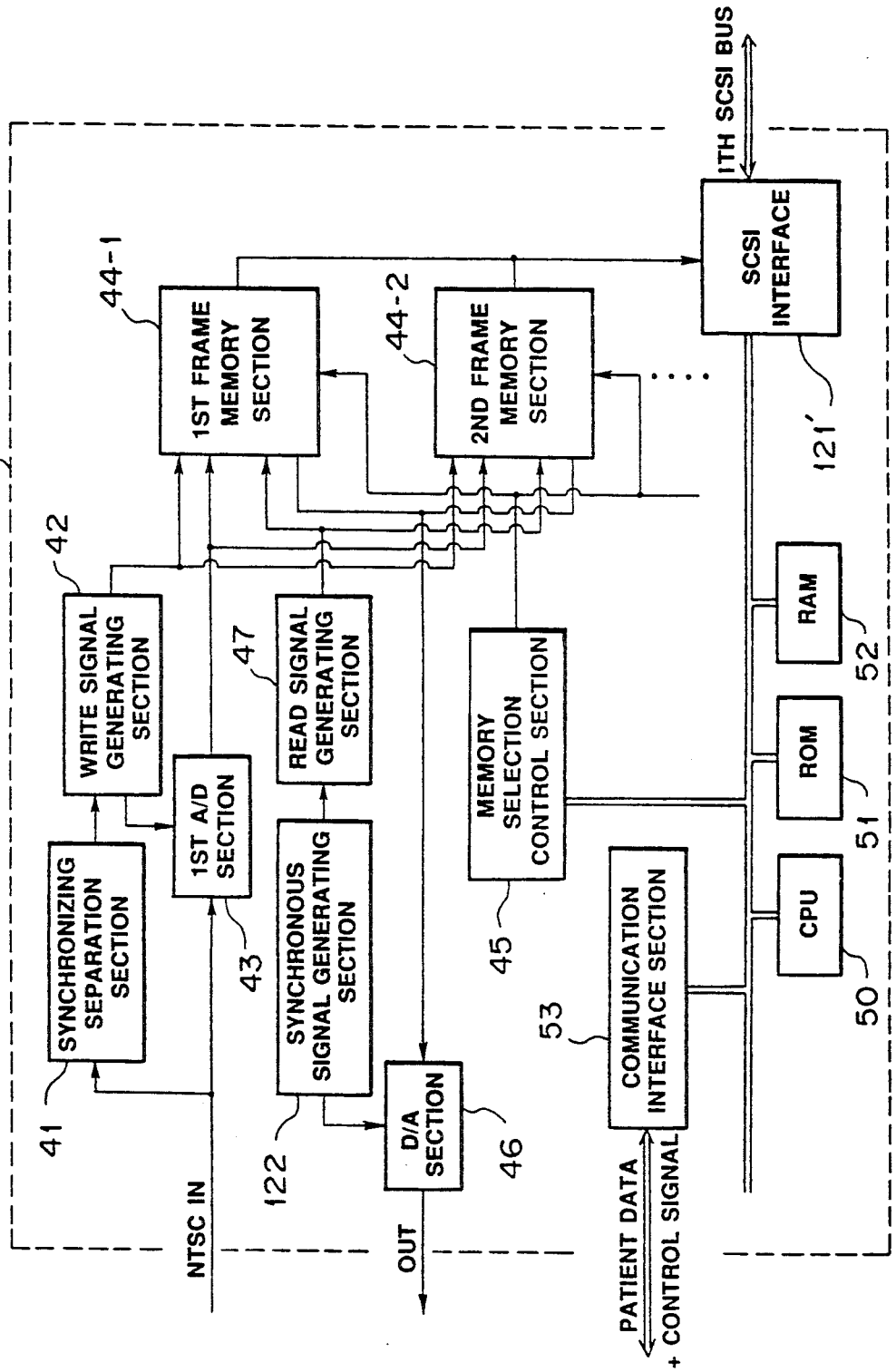
Figure 43:
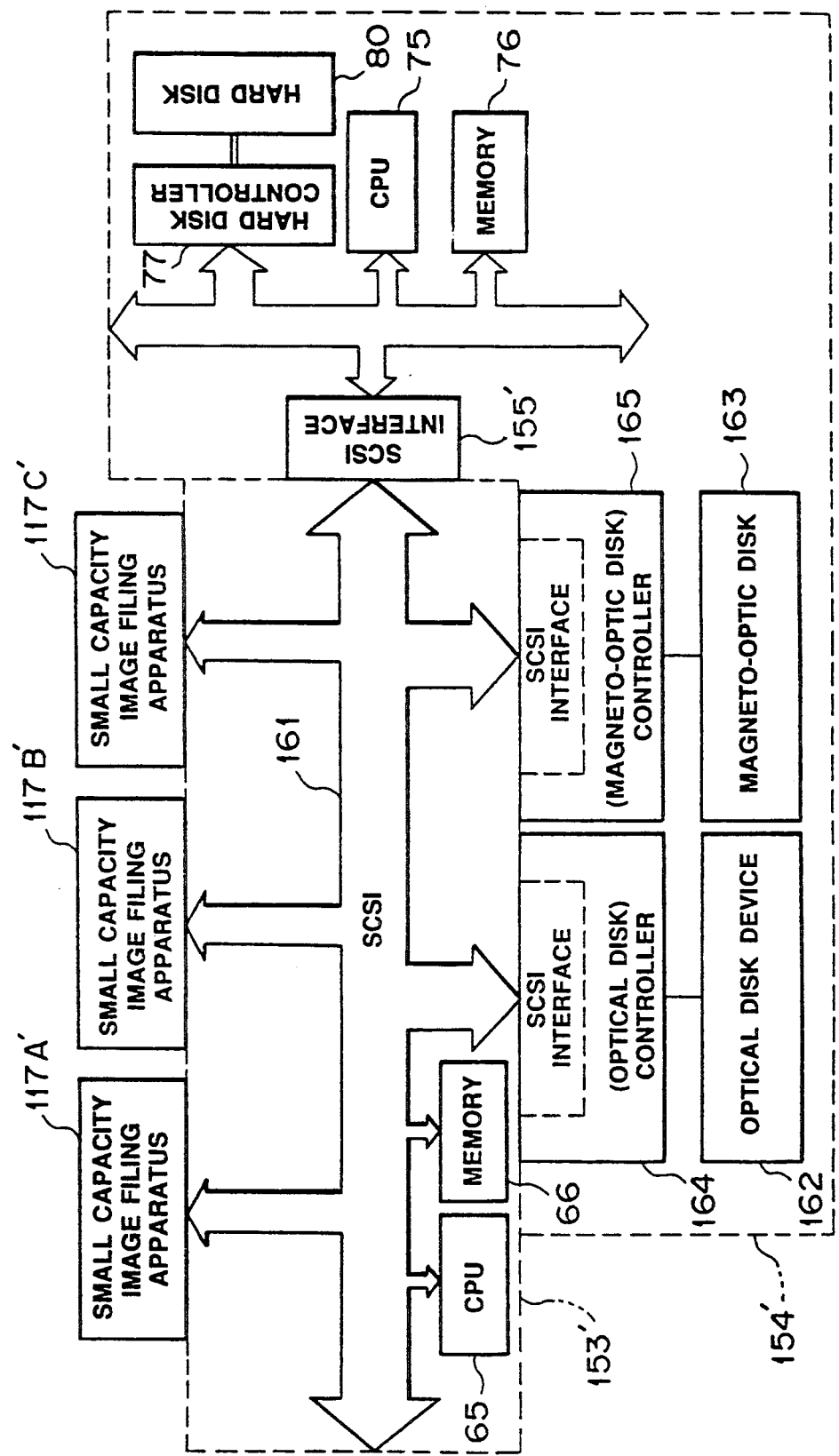

FIGS. 42 and 43 relate to a modification of the third embodiment of the present invention in which FIG. 42 shows a small capacity image filing apparatus 117I' and FIG. 43

In this embodiment, as shown in FIG. 42, a video signal is input and output as an NTSC composite video signal.

An image input/filing apparatus which is connected to each small capacity image filing apparatus 117I' outputs NTSC video signals. Such NTSC video signals are converted into digital signals in a first A/D section 43 and then written in frame memory sections from a first frame memory section 44-1. From the video signals is extracted a synchronous signal component by a synchronizing separation section 41.

Video signals output from each small capacity image filing apparatus 117I' to the image input/filing apparatus are also output as NTSC composite video signals.

On the other hand, data transfer between each small capacity image filing apparatus 117I' and the large capacity image filing apparatus 154' through the image FIF apparatus 153' is data transfer in a digital manner in the same way as in the third embodiment. In this case, each of the small capacity image filing apparatuses 117I' has an SCSI interface 121' so that data is transferred to the image FIF apparatus 153' through an SCSI bus 161 which is connected to each small capacity image filing apparatus 117I' through the SCSI interface 121', as shown in FIG. 43. In addition, the image FIF apparatus 153' is connected to the large capacity image filing apparatus 154' provided with an SCSI interface 155' or the like.

The large capacity image filing apparatus 154' is provided with as image digital recording means, for example, an optical disk device 162 and a reloadable magneto-optic disk 163, controllers 164, 165 therefor being connected to the SCSI bus 161 through SCSI interfaces 166, 167, respectively.

This modification has the same advantage as that of the third embodiment, as well as having generality because data is transferred by employing SCSI which is a standard specification.

Figure 44:
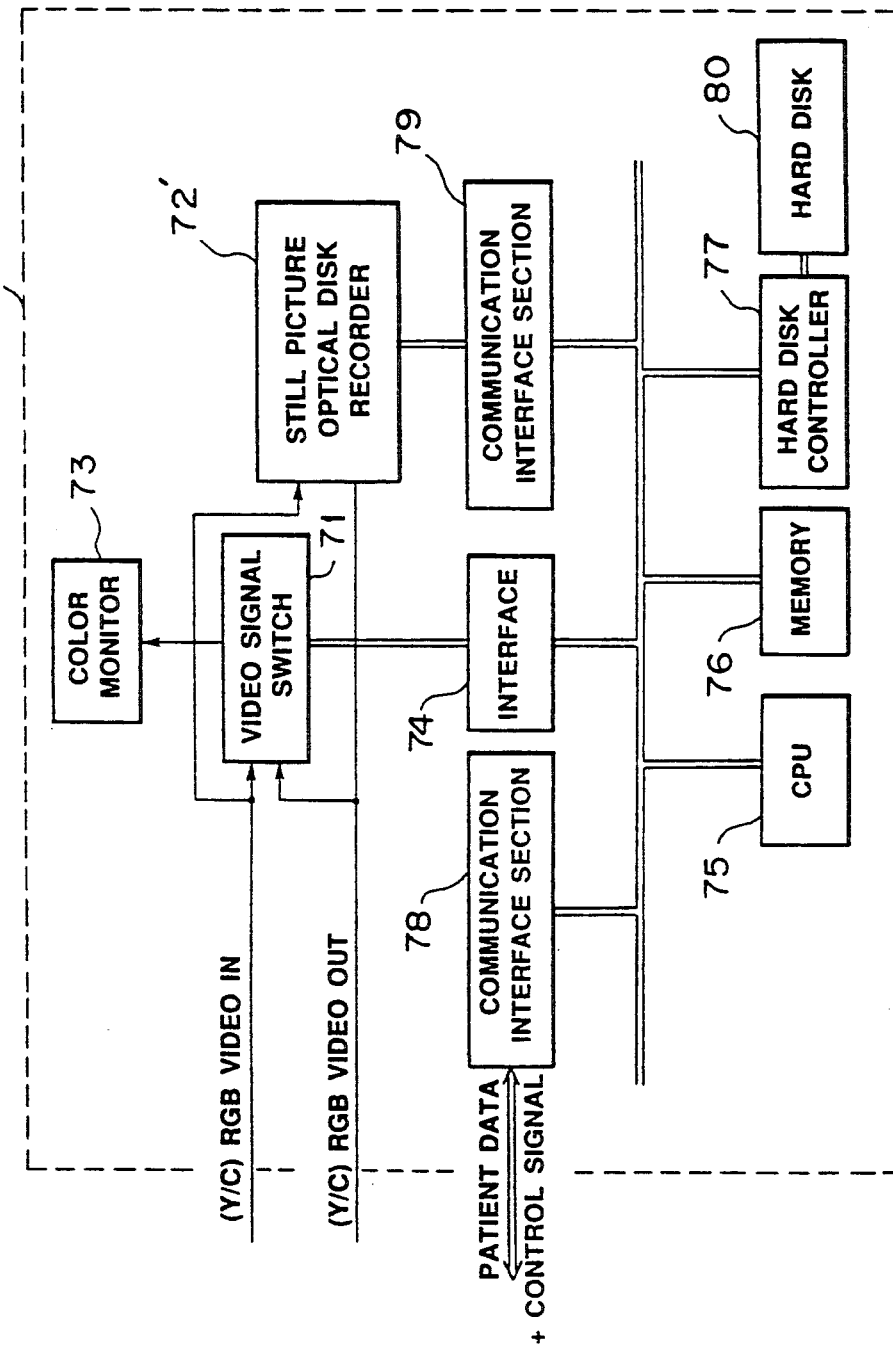
FIG. 44 is a block diagram of a large capacity image filing apparatus in a fourth embodiment of the present invention.

FIG. 44 shows the configuration of a large capacity image filing apparatus 204 in a fourth embodiment of the present invention.

In this embodiment, the (sill picture recording) optical disk recorder 72 in the first embodiment which performs recording and regenerating of composite video signals is replaced by an optical disk recorder 72' which performs recording and regenerating of RGB signals.

The large capacity image filing apparatus 204 therefore outputs RGB video signals so that signals output from the RGB signal switch 61 shown in FIG. 7 is input to the image FIF apparatus without passing through the encoder 62.

This embodiment produces images of high quality, as compared with recording and regeneration by NTSC composite video signals.

As shown in parentheses in FIG. 44, an intensity signal Y and a color difference signal R-Y, B-Y (represented by C) may be separately transmitted in place of RGB primary color signals. This case also enables the transmission of images of high quality, as compared with composite video signals.

Figure 45:
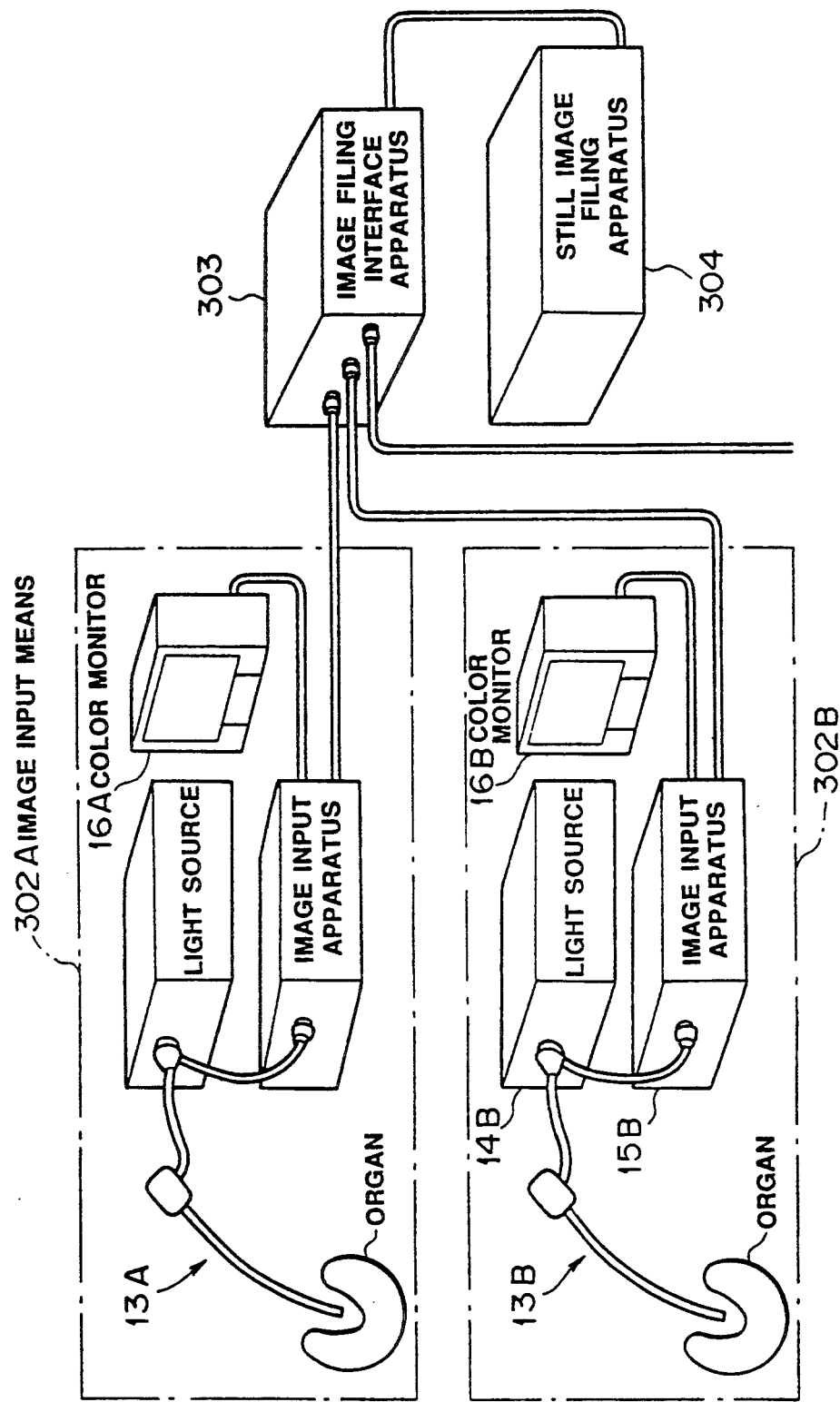
Figure 46:
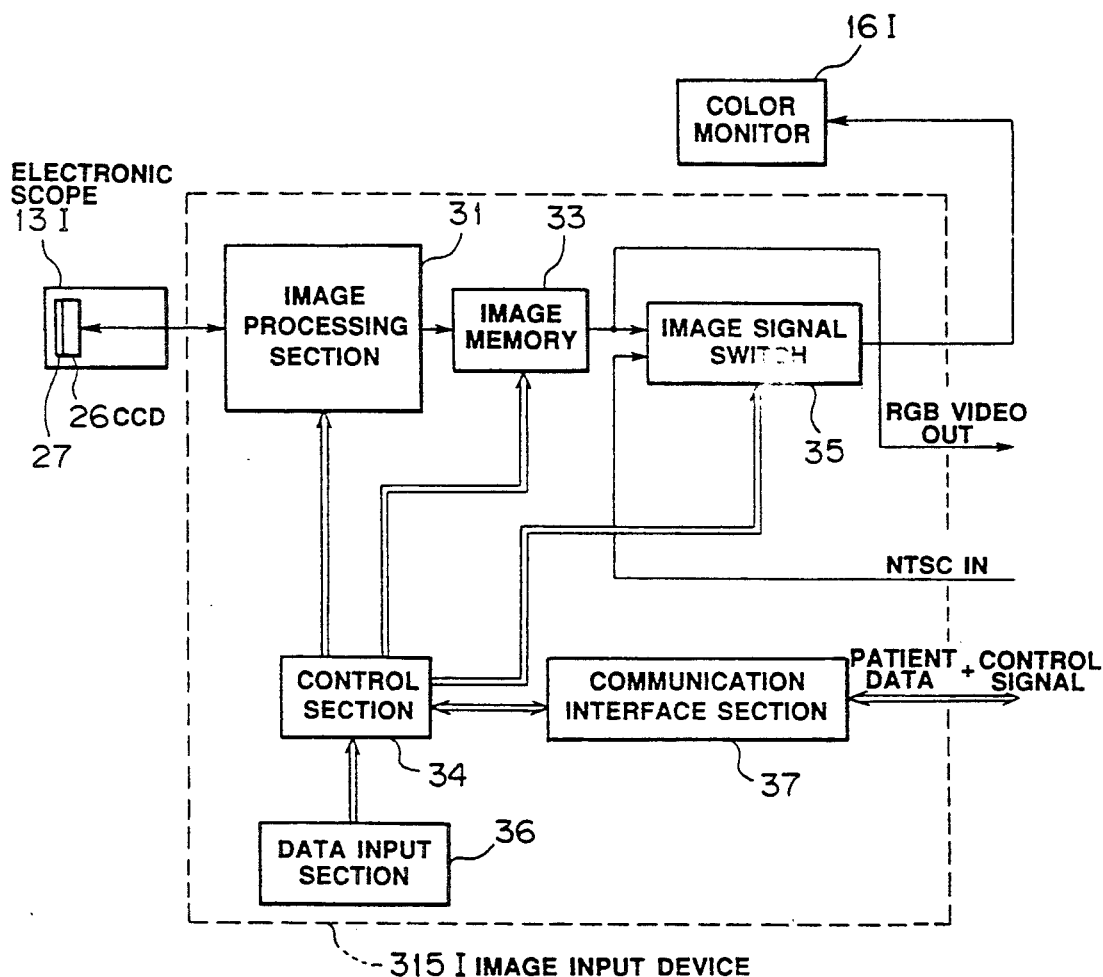
Figure 47:
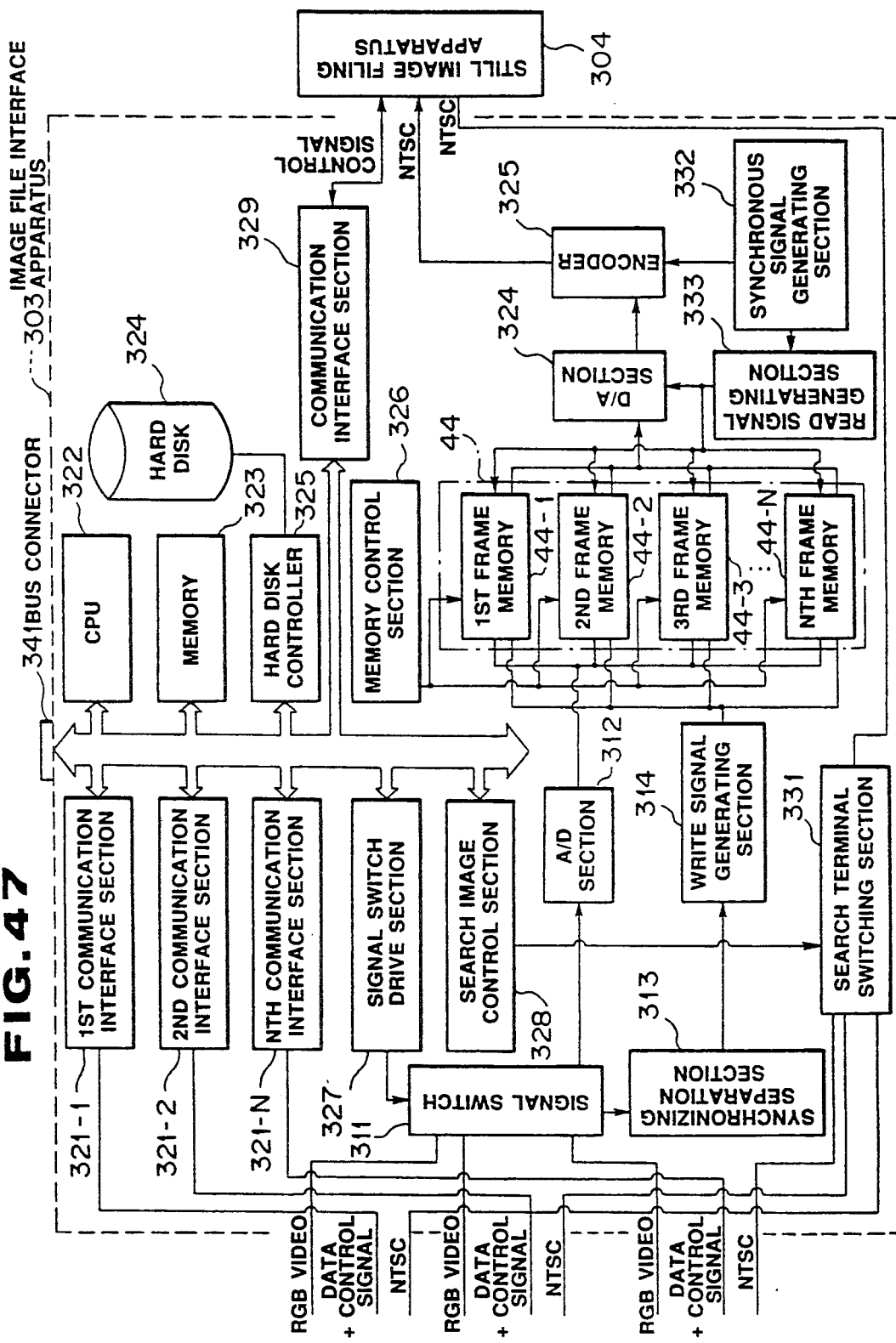

FIGS. 45 to 47 relate to a fifth embodiment of the present invention in which FIG. 45 shows an image filing apparatus 301 in the fifth embodiment, FIG. 46 shows the configuration of each image input apparatus 315I in the fifth embodiment and FIG. 47 shows the configuration of an image FIF apparatus 303 in the fifth embodiment.

This embodiment is designed so that one image FIF apparatus 303 has the functions of the small capacity image filing apparatus 17I and the image FIF apparatus 3 in the first embodiment shown in FIG. 5.

In the first embodiment, the images of a single examination are temporarily stored in a plurality of frame memory sections 44-1, . . . , 40 in each small capacity image filing apparatus 17I and then sent to the large capacity image filing apparatus 4 by switching signals by the RGB signal switch 61. In this embodiment, however, images are stored in turn in the common frame memory 44 from the first frame memory 44-1 in the order of release from the image input apparatuses 15I.

As shown in FIG. 45, the image filing apparatus 301 comprises a plurality of image input means 302A, 302B, . . . and an image FIF apparatus to which the image input means are connected, and a still picture filing apparatus 304 which is connected to the image FIF apparatus 303.

Figure 1:
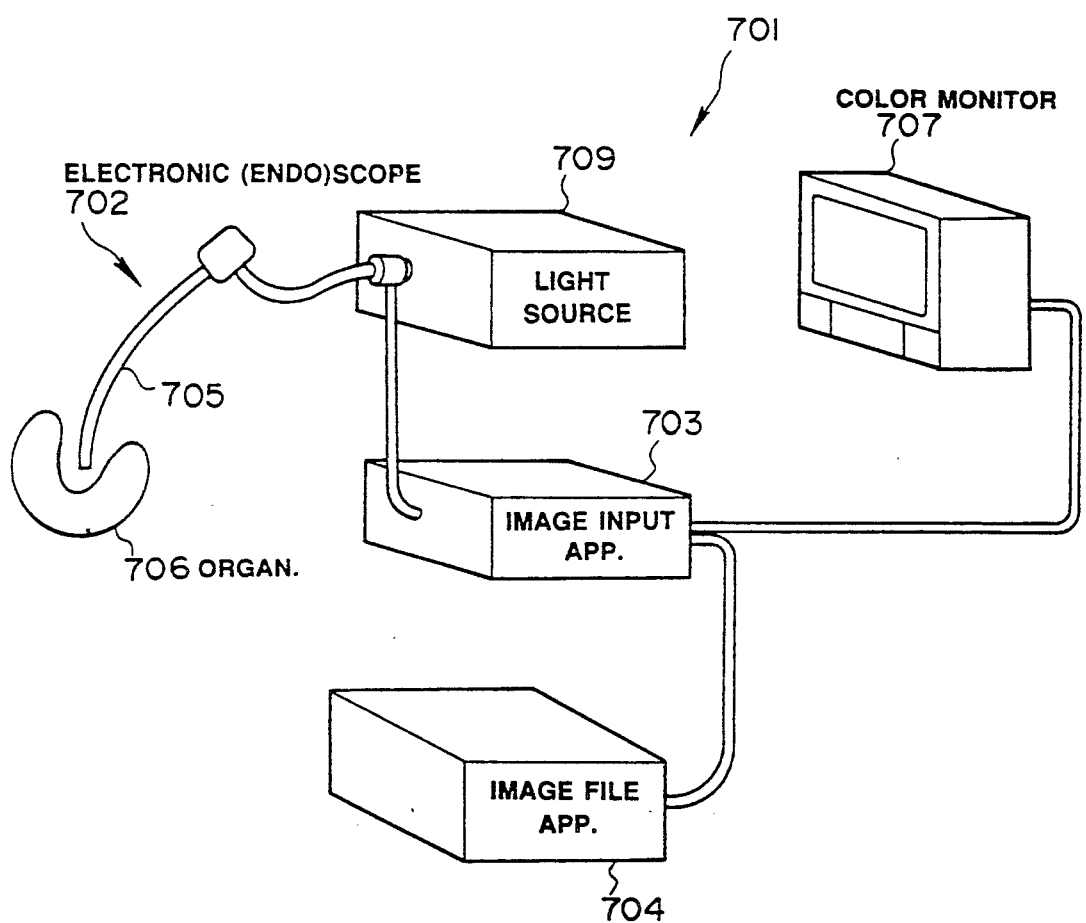
Figure 2:
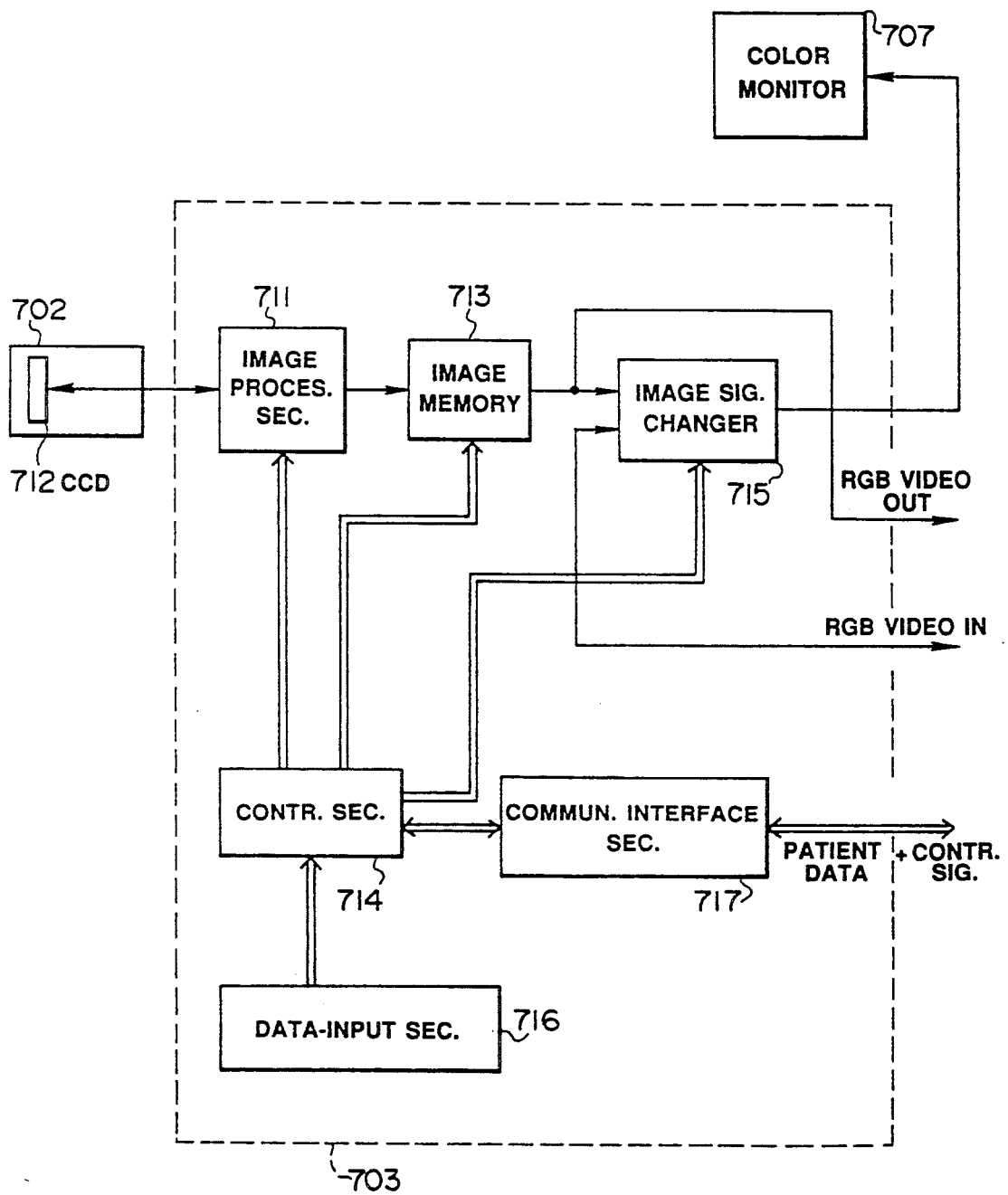
Figure 3:
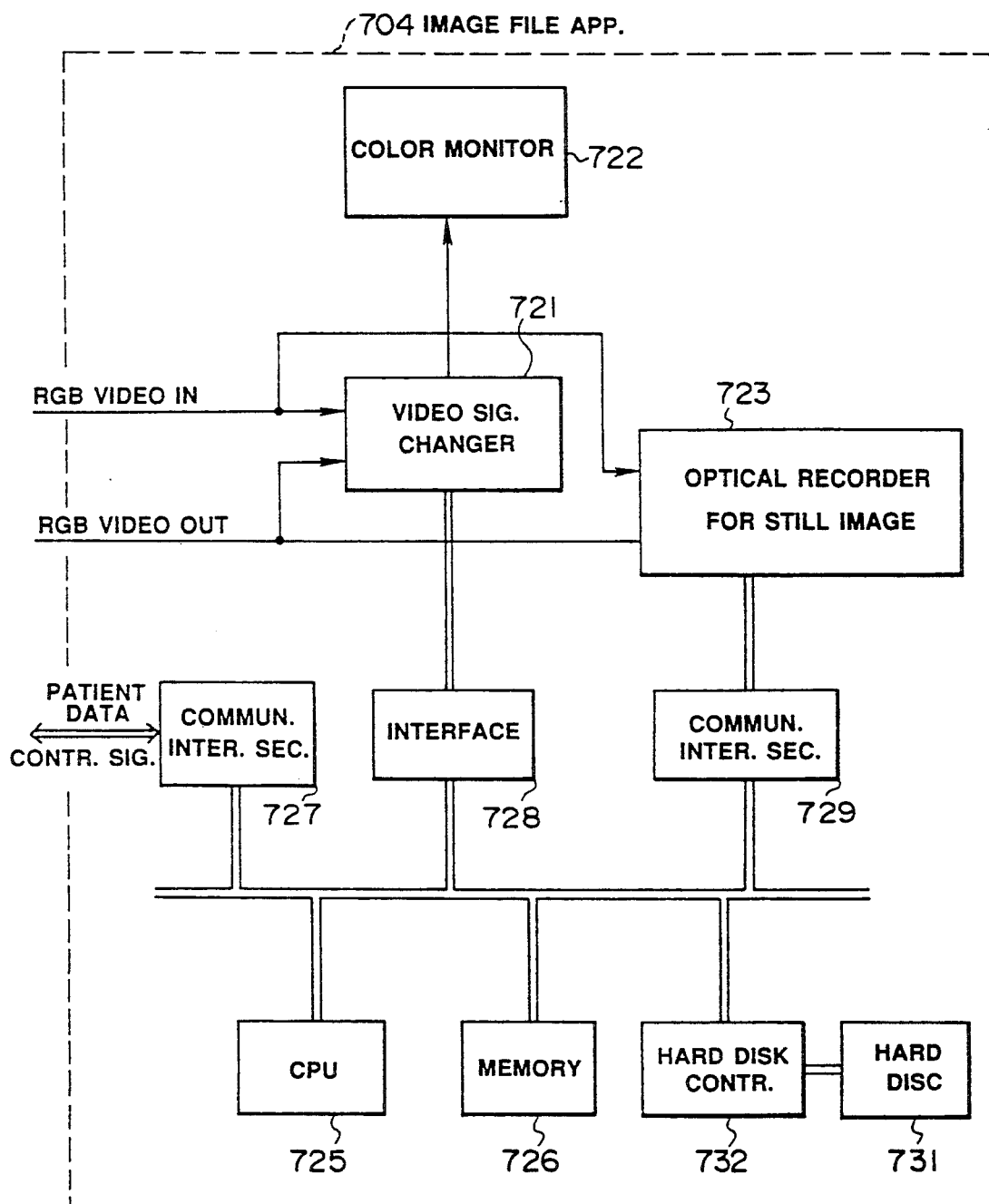

Each of the image input means 302I (I=A, B, . . . ) has a configuration which is substantially the same as each image input/filing apparatus 2I shown in FIG. 1 except for each small capacity image filing apparatus 15I. Thus, the same sections are denoted by the same reference numerals.

That is, each electronic scope 13I, each light source 14I and each color monitor 16I are completely the same as those shown in FIG. 1, and each image input apparatus 15I is different from that shown in FIG. 1 in the point that the video signals input from the outside are NTSC composite video signals, as shown in FIG. 46.

On the other hand, the image FIF apparatus 303 which is connected to each image input apparatus 15I has the configuration shown in FIG. 47.

A plurality of RGB video signals input are input to a signal switch 311, and RGB signal components selected in the signal switch 311 are converted into digital signals by A/D section 312 and then input to the frame memory section 44 comprising a first, second,. . . .Nth frame memories 44-1, 44-2, . . . 44-N. The SYNC signal components in the RGB video signals are input to a synchronizing separation section 313 in which the signal components are divided into horizontal and vertical synchronous signals. The synchronous signals are then input to a write signal generating section 314 so as to actuate the A/D section 312 using a conversion clock synchronizing with a synchronous signal, as well as applying a write clock to the frame memory 44-i, in which data is written, in the frame memory section 44.

First, second, . . . Nth communication interface sections (serial ports) 321-1, 321-2, . . . 321-N to which the communication interface sections of the image input apparatuses 15I are respectively connected through communication circuits are connected through a bus line to CPU 322, a memory 323, a hard disk controller 324 connected to a hard disk 324, a memory control section 326, a signal switch driving section 327 and a search image control section 328, as well as being connected to a communication interface section 329 which sends and receives patient data and control signals to and from the still image filing apparatus 304.

The switching of the signal switch 311 is controlled by the control signal from the signal switch driving section 327 which outputs the control signal for selecting the RGB video signals from the image input apparatuses 15I which are respectively connected to the communication interface sections 321-i on the basis of the release message received by the communication interface sections 321-i.

The release message causes the signal switch 311 to be switched and the image data to be written in an empty frame memory 44-i of a smaller number. In order to identify the image input apparatus 15I which outputs the image data written, the memory control section 326 stores, for example, the number of the communication interface section 321-i of the relevant apparatus 15I.

On the other hand, the search image control section 328 controls the switching of a search terminal switching section 331 for the purpose of coping with a case in which a request for image search is given from the communication interface section 321-i, The search terminal switching section 331 has an input terminal which is connected to the still image filing apparatus 304 so that the NTSC video signals read by a search are input thereto, whereby the image of the NTSC video signals can be output to the terminal selected by switching (that is, the image input apparatus 15I).

On the other hand, when a message of examination end is input, the image data stored in the frame memory section 44 which is obtained by releasing (imaging) by the image input apparatus 15I, which is connected to the communication interface section 44-i receiving the message, is output to the still image filing apparatus 403 together with the ID of the patient and the patient data. The image data of a single examination and the information thereof are registered in an image data base of the still image filing apparatus 304.

In this case, the ID data and the like are transmitted to the still image filing apparatus 304 from the communication interface section 329. While the image data is read in turn from the frame memories in the order of numbers of the communication interface sections 321-i with which the image input apparatuses 15I outputting a message of the examination end are discriminated by the memory control section 326. The image data is read by the read clock which is generated from a read signal generating section 333 for generating the read clock synchronizing with the synchronous signal generated from a synchronous signal generating section 332, and converted into an analogue signal by D/A section 334, mixed with a synchronous signal by an encoder 335 and then output as a NTSC composite video signal to the still image filing apparatus 304.

The hard disk 324 has the function of storing the image data which cannot be received in the frame memory section 44 together with the information data of the image data.

The bus line can be connected to an external apparatus by a bus connector 341.

Since the fifth embodiment employs the frame memory section 44 which is common to the image input apparatuses 15I, without using the small capacity image filing apparatuses 17I, it is possible to effectively store image data and reduce the production cost of the image filing apparatus 303.

Figure 48:
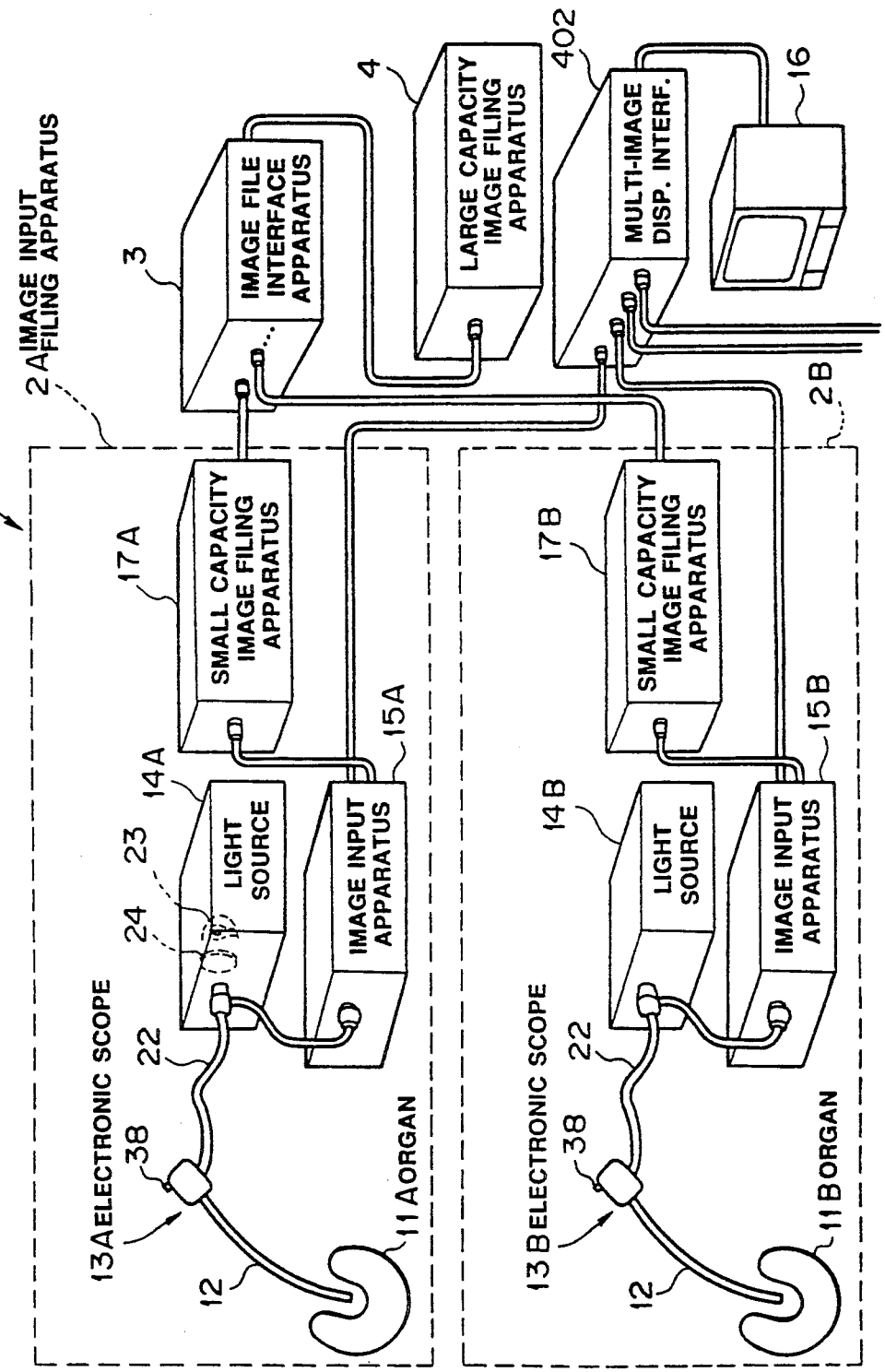

FIG. 48 shows an image filing apparatus 401 in a sixth embodiment of the present invention.

This apparatus 401 is designed so that the color monitors 16I which are respectively provided in the image input/filing apparatuses 2I are replaced by a common color monitor 16 for displaying multiple images thereon.

The image output terminal of each image input apparatus 15I is therefore connected to a multi-image display interface 402, the common color monitor 16 being connected to the image output terminal of the interface 402.

Figure 49:
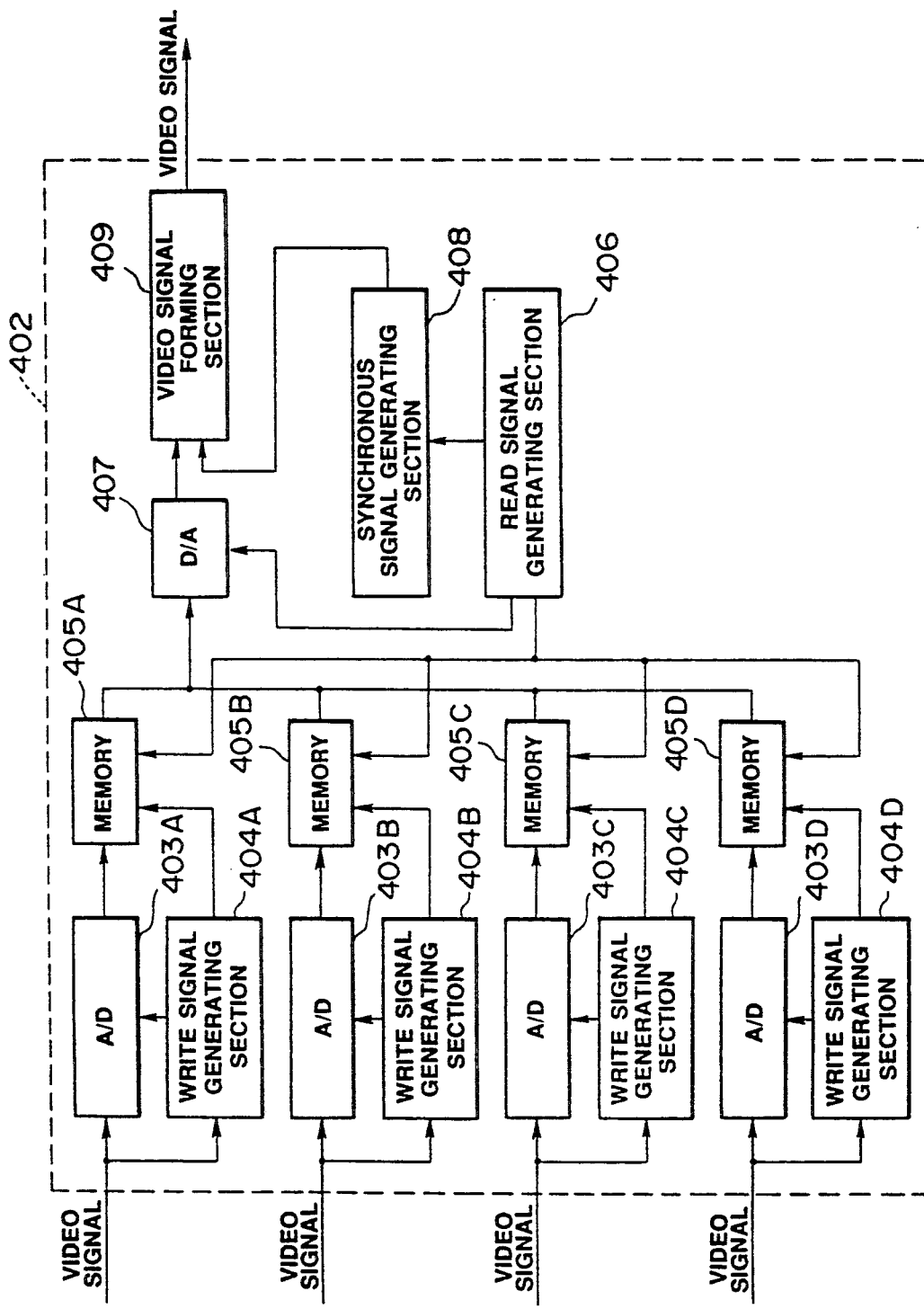

FIG. 49 shows the configuration of the multi-image display interface 402.

The video signal from each image input/filing apparatus 2I is input to an A/D converter 403I, as well as being input to a write signal generating section 404I.

Each write signal generating section 404I generates a clock which synchronizes with a video signal and which is then subjected to A/D conversion in each A/D converter 403I, as well as generating a control signal used in writing the video signal converted in each memory 405I.

The video signals written in the memories 405I are read, for example, from four memories 405A to 405D, while being thinned out by using the read signal from the read signal generating section 406 and then converted into analogue signals by a D/A converter 407.

Figure 50:
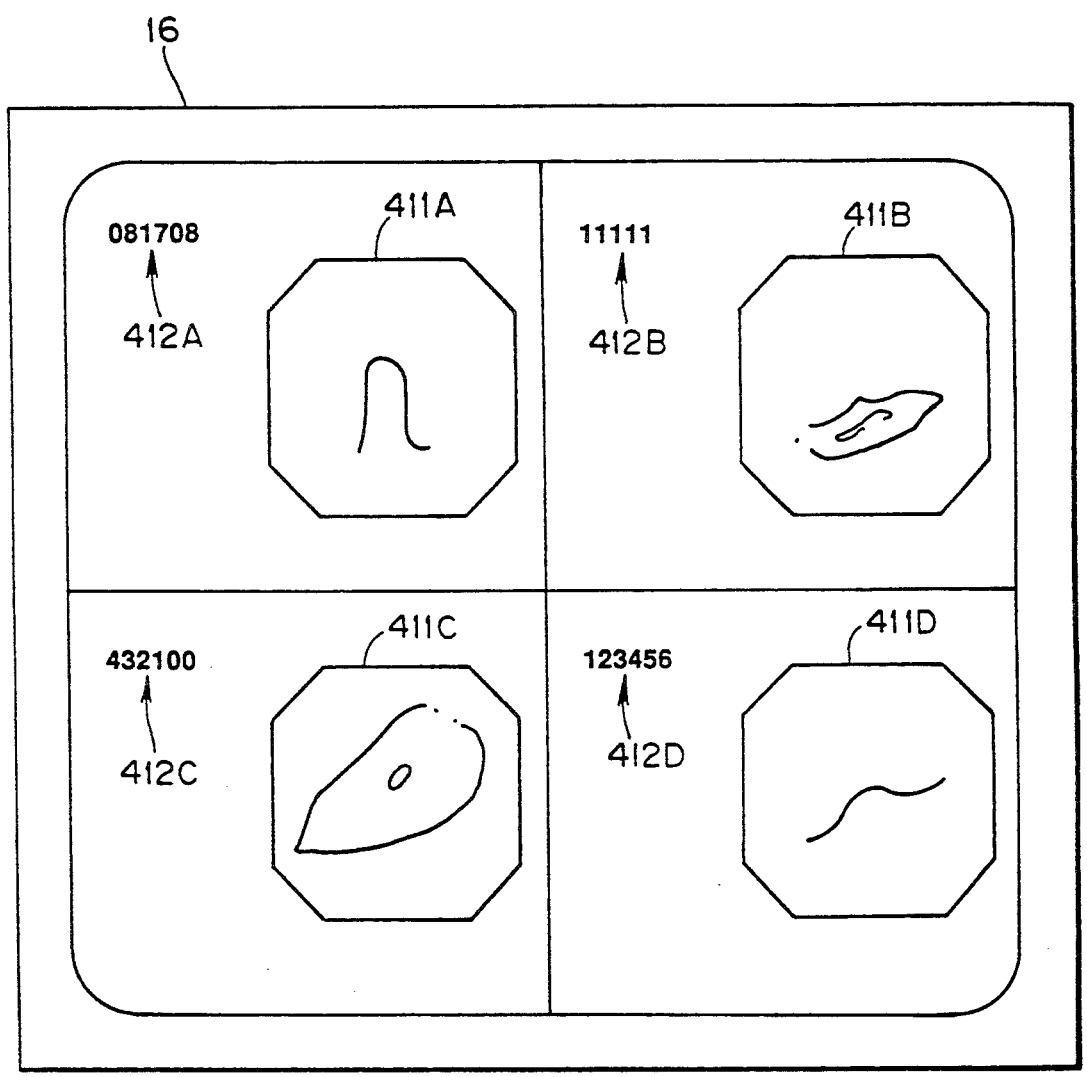

The conversion clock of the D/A converter 407 is also generated from the read signal generating section 406. The read signal generating section 406 sends a standard clock to a synchronous signal generating section 408 to generate horizontal and vertical synchronous signals which synchronizes with the signals read from the memories 405A to 405D. The analogue video signals output through the D/A converter 407 and the synchronous signals from the synchronous signal generating section 408 are mixed in a video signal forming section 409 and then converted into standard video signals such as NTSC signals. These signals may not be mixed and then output from separated output terminals. The video signals are then output to the color monitor 16. FIG. 50 shows an example of the display of the color monitor 16.

The video signals output from the image input apparatuses 15A to 15D are reduced to, for example, a ¼ size and displayed as four reduced images 411A, 411B, 411C and 411D in the upper left, upper right, lower left and lower right portions, respectively. The index 412I of each image 411I is also displayed in the upper left thereof so as to identify the patient of each image.

This embodiment is useful for grasping the working conditions of a plurality of image input/filing apparatuses.

Further, for example, the image formed by the electronic scope 13A is displayed in the upper left by the image input apparatus 15A, while the image with the same index, which was previously registered, is searched for by the image input apparatus 15B and displayed in the upper right, for the purpose of observing changes with time. This method is effective to know the level of cure of the disease of a patient or the level of progress thereof.

For example, one of a plurality of image input apparatuses 15A, 15B, . . . in the first embodiment may be replaced by a search terminal unit. This can be applied to the other embodiments.

In addition, although the synchronous signal generating means is provided in the image processing section 31 of each image input apparatus 15I, one synchronous signal generator may be used so that all the image input apparatuses 15I are synchronously operated. Alternatively, an external synchronous signal may be input to each image input apparatus 15I. This can be applied to the other embodiments.

The unit of a single examination may be changed to the unit of examination images for a single day, examination images for a single person, examination images for a single change to a mobid state, a given number of sheets or other examination units.

The image transmission system is not limited to systems employing RGB signals and NTSC video composite signals, and it may be PAL or SECOM system or the like.

Although the control is effected by interrupt processing in each of the embodiments, it may be performed by polling.

In addition, a hard endoscope may be used in place of the fiberscope of the scope with an external television camera.

Further, although one large capacity image filing apparatus is used, a plurality of apparatuses may be used. In this case, the image data and the data base may be controlled separately or collectively.

The frame memory means of each small capacity image filing apparatus (171I) is not limited to a semiconductor memory such as video RAM or the like, the memory means may comprise a floppy disk, a hard disk or the like or combination thereof.

In each of the above-mentioned embodiments, the large capacity image filing apparatus (4) may be provided with, for example, a reloadable hard disk for temporarily storing image data and information thereof so that the image data and so on are temporarily stored before imaging for a single examination is completed and then transferred in a lump to the optical disk recorder (72) for recording image data and the hard disk (80) for the data base and registered therein when a single examination is completed.

Although each of the embodiments concerns images in the visible region, the present invention is not limited to this region.

Figure 51:
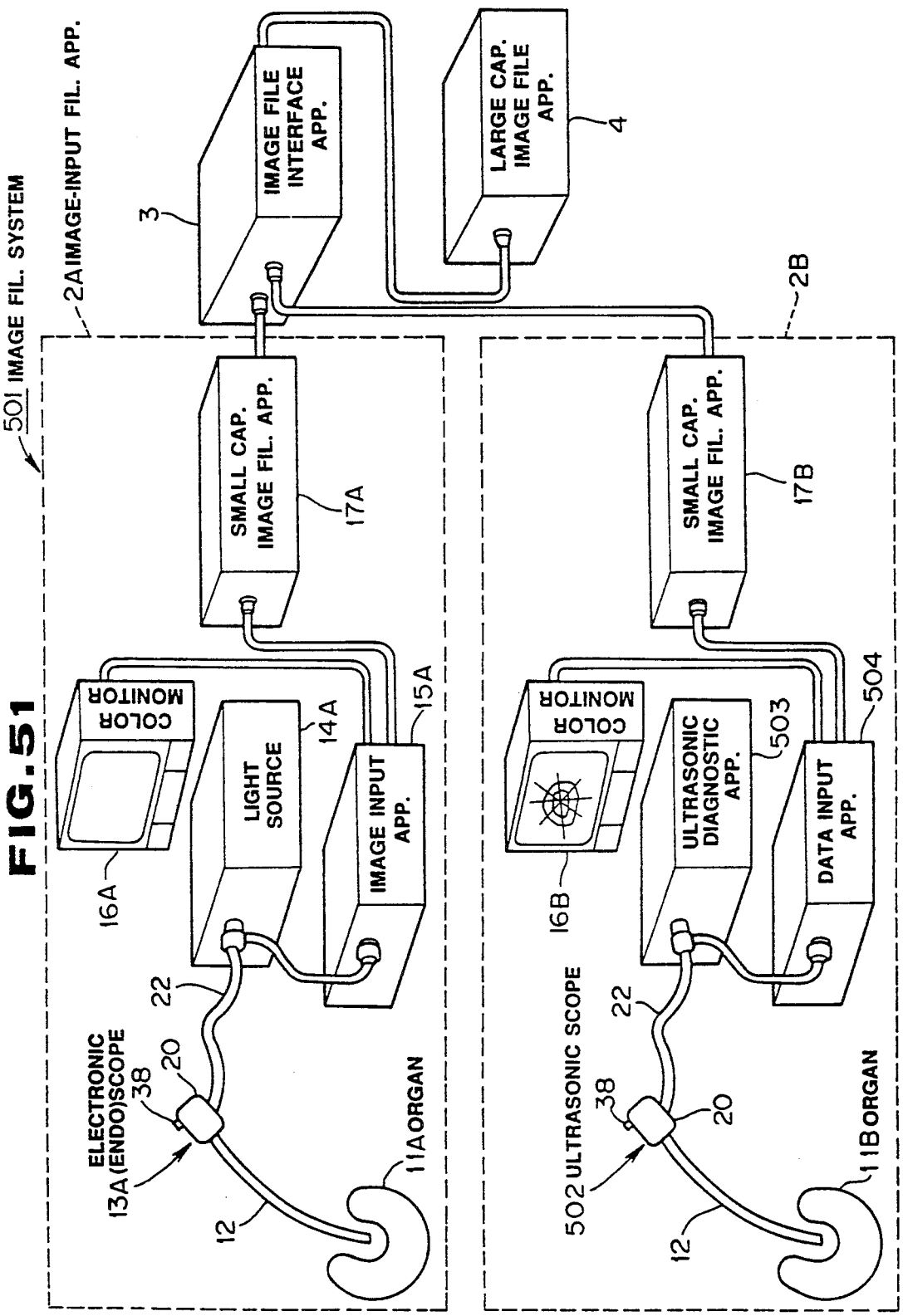
Figure 52:
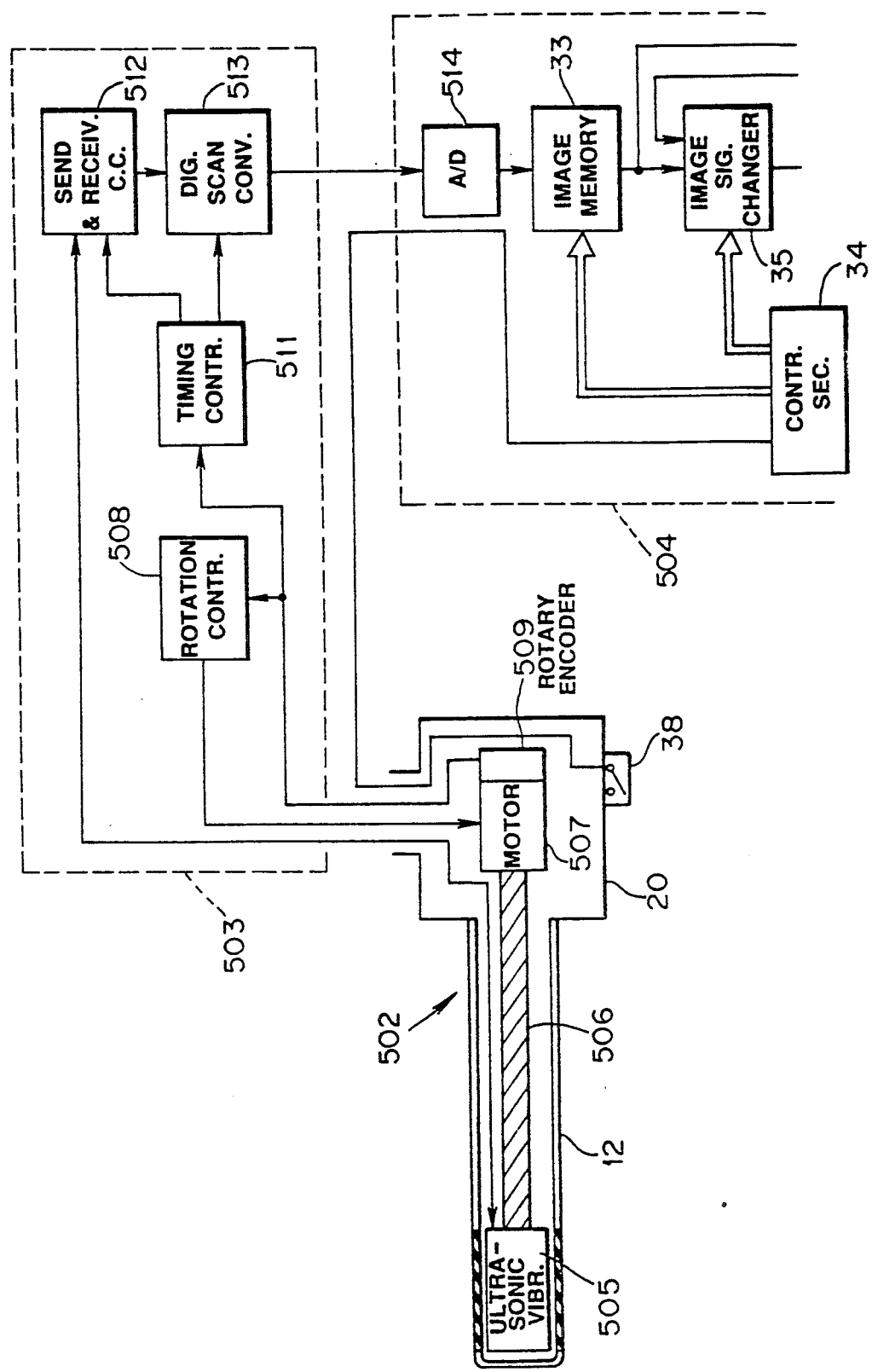

FIG. 51 shows a principal portion of a system 501 which is capable of simultaneously recording and searching the image formed by the electronic scope 13A and the ultrasonotomographic image obtained by an ultrasonic scope 502.

The ultrasonic scope 502 is connected to an ultrasonic diagnostic apparatus 503, as well as to a data input apparatus 504. An image output terminal of the data input apparatus 504 is connected to a color monitor 16B and an image input terminal and a communication interface are noccected to a small capacity image filing apparatus 17B.

In the ultrasonic scope 502, an ultrasonic vibrator 505 is received in one end of a long thin insertion portion 12 thereof and provided at one end of a flexible shaft 506 which is passed through the insertion portion 12. The other end of the flexible shaft 506 is connected to the rotational shaft of a motor 507 in an operational portion 20 so that the ultrasonic vibrator 505 is rotated by the rotation of the motor 507 through the flexible shaft 506.

The motor 507 is rotated by the signal output from a rotation control circuit 508. The motor 507 is provided with a rotation detecting means such as a rotary encoder 509 so that the rotational phase of the motor 507 is controlled by the rotation control circuit 508 in such a manner that the output from the rotary encoder 509 agrees with the standard signal.

The signal output from the rotary encoder 509 is input to a timing control circuit 511 to generate various timing signals which synchronize with the rotation of the motor 507.

The ultrasonic vibrator 505 is connected to a send-receive circuit 512 so as to output a transmit pulse to the ultrasonic vibrator 505 in synchronism with the timing signal from the timing control circuit 511. The ultrasonic vibrator 505 makes an ultrasonic vibration using the transmit pulse and emits an ultrasonic wave in the form of a pulse. The ultrasonic wave emitted is reflected on a portion with discontinuous acoustic impedance in an examination region and received as an ultrasonic echo signal by the ultrasonic vibrator 505.

The ultrasonic echo signal is again converted into an electrical signal, amplified by the send-receive circuit 512 and then input to a digital scan converter 513. The signal is then converted into a standard video signal and then input to an image memory 33 of the data input apparatus 504 through an A/D converter 514.

The video signal stored in the image memory 33 is displayed, for example, as an ultrasono-tomographic image of an examination region, on the color monitor 16B through an image signal switch 35 (refer to the color monitor 16B shown in FIG. 51).

The data input apparatus 504 has the same configuration as each image input apparatus 15I shown in FIG. 6 with the exception that the A/D converter 514 is provided in place of the image processing section 31 in FIG. 6.

This embodiment enables the storage and recording and the search of optical image information in the visible region, as well as the storage and recording and the search of ultrasonic image information.

It is therefore possible to precisely diagnose an examination region of a diseased part by using the optical image of the region, as well as the ultrasonic (acaustic) image thereof.

It is a matter of course that an ultrasonic endoscope provided with an endoscopic function may be used as the ultrasonic scope 502.

Figure 53:
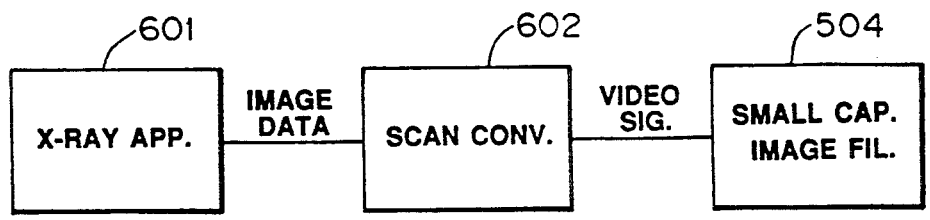
FIG. 53 is a block diagram of an image input/filing apparatus comprising an X-ray apparatus.

In addition, an apparatus for generating an image signal corresponding to an image in the visible region formed by each of the above-described electronic scopes 13I and an apparatus for an acaustic image formed by the ultrasonic scope 502, as well as an apparatus for generating an image signal corresponding to an X-ray absorption (transmission) image formed by an X-ray apparatus 601, as shown in FIG. 53 may be used.

The image data formed by the X-ray apparatus 601 is converted into a standard video signal by a scan converter 602 and then input to a small capacity image filing apparatus 504.

Figure 54:
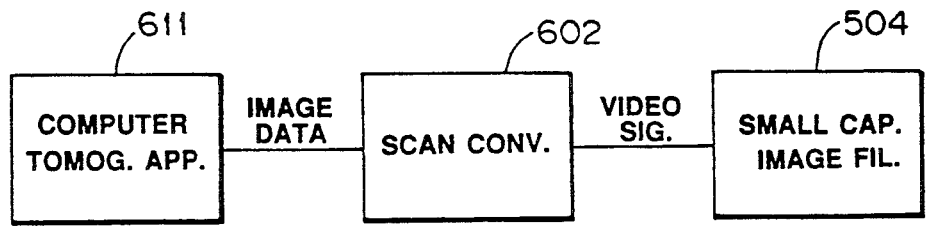
FIG. 54 is a block diagram of an image input/filing apparatus comprising a CT apparatus.

Although the X-ray apparatus 601 produces an image which is projected on a two-dimensional plane, an X-ray CT apparatus 611 may be used for producing an image signal corresponding to a three-dimensional tomographic image, as shown in FIG. 54.

Figure 55A:
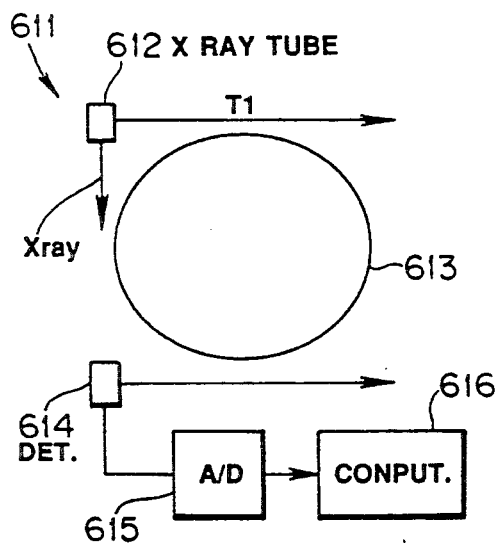
FIGS. 55(a) and 55(b) are a schematic explanatory view of a CT apparatus.

As shown in FIG. 55a, an X-ray tube 612 which emits an X-ray is scanned in the direction T1 vertical to the direction in which a subject 613 is irradiated with an X-ray, and a detector (for example, thallium active sodium iodide NaI(Tl) 614 for detecting the X-ray transmitted through the subject 613 is also scanned in parallel with the X-ray tube 612. The signal output from the detector 614 is stored in a memory of a computer 616 through an A/D converter 615.

Figure 55B:
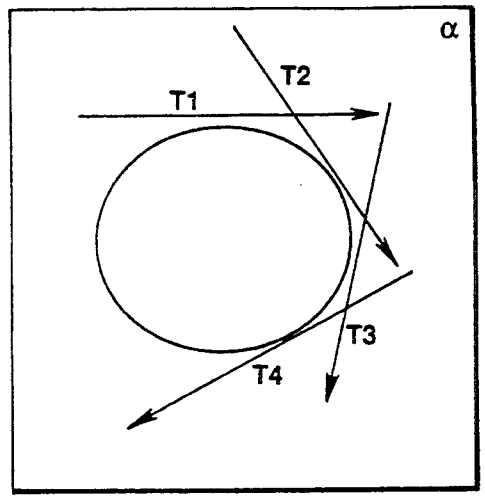

As shown in FIG. 55b, the X-ray tube 612 is scanned in directions T1, T2, . . . . which are different from the above-described direction T1 in the same plane α, and the signals obtained by the detector 614 are stored in the memory in the same way as described above. The computer 616 has the function of calculating the image data stored in the memory, calculating the X-ray absorption efficiency of each position in a round section of an examination region in the plane α and then outputting it to a small capacity image filing apparatus 504 through a scan converter 602. A three-dimensional distribution of X-ray absorption efficiencies can be obtained by performing the same operation for a plane different from the above-described plane α. It is therefore possible to display an X-ray absorption efficiency image of a round section taken along any desired plane of an examination region.

Figure 56:
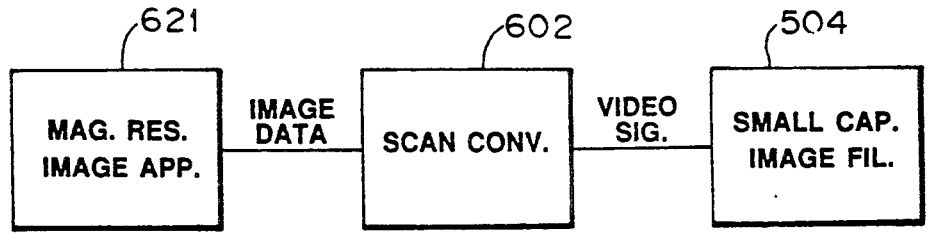
FIG. 56 is a block diagram of an image input/filing apparatus comprising a magnetic resonance imaging (MRI) apparatus.

The present invention can also be used for the image obtained boy an magnetic resonance imaging (MR1) apparatus 621 which employs nuclear magnetic resonance (NMR), as shown in FIG. 56.

For example, although the first embodiment has the configuration which is capable of searching for an image from any desired image input apparatus, the search for an image may be performed by using an image filing apparatus.

It is also apparent that different embodiments can be configured by partially combining the above-described embodiments.

What is claimed is:

1. An image filling system comprising:
   an image signal generating means for generating an image signal of an examination region;
   display means for displaying an image signal output from said image signal generating apparatus;
   a plurality of first image filing means, each having a memory means which is capable of storing a plurality of image signal output from said image signal generating means;
   first information transmission means for transmitting at lest image information to said each of said plurality of first image filing means;
   a second image filing means for storing images stored in said memory means of said plurality of first image filing means, said second image filing means having large capacity memory means for filing the images stored in each of said memory means in a unit of a desired image information;
   second information transmission means for transmitting at least image information to said second image filing means; and
   control means for controlling the transmission of at least image information between said second image filing means and said plurality of first image filing means, wherein said image signal generating means comprises at least one of: (a) a fiberscope with an external television camera, (b) an ultrasonic scope, (c) an X-ray apparatus, (d) an X-ray computer tomograph apparatus, and (e) an image signal generating apparatus which generates a magnetic resonance image (MRI).

2. A system according to claim 1, wherein said image signal generating apparatus has a fiberscope with an external television camera comprising a fiberscope in which one end of an image guide for transmitting an optical image is disposed on the focal surface of an objective optical system disposed at an end of a long thin insertion portion and a television camera which can be mounted to an ocular portion formed at the other end of said image guide and which contains imaging means with a function of photoelectric conversion.

3. A system according to claim 1, wherein said image signal generating apparatus has an ultrasonic scope in which an ultrasonic vibrator with a function in terms of electroacaustic conversion is disposed at an end of a long thin insertion portion.

4. A system according to claim 1, wherein said image signal generating apparatus has an X-ray apparatus for imaging using an X-ray transmitted through an examination region.

5. A system according to claim 1, wherein said image signal generating apparatus has an X-ray computer tomograph apparatus for obtaining an X-ray tomographic image from an X-ray absorption profile of an examination region.

6. A system according to claim 1, wherein said image signal generating apparatus generates a magnetic resonance image (MRI) by employing nuclear magnetic resonance (NMR).

7. A system according to claim 1, wherein said first information transmission means transmits information in two directions to fourth information transmission means for bidirectional information transmission which is possessed by said control means, and said second information transmission means is bidirectional information transmission means for transmitting information in two directions to said fourth information transmission means.

8. A system according to claim 1, wherein said first information transmission means transmits information in two directions to third information transmission means possessed by said image signal generating apparatus, and
   wherein at least one pair of said first, second, third and fourth information transmission means, which are connected to each other, have common digital data transmission means for transmitting an image signal, data signal with respect to said image signal and a control signal in two directions.

9. A system according to claim 8, wherein said digital data transmission means is an SCSI interface.

10. A system according to claim 1, wherein said image signal generating apparatus has means for generating a registering direction for causing the image signal stored in said memory means to be registered in said image filing apparatus.

11. A system according to claim 10, wherein said image signal generating apparatus has means for generating a release signal for a release direction for causing the image signal generated by said apparatus to be stored in said memory means and
    wherein said first information transmission means of said image filing means has digital transmission means which is capable of transmitting an image signal and data information with respect to said image signal in two directions so that an image signal stored in said memory means and a data signal with respect to said image signal can be recorded by connecting cassette-type digital image recording means to said digital transmission means.

12. A system according to claim 1, wherein said large capacity memory means has a large capacity image memory for recording an image signal and data information recording means for recording data information with respect to said image signal.

13. A system according to claim 12,
    wherein said large capacity image memory comprises an optical information recording/regenerating apparatus, and said data information recording means is a hard disk.

14. An image filing system comprising:
    a plurality of signal generating apparatuses for generating image signals of an examination region;
    first memory means which is connected to each of said plurality of image signal generating apparatuses and which is provided with a memory capacity having a plurality of pages for recording an image from the image signal generating apparatus, which outputs a release signal, in connection with index information;
    an image filing apparatus having large capacity memory means for filing an image stored in said first memory means for each of said image signal generating apparatuses; and
    control means for controlling information transmission of at least image information between said image filing apparatus and said plurality of image signal generating apparatuses.

15. A system according to claim 14, wherein each of said image signal generating apparatuses has release generating means for generating said release signal.

16. A system according to claim 15, wherein each of said image signal generating apparatuses has means for generating an image registering prompting signal for registering an image stored in said memory means in said image filing apparatus by using said release signal.

17. An image filing method comprising:
- a storing process of storing in first memory means image data corresponding to an image, for which a release operation is performed, of image data corresponding to images output from a plurality of image signal generating means in connection with an index information of said image stored;
- a registering process for registering all images with the same index, which are directed to be registered by registering direction information for registering the image stored in said first memory means, in a common filing apparatus provided with second memory means having a large capacity in connection with said index information; and
- a search process for transmitting search direction information, which is output from said plurality of image signal generating means, to said common filing apparatus and transmitting an image of an index, which has been previously registered, to said image signal generating apparatuses.

18. A method according to claim 17, wherein said search process first transmits said search direction information to memory control means of said first memory means and performs first memory search as to whether or not the image of a searched index is stored in said first memory means.

19. A method according to claim 17 or 18, wherein said search process is capable of searching for at least one of the before image and the next image which are stored before and next with respect to time the image searched.

20. A method of according to claim 17 or 18, wherein said search process is capable of searching any image belonging to a single examination which is registered at a time different from the time of the image searched from images for a single examination.

* * * * *

UNITED STATES PATENT AND TRADEMARK OFFICE
CERTIFICATE OF CORRECTION

PATENT NO. : 5,124,789

DATED : June 23, 1992

INVENTOR(S) : HIYAMA et al

It is certified that error appears in the above-identified patent and that said Letters Patent is hereby corrected as shown below:

On the title page, Item [75], line 1, "Yutake" should read --Yutaka--.

Signed and Sealed this

Third Day of August, 1993

Attest:

MICHAEL K. KIRK

Attesting Officer

Acting Commissioner of Patents and Trademarks